(12) United States Patent
Shen et al.

(10) Patent No.: US 10,842,749 B2
(45) Date of Patent: Nov. 24, 2020

(54) COMPOSITIONS AND METHODS OF TREATING THERAPY RESISTANT CANCER AND USES THEREOF

(71) Applicants: Haifa Shen, Bellaire, TX (US); Mauro Ferrari, Houston, TX (US); Xiaoyong Deng, Houston, TX (US); Guodong Zhang, Sugar Land, TX (US)

(72) Inventors: Haifa Shen, Bellaire, TX (US); Mauro Ferrari, Houston, TX (US); Xiaoyong Deng, Houston, TX (US); Guodong Zhang, Sugar Land, TX (US)

(73) Assignee: The Methodist Hospital Research Institute, Houston, TX (US)

(*) Notice: Subject to any disclaimer, the term of this patent is extended or adjusted under 35 U.S.C. 154(b) by 1164 days.

(21) Appl. No.: 13/916,380

(22) Filed: Jun. 12, 2013

(65) Prior Publication Data
US 2014/0010879 A1    Jan. 9, 2014

Related U.S. Application Data

(60) Provisional application No. 61/658,666, filed on Jun. 12, 2012.

(51) Int. Cl.
*A61K 9/14*     (2006.01)
*A61K 47/64*    (2017.01)

(52) U.S. Cl.
CPC ............ *A61K 9/146* (2013.01); *A61K 47/645* (2017.08)

(58) Field of Classification Search
None
See application file for complete search history.

(56) References Cited

U.S. PATENT DOCUMENTS

| | | | |
|---|---|---|---|
| 2008/0311182 A1* | 12/2008 | Ferrari .................... | A61K 9/51 424/450 |
| 2009/0029077 A1* | 1/2009 | Atanasoska ........... | A61L 31/022 428/34.1 |
| 2009/0311332 A1 | 12/2009 | Deshong et al. | |

FOREIGN PATENT DOCUMENTS

WO    WO 2005074497 A2 *   8/2005   ........... A61K 9/1271

OTHER PUBLICATIONS

Rousseau, C., et al., "Syndecan-1 antigen, a promising new target for triple-negative breast cancer immuno-PET and radioimmunotherapy. A preclinical study on MDA-MB-468 xenograft tumors", EJNMMI Res., 2011, pp. 1-20.*
Guan, H., et al. "Peptide-Targeted Polyglutamic Acid Doxorubicin Conjugates for the Treatment of αvβ-Positive Cancers ", Bioconjug Chem., 2008, pp. 1812-1821.*
Yang, Z., et al., "Multifunctional Stable and pHResponsive Polymer Vesicles Formed by Heterofunctional Triblock Copolymer for Targeted Anticancer Drug Delivery and Ultrasensitive MR Imaging", ACS NANO, 2010, pp. 6805-6817.*
Van. S. et al., Synthesis, characterization, and biological evaluation of poly(L-γ-glutamyl-glutamine)-paclitaxel nanoconjugate, (Int. J. Nanomed., 2010, pp. 825-837.*
Steeg, P.S. & Theodorescu, D. Metastasis: a therapeutic target for cancer. *Nat Clin Pract Oncol* 5, 206-219 (2008).
Hayes, D.F. et al. HER2 and response to paclitaxel in node-positive breast cancer. *N Engl J Med* 357, 1496-1506 (2007).
(EBCTCG), E.B.C.T.C.G. Effects of chemotherapy and hormonal therapy for early breast cancer on recurrence and 15-year survival: an overview of the randomised trials. *Lancet* 365, 1687-1717 (2005).
Von Hoff, D.D. et al. Risk factors for doxorubicin-induced congestive heart failure. *Ann Intern Med* 91, 710-717 (1979).
Zhang, S. et al. Identification of the molecular basis of doxorubicin-induced cardiotoxicity. *Nat Med* 18, 1639-1642 (2012).
Gabizon, A., Shmeeda, H. & Barenholz, Y. Pharmacokinetics of pegylated liposomal Doxorubicin: review of animal and human studies. *Clin Pharmacokinet* 42, 419-436 (2003).
O'Brien, M.E. et al. Reduced cardiotoxicity and comparable efficacy in a phase III trial of pegylated liposomal doxorubicin HCl (CAELYX/Doxil) versus conventional doxorubicin for first-line treatment of metastatic breast cancer. *Ann Oncol* 15, 440-449 (2004).
Harris, L. et al. Liposome-encapsulated doxorubicin compared with conventional doxorubicin in a randomized multicenter trial as first-line therapy of metastatic breast carcinoma. *Cancer* 94, 25-36 (2002).
Batist, G. et al. Reduced cardiotoxicity and preserved antitumor efficacy of liposome-encapsulated doxorubicin and cyclophosphamide compared with conventional doxorubicin and cyclophosphamide in a randomized, multicenter trial of metastatic breast cancer. *J Clin Oncol* 19, 1444-1454 (2001).
Longley, D.B. & Johnston, P.G. Molecular mechanisms of drug resistance. *J Pathol* 205, 275-292 (2005).
Epenetos, A.A., Snook, D., Durbin, H., Johnson, P.M. & Taylor-Papadimitriou, J. Limitations of radiolabeled monoclonal antibodies for localization of human neoplasms. *Cancer Res* 46, 3183-3191 (1986).

(Continued)

*Primary Examiner* — Michael G. Hartley
*Assistant Examiner* — Lance W Rider
(74) *Attorney, Agent, or Firm* — Winstead PC

(57) ABSTRACT

The present disclosure is directed to a composition for the sustained-release delivery of an active agent to a target cell of an individual. The compositions disclosed herein comprise of at least one porous particle; at least one polymer; and at least one active agent. In an embodiment, the porous particle comprises a plurality of microscale reservoirs. In an exemplary embodiment, the at least one active agent is covalently linked to the at least one polymer to form a polymer-active agent conjugate, and the polymer-active agent conjugate is contained in the plurality of microscale reservoirs of the porous particle. The present disclosure is also directed to a method of treating a tumor, comprising the step of administering to an individual the composition described supra. Additionally, disclosed herein is a method of eliminating tumor stem cells. Furthermore, there is provided a method of circumventing multi-drug resistance in a tumor cell.

63 Claims, 26 Drawing Sheets

(56) References Cited

OTHER PUBLICATIONS

Jain, R.K. Transport of molecules, particles, and cells in solid tumors. *Annu Rev Biomed Eng* 1, 241-263 (1999).
Maeda, H. The enhanced permeability and retention (EPR) effect in tumor vasculature: the key role of tumor-selective macromolecular drug targeting. *Adv Enzyme Regul* 41, 189-207 (2001).
Ferrari, M. Cancer nanotechnology: opportunities and challenges. *Nat Rev Cancer* 5, 161-171 (2005).
Fojo, T. & Menefee, M. Mechanisms of multidrug resistance: the potential role of microtubule-stabilizing agents. *Ann Oncol* 18 Suppl 5, v3-8 (2007).
Atalay, C., Deliloglu Gurhan, I., Irkkan, C. & Gunduz, U. Multidrug resistance in locally advanced breast cancer. *Tumour Biol* 27, 309-318 (2006).
Trock, B.J., Leonessa, F. & Clarke, R. Multidrug resistance in breast cancer: a meta-analysis of MDR1/gp170 expression and its possible functional significance. *J Natl Cancer Inst* 89, 917-931 (1997).
Pivot, X., Asmar, L., Buzdar, A.U., Valero, V. & Hortobagyi, G. A unified definition of clinical anthracycline resistance breast cancer. *Br J Cancer* 82, 529-534 (2000).
Wong, S.T. & Goodin, S. Overcoming drug resistance in patients with metastatic breast cancer. *Pharmacotherapy* 29, 954-965 (2009).
Al-Hajj, M., Wicha, M.S., Benito-Hernandez, A., Morrison, S.J. & Clarke, M.F. Prospective identification of tumorigenic breast cancer cells. *Proc Natl Acad Sci U S A* 100, 3983-3988 (2003).
Yu, F. et al. let-7 regulates self-renewal and tumorigenicity of breast cancer cells. *Cell* 131, 1109-1123 (2007).
Ponti, D. et al. Isolation and in vitro propagation of tumorigenic breast cancer cells with stem/progenitor cell properties. *Cancer Res* 65, 5506-5511 (2005).
Tiezzi, D.G. et al. CD44(+)/CD24 (−) cells and lymph node metastasis in stage I and II invasive ductal carcinoma of the breast. *Med Oncol* (2011).
Giatromanolaki, A., Sivridis, E., Fiska, A. & Koukourakis, M.I. The CD44+/CD24− phenotype relates to 'triple-negative' state and unfavorable prognosis in breast cancer patients. *Med Oncol* (2010).
Stratford, A.L., Reipas, K., Maxwell, C. & Dunn, S.E. Targeting tumour initiatingcells to improve the cure rates for triple-negative breast cancer. *Expert Rev Mol Med* 12, e22 (2010).
Marchini, C. et al. Mesenchymal/stromal gene expression signature relates to basal-like breast cancers, identifies bone metastasis and predicts resistance to therapies. *PLoS One* 5, e14131 (2010).
Karnoub, A.E. et al. Mesenchymal stem cells within tumour stroma promote breast cancer metastasis. *Nature* 449, 557-563 (2007).
Ferrari, M. Frontiers in cancer nanomedicine: directing mass transport through biological barriers. *Trends Biotechnol* 28, 181-188 (2010).
Tasciotti, E. et al. Mesoporous silicon particles as a multistage delivery system for imaging and therapeutic applications. *Nat Nanotechnol* 3, 151-157 (2008).
Shen, H. et al. Enhancing chemotherapy response with sustained EphA2 silencing using multistage vector delivery. *Clin Cancer Res* (accepted) (2013).
Ferrari, M. Vectoring siRNA therapeutics into the clinic. *Nat Rev Clin Oncol* 7, 485-486 (2010).
Tanaka, T. et al. Sustained small interfering Rna delivery by mesoporous silicon particles. *Cancer Res* 70, 3687-3696 (2010).
Xu, R. et al. Multistage Vectored siRNA Targeting Ataxia-Telangiectasia Mutated for Breast Cancer Therapy. *Small* (in press) (2013).
Tanaka, T. et al. In vivo evaluation of safety of nanoporous silicon carriers following single and multiple dose intravenous administrations in mice. *Int J Pharm* 402, 190-197 (2010).
Decuzzi, P. et al. Size and shape effects in the biodistribution of intravascularly injected particles. *J Control Release* 141, 320-327 (2010).
Van de Ven, a.L. et al. Rapid tumoritropic accumulation of systemically injected plateloid particles and their biodistribution. *J Control Release* (2011).
Hurst, D.R. et al. Breast cancer metastasis suppressor 1 up-regulates miR-146, which suppresses breast cancer metastasis. *Cancer Res* 69, 1279-1283 (2009).
Lu, X. & Kang, Y. Efficient acquisition of dual metastasis organotropism tobone and lung through stable spontaneous fusion between MDA-MB-231 variants. *Proc Natl Acad Sci U S A* 106, 9385-9390 (2009).
Minn, A.J. et al. Genes that mediate breast cancer metastasis to lung.*Nature* 436, 518-524 (2005).
Ginestier, C. et al. ALDH1 is a marker of normal and malignant human mammary stem cells and a predictor of poor clinical outcome. *Cell Stem Cell* 1, 555-567 (2007).
Li, X. et al. Intrinsic resistance of tumorigenic breast cancer cells to chemotherapy. *J Natl Cancer Inst* 100, 672-679 (2008).
Marusyk, A., Almendro, V. & Polyak, K. Intra-tumour heterogeneity: a looking glass for cancer? Nat Rev Cancer 12, 323-334 (2012).
Farmer, P. et al. A stroma-related gene signature predicts resistance to neoadjuvant chemotherapy in breast cancer. *Nat Med* 15, 68-74 (2009).
Al-Hajj, M. Cancer stem cells and oncology therapeutics. *Curr Opin Oncol* 19, 61-64 (2007).
Shah, N.P. et al. Transient potent BCR-ABL inhibition is sufficient to commit chronic myeloid leukemia cells irreversibly to apoptosis. *Cancer Cell* 14, 485-493 (2008).
Mann, A.P. et al. E-selectin-targeted porous silicon particle for nanoparticle delivery to the bone marrow. *Adv Mater* 23, H278-282 (2011).
Decuzzi, P. & Ferrari, M. Design maps for nanoparticles targeting the diseased microvasculature. *Biomaterials* 29, 377-384 (2008).
Shen, H. et al. Cooperative, nanoparticle-enabled thermal therapy of breast cancer. *Adv Healthcare Mater* 1, 84-89 (2012).
Alhareth, K., Vauthier, C., Gueutin, C., Ponchel, G. & Moussa, F. HPLC quantification of doxorubicin in plasma and tissues of rats treated with doxorubicin loaded poly(alkylcyanoacrylate) nanoparticles. *J Chromatogr B Analyt Technol BiomedLife Sci* 887-888, 128-132 (2012).
Ananta, J. S., B. Godin, et al. (2010). "Geometrical confinement of gadolinium-based contrast agents in nanoporous particles enhances T1 contrast." Nat Nanotechnol 5(11): 815-821.
Anderson, W. F., B. E. Chen, et al. (2006). "Effects of estrogen receptor expression and histopathology on annual hazard rates of death from breast cancer." Breast Cancer Res Treat 100(1): 121-126.
Bauer, K. R., M. Brown, et al. (2007). "Descriptive analysis of estrogen receptor (ER)-negative, progesterone receptor (PR)-negative, and HER2-negative invasive breast cancer, the so-called triple-negative phenotype: a population-based study from the California cancer Registry." Cancer 109(9):1721-1728.
Burstein, H. J., A. D. Elias, et al. (2008). "Phase II study of sunitinib malate, an oral multi-targeted tyrosine kinase inhibitor, in patients with metastatic breast cancer previously treated with an anthracycline and a taxane." J Clin Oncol 26(11): 1810-1816.
Kummar, S., A. Chen, et al. (2011). "Phase I study of PARP inhibitor ABT-888 in combination with topotecan in adults with refractory solid tumors and lymphomas." Cancer Res 71(17): 5626-5634.
Kummar, S R. Kinders, et al. (2009). "Phase 0 clinical trial of the poly (ADP-ribose) polymerase inhibitor ABT-888 in patients with advanced malignancies." J Clin Oncol 27(16): 2705-2711.
Liedtke, C., C. Mazouni, et al. (2008). "Response to neoadjuvant therapy and long-term survival in patients with triple-negative breast cancer." J Clin Oncol 26(8): 1275-1281.
Lin, N. U., E. Claus, et al. (2008). "Sites of distant recurrence and clinical outcomes in patients with metastatic triple-negative breast cancer: high incidence of central nervous system metastases." Cancer 113(10): 2638-2645.
Minotti, G., P. Menna, et al. (2004). "Anthracyclines: molecular advances and pharmacologic developments in antitumor activity and cardiotoxicity." Pharmacol Rev 56(2): 185-229.
Murakami, M., H. Cabral, et al. (2011). "Improving drug potency and efficacy by nanocarrier-mediated subcellular targeting." Sci Transl Med 3(64): 64ra62.
Navarro, G., R. R. Sawant, et al. (2012). "P-glycoprotein silencing with siRNA delivered by DOPE-modified PEI overcomes doxorubicin resistance in breast cancer cells." Nanomedicine (Lond) 7(1): 65-78.

(56) References Cited

OTHER PUBLICATIONS

Peto, R., J. Boreham, et al. (2000). "UK and USA breast cancer deaths down 25% in year 2000 at ages 20-69 years." Lancet 355(9217): 1822.

Susa, M., A. K. Iyer, et al. (2009). "Doxorubicin loaded Polymeric Nanoparticulate Delivery System to overcome drug resistance in osteosarcoma." BMC Cancer 9: 399.

Tutt, A., M. Robson, et al. (2010). "Oral poly(ADP-ribose) polymerase inhibitor olaparib in patients with BRCA1 or BRCA2 mutations and advanced breast cancer: a proof-of-concept trial." Lancet 376(9737): 235-244.

Twelves, C., J. M. Trigo, et al. (2008). "Erlotinib in combination with capecitabine and docetaxel in patients with metastatic breast cancer: a dose escalation study." Eur J Cancer 44(3): 419-426.

Van den Hurk, C. J., R. Eckel, et al. (2011). "Unfavourable pattern of metastases in M0 breast cancer patients during 1978-2008: a population based analysis of the Munich Cancer Registry." Breast Cancer Res Treat.

Yu, F., H. Yao, et al. (2007). "let-7 regulates self-renewal and tumorigenicity of breast cancer cells." Cell 131(6): 1109-1123.

\* cited by examiner

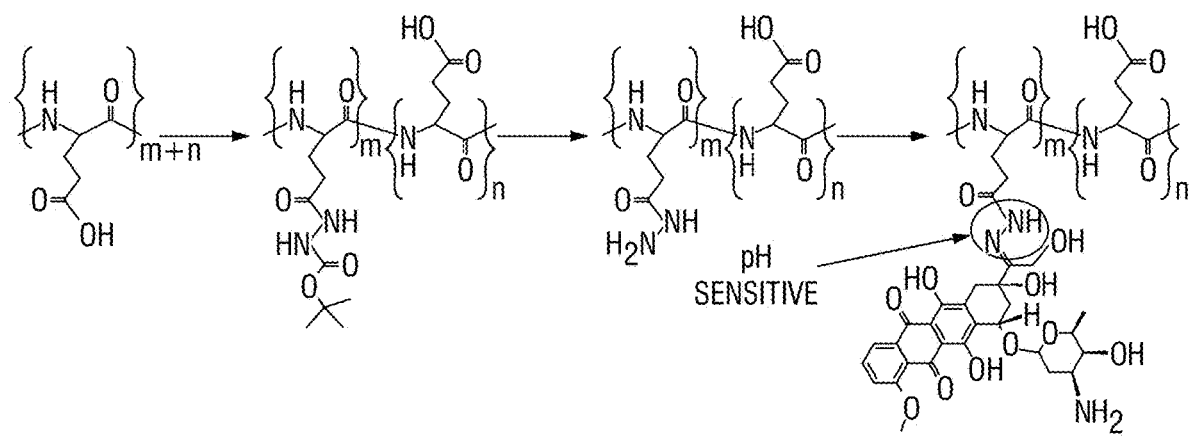
FIG. 1A
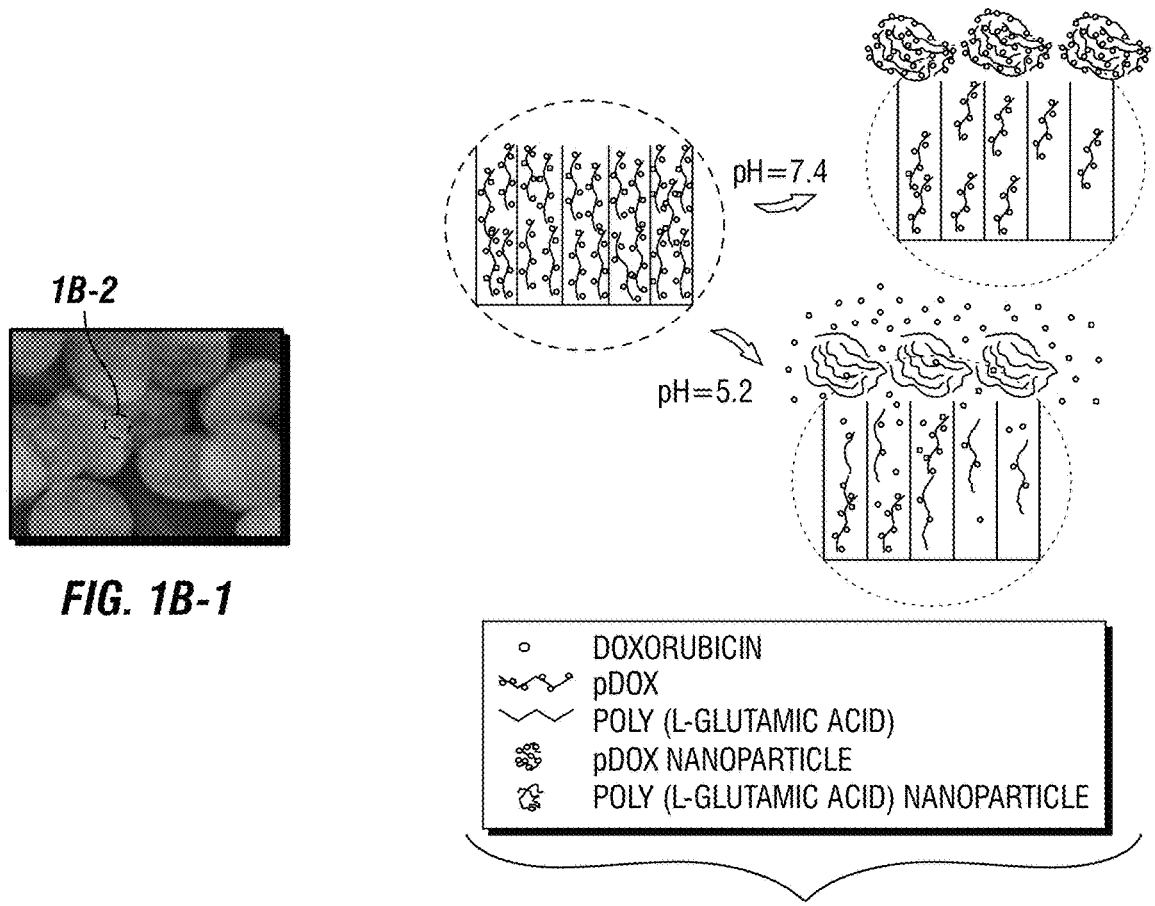
FIG. 1B-1
FIG. 1B-2

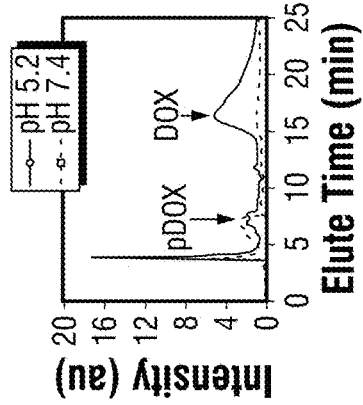
FIG. 1C
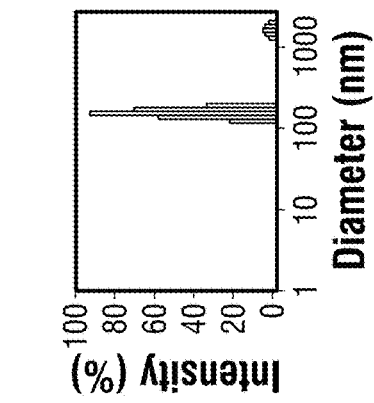
FIG. 1D
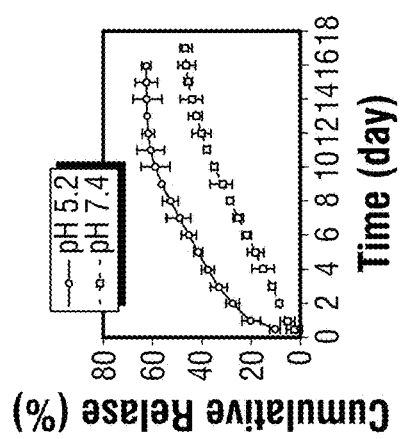
FIG. 1E
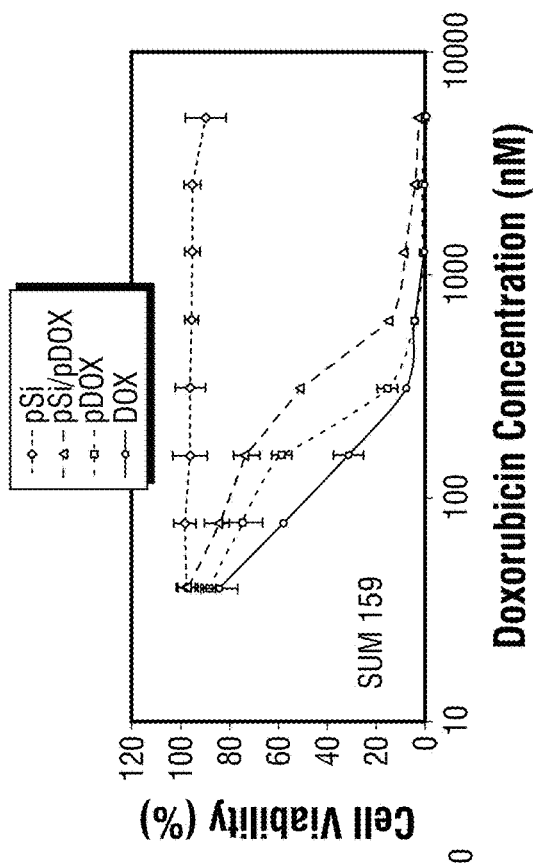
FIG. 1F
FIG. 1G
FIG. 1H
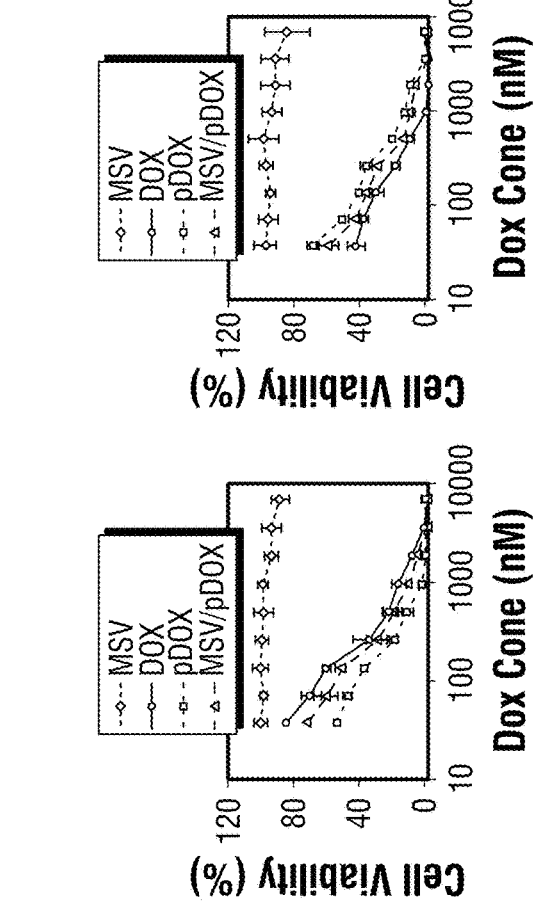

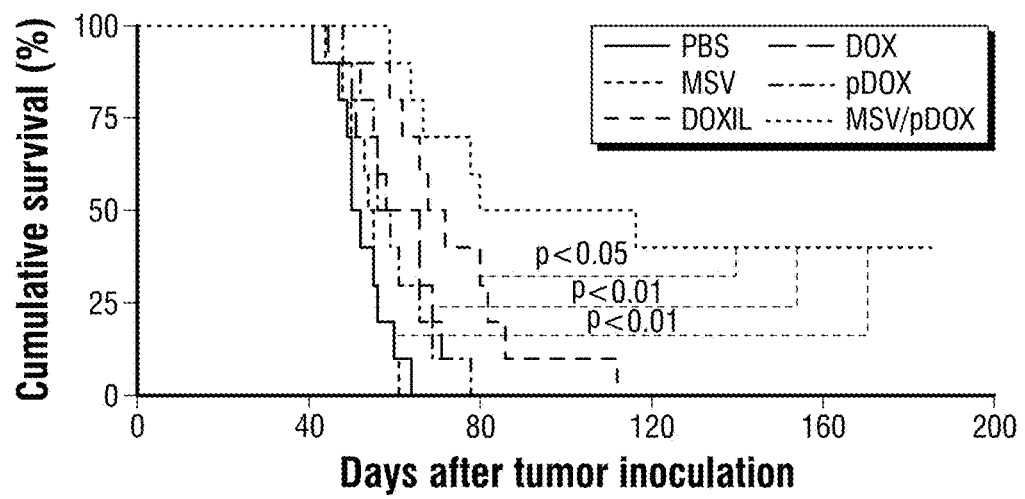
| TABLE 2: MEDIAN SURVIVAL TIME OF MICE AFTER TUMOR INOCULATION | | | | | | |
|---|---|---|---|---|---|---|
| GROUPS | PBS | MSV | DOXIL | DOX | pDOX | MSV/pDOX |
| MEDIAN SURVIVAL (DAYS) | 51 | 54.5 | 70 | 62 | 57.5 | 98 |
*FIG. 5B*
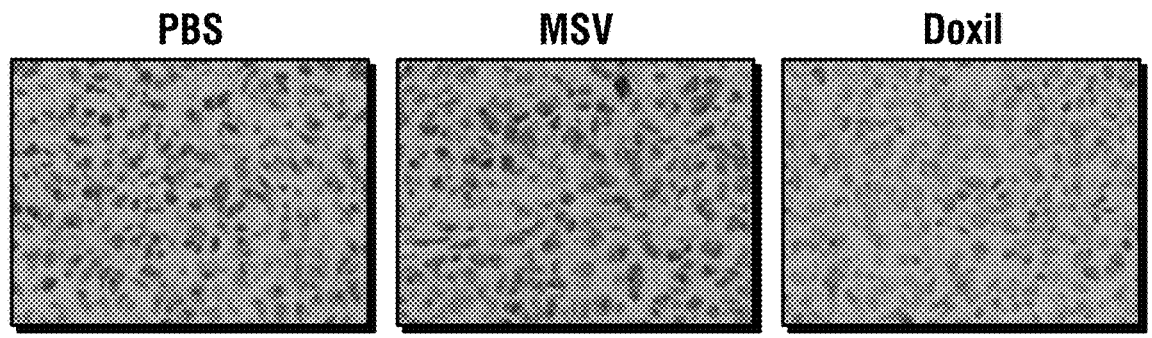
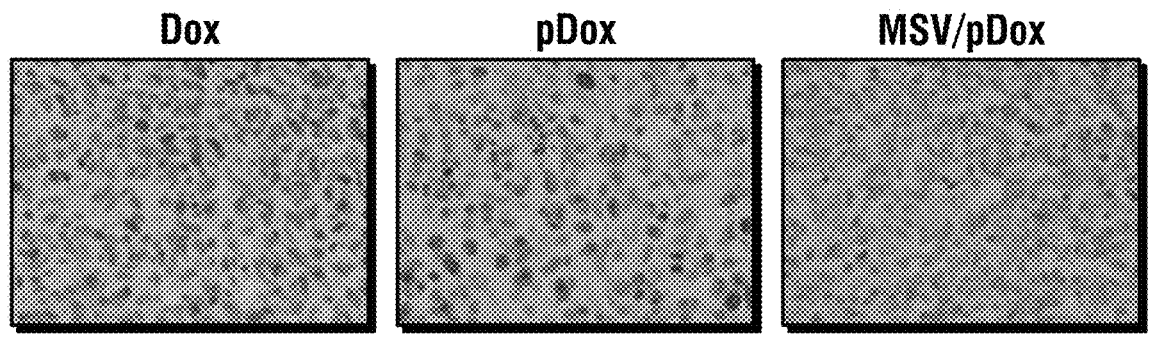
*FIG. 5C*

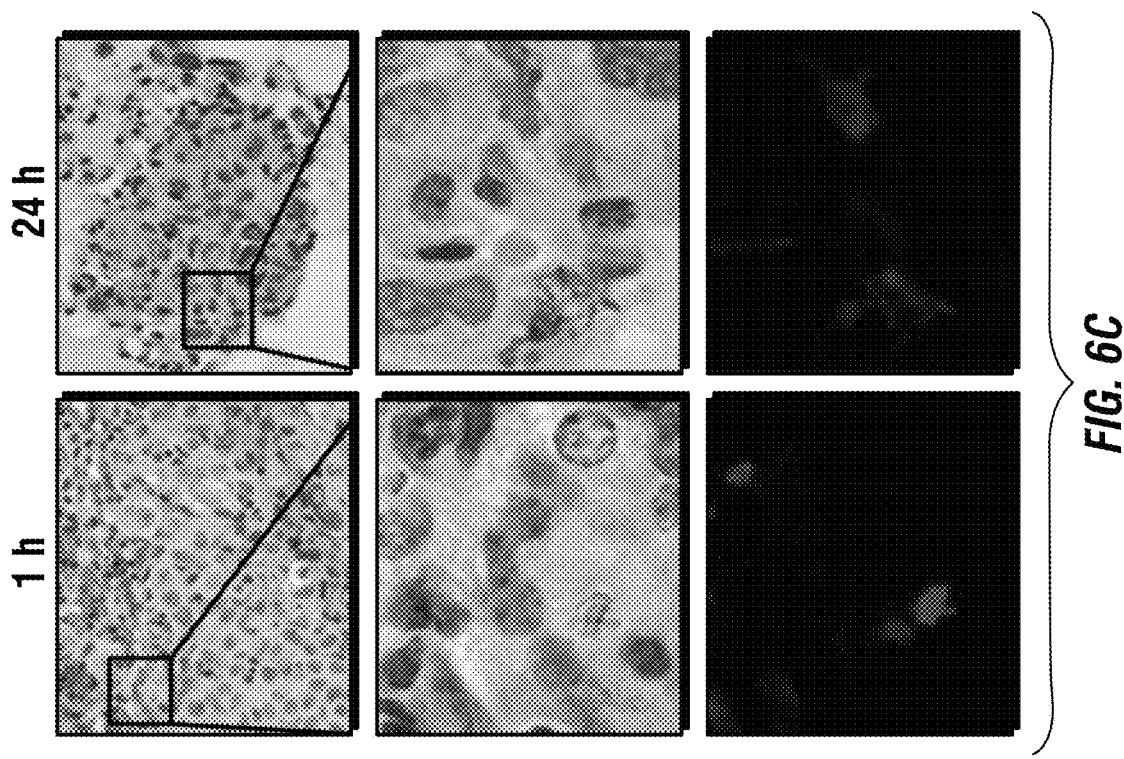
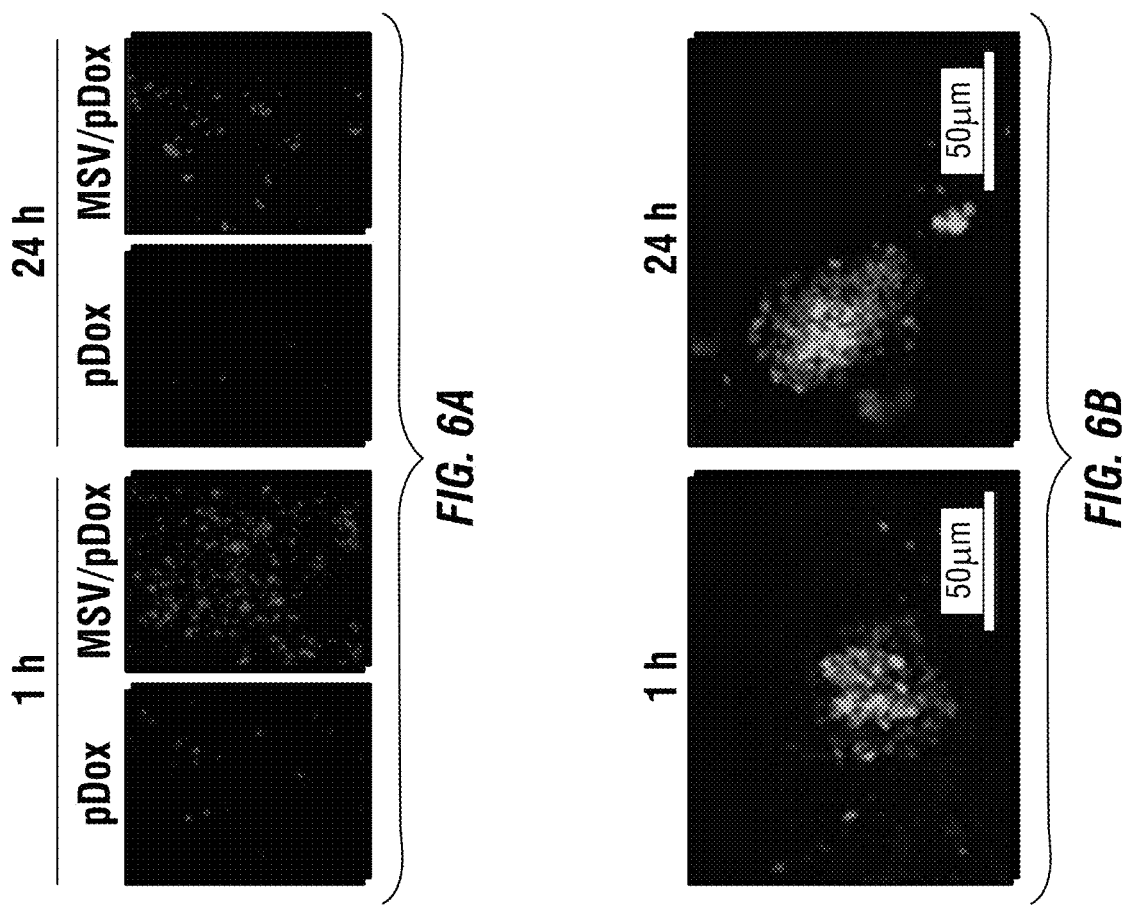
FIG. 6A
FIG. 6B
FIG. 6C

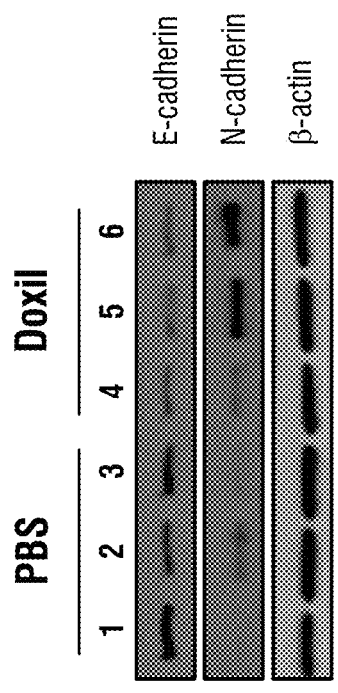
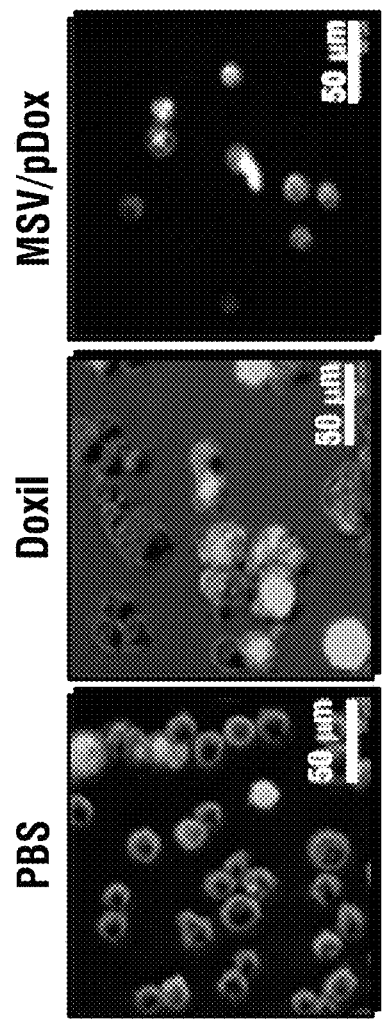
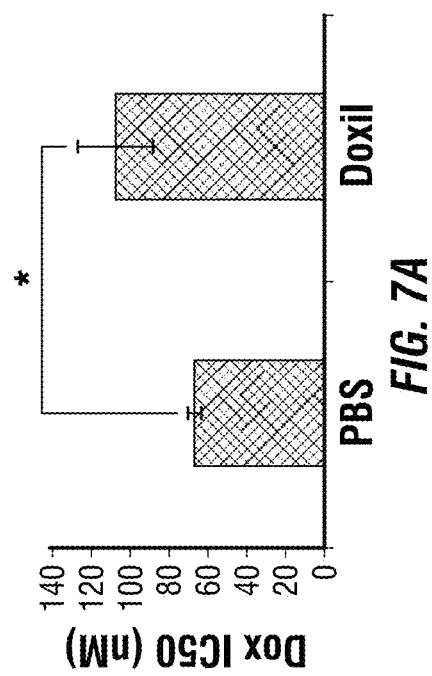
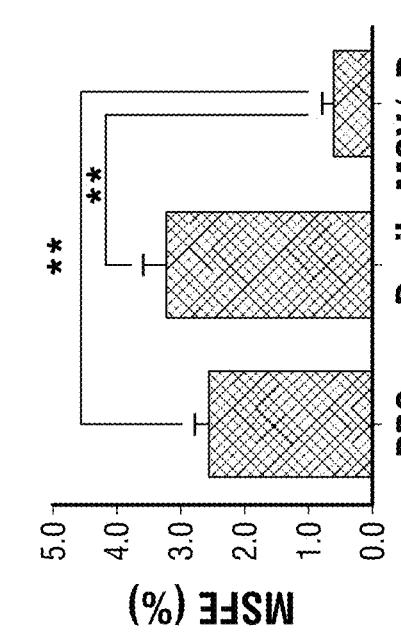
FIG. 7A
FIG. 7B
FIG. 7C
FIG. 7D

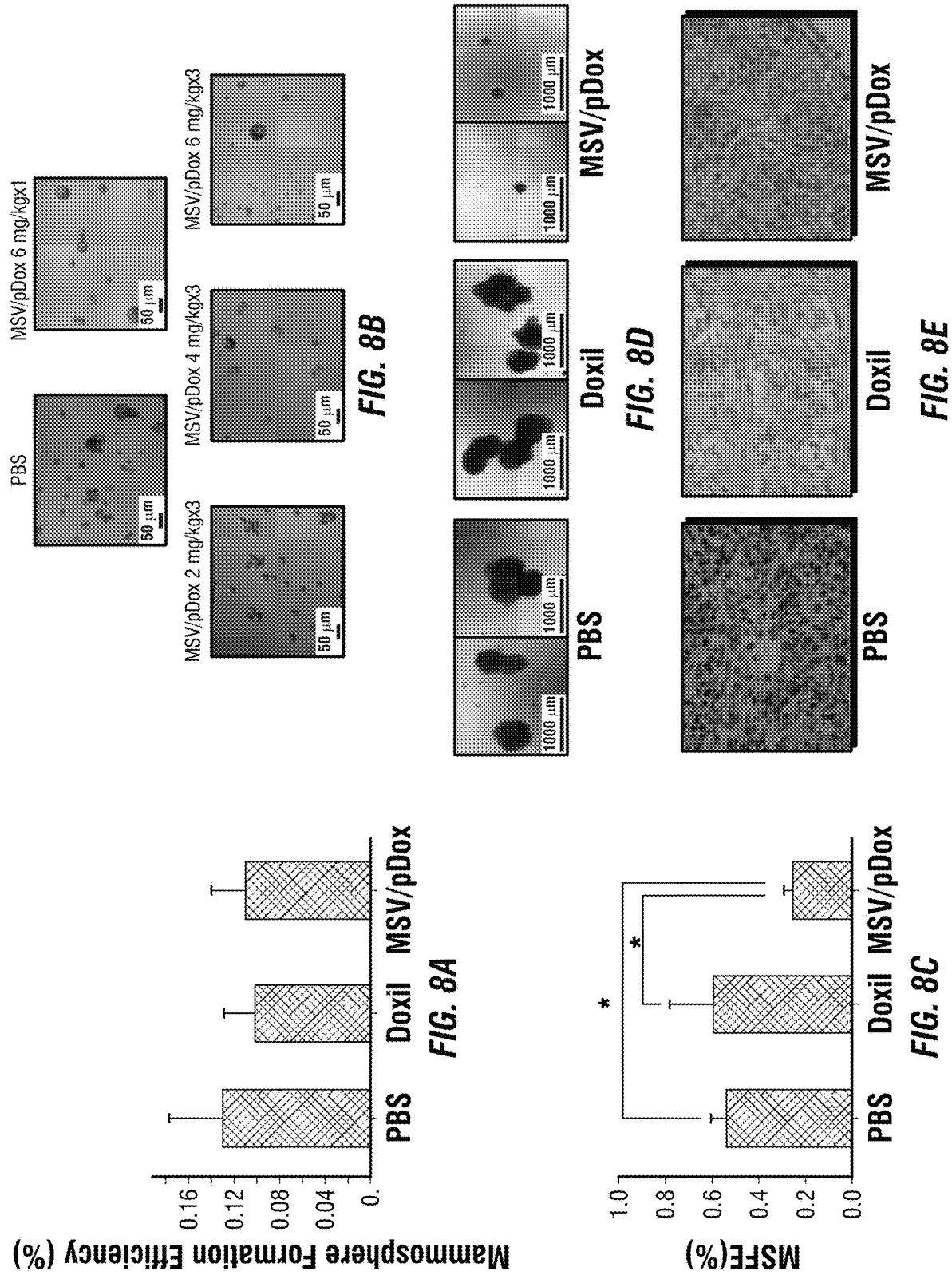

COMPOSITIONS AND METHODS OF TREATING THERAPY RESISTANT CANCER AND USES THEREOF

CROSS-REFERENCE TO RELATED APPLICATIONS

This application claims priority to U.S. Provisional Patent Application No. 61/658,666, filed on Jun. 12, 2012. The entirety of the aforementioned application is incorporated herein by reference.

STATEMENT REGARDING FEDERALLY SPONSORED RESEARCH

This invention was made with government support under W81XWH-09-1-0212 and W81XWH-12-1-0414 awarded by the Department of Defense. The government has certain rights in this invention.

FIELD

The present disclosure relates generally to the field of nanotechnology, and in particular to compositions utilizing micro and/or nanoparticles for delivering therapeutic agents, and methods of making and methods of using such compositions.

BACKGROUND

To produce a therapeutic effect, an active agent must be made available in therapeutically effective amounts at its desired site of action within the body. Delivery of active agents continues to pose a significant challenge. The bioavailability of active agents is affected by numerous factors, including the quantity of active agent administered, the extent and rate of its absorption from its administration site, its distribution, its binding or localization within tissues, its biotransformation, and its excretion. A major challenge to delivery of active agents are the numerous biological barriers within the body, for example the organs of the reticuloendothelial system (RES). In order to overcome these biological barriers and to reach desired plasma drug concentrations, patients are usually administered a much higher concentration of the active agent, leading to therapy related toxicity. A related factor accompanying unfavorable accumulation of the active agent at its desired target site is the development of acquired resistance. Further, the presence of a small population of Tumor Initiating Cells (TICs) that are intrinsically resistant to chemotherapy contributes to the reduced therapeutic effect mediated by an active agent delivered to a target site. TICs get enriched in response to treatment with chemotherapeutic drugs. Accordingly, there remains a need in the art for compositions and methods of use of such compositions, which circumvent drug resistance mechanisms, increase the therapeutic range of an active agent, without producing the related toxicity, and are also effective in eliminating TICs.

BRIEF SUMMARY

In some embodiments, the present disclosure pertains to a composition for the sustained-release delivery of an active agent to a target cell of an individual. In some embodiments, the composition comprises: at least one porous particle; at least one polymer; and at least one active agent. In an embodiment, the porous particle comprises a plurality of microscale reservoirs. In an exemplary embodiment, the at least one active agent is covalently linked to the at least one polymer to form a polymer-active agent conjugate, and the polymer-active agent conjugate is contained in the plurality of microscale reservoirs of the porous particle. In all embodiments, the active agent is released with zero-order or near zero-order kinetics following administration of the composition.

In another embodiment, the present disclosure relates to a method of treating a tumor. Such a method comprises the step of administering to a subject in need thereof the composition described supra. In an embodiment, the method further comprises the polymer-active agent conjugate being released from the porous particle at the target site. In additional embodiments, the method comprises the released polymer-active agent self-assembling into nanoparticles upon coming in contact with an aqueous environment. In an exemplary embodiment, the method comprises the nanoparticles entering a tumor cell via a vesicular transport system.

In some embodiments, the present disclosure relates to a method of eliminating tumor stem cells comprising the step of administering to a subject in need thereof the composition described supra. Such a method comprises the polymer-active agent conjugate being released from the porous particle at the target site. In additional embodiments, the method comprises the released polymer-active agent forming nanoparticles upon coming in contact with an aqueous environment. In an embodiment, the method comprises the nanoparticles entering the tumor cell via the vesicular transport system.

In an embodiment, the present disclosure is directed to a method of circumventing multi-drug resistance in a tumor cell comprising the step of administering to a subject in need thereof the composition described supra. Such a method comprises the polymer-active agent conjugate being released from the porous particle at the target site. Additionally, the method comprises the polymer-active agent conjugate forming nanoparticles upon coming in contact with an aqueous environment. Furthermore, the method comprises the nanoparticles entering the tumor cell via the vesicular transport system.

Other and further aspects, features, and advantages of the present disclosure will be apparent from the following description of the presently preferred embodiments of the disclosure.

BRIEF DESCRIPTION OF THE DRAWINGS

FIGS. 1A-1K show fabrication and characterization of the porous silicon/pDox particles. pDox was synthesized by chemical conjugation of Dox to poly(L-glutamic acid) (FIG. 1A). The pH-sensitive hydrazone linker connecting poly(L-glutamic acid) and Dox is highlighted in a red circle. pDox forms polymer nanoparticles upon release from nanopores of porous silicon in a neutral solution (FIG. 1B-1). In an acidic environment, Dox is cleaved and released from the polymer (FIG. 1B-2). In vitro release of pDox from the porous silicon at pH 5.2 and pH 7.4 is shown (FIG. 1C). FIG. 1D represents dynamic light scattering size measurement of released pDox nanoparticles in phosphate buffer saline (PBS). Separation of doxorubicin and pDox by gel permeation chromatography is also shown (FIG. 1E). pDox in pH5.2 and pH7.4 solutions were applied to a gel permeation column, and eluted with dimethylformamide. Only pDox was detected from the pH 7.4 solution, while free Dox was the predominant form at pH 5.2. MTT assay for cytotoxicity 96 hours after treatment with free Dox, pDox, and porous silicon/pDox on MDA-MB-231 human breast cancer cells (FIG. 1F), MDA-MB-468 human Triple Negative Breast Cancer (TNBC) cells (FIG. 1G), and SUM159 TNBC (FIG. 1H) cells is also shown. FIG. 1I shows SEM image of a 2.6 μm×700 nm discoidal particle loaded with pDox. FIGS. 1J and 1K show confocal images of MSV/pDox. Dynamic light scattering size measurement of released pDox nanoparticles in fetal bovine serum is shown in FIG. 1L;

FIG. 2A shows intracellular trafficking of Dox and pDox in MDA-MB-231 cells treated in culture with equal amounts of Dox or pDox. The presence of doxorubicin (red) in subcellular organelle was visualized by fluorescence microscopy. Nuclei were stained blue with DAPI and late endosomes/lysosomes were stained green with LysoTracker. Nuclear accumulation could be detected as early as 15 minutes after treatment of cells with Dox, while co-localization of Dox with LysoTracker was apparent in pDox treated cells 15 minutes and 1 hour after treatment. FIG. 2B shows expression of P-gp as measured by Western Blotting in MDA-MB-231 cells transfected with a plasmid carrying the MDR gene. FIG. 2C shows MDA-MB-231/MDR cells treated with Dox or pDox, and cell viability measured 72 hours later. The cells were sensitive to pDox, but resistant to treatment with free Dox. FIG. 2D depicts fluorescence images of subcellular organelles. Nuclei were stained in blue DAPI and lysosomes were stained in green with LysoTracker. Images of Dox, nuclei and lysosomes were merged to show subcellular localization of Dox at different time points.

FIG. 2E shows the structural comparison between pDox carrying a pH-dependent hydrazone linker (highlighted in red) and amide-pDox without a hydrazone linker (highlighted in blue). FIG. 2F shows the subcellular trafficking of Amide-pDox. A pH-dependent hydrazone linker used to covalently link pDox to the polymer was more effective in mediating cell killing in MDA-MB-231 (FIG. 2G). In contrast, amide-pDox is not efficacious in killing MDA-MB-231 or MDA-MB-468 tumor cells (FIG. 2H);

FIG. 3B shows Kaplan-Meier plot on animal survival. Superior therapeutic efficacy by Porous silicon/pDox was observed. FIG. 3C illustrates Ki-67 staining of lung tissues from mice sacrificed at the end of the 6-week treatment. Porous silicon/pDox-treated mice had significantly reduced number and size of tumor nodules. FIG. 3D shows immunohistochemical staining of lung tissues from tumor mice after the 6-week treatment. P-gp was overexpressed in tumor cells treated with Doxil, but not with Porous silicon/pDox or PBS;

FIG. 4B shows body weight changes in mice treated weekly with 3 mg/kg Dox or biweekly with 6 mg/kg Doxil, pDox, or porous silicon/pDox. Initial drop in body weight was observed in mice treated with Dox or Doxil. FIG. 4C shows a marked reduction in number and size of tumor nodules in mice treated with porous silicon/pDox;

FIGS. 5A-5C show Porous silicon/pDox attenuates lung metastasis in the murine 4T1 model. 4T1 tumor cells were inoculated in the fourth mammary gland fat pad of female BALB/c mice. The primary tumors were surgically removed when they reached 250-300 mm3, and mice (n=10 mice/group) were treated weekly with 6 mg/kg Dox, Doxil, pDox, or Porous silicon/pDox for four consecutive weeks. Tumor growth was monitored by tracking bioluminescent intensity with the Xenogene IVIS-200 imaging system. Images of representative five mice per group are shown (FIG. 5A). FIG. 5B shows Kaplan-Meier plot on animal survival. Treatment with Porous silicon/pDox offered superior survival benefit over the other treatments. FIG. 5C shows Ki-67 staining of lung tissues after three treatments.

FIGS. 5D-5G show inhibition of lung metastasis in the murine 4T1 model. 4T1 cells were inoculated in the fourth mammary gland fat pad of female BALB/c mice. Two weeks later, the primary tumors were surgically removed, and mice (n=5 mice/group) were treated on the same day with 6 mg/kg Dox, pDox, or MSV/pDox, followed by another treatment 10 days later. All mice were sacrificed three weeks after the first treatment, and lung tissues were examined for tumor metastasis. FIG. 5D shows gross images of representative lung tissues from each treatment group. FIG. 5E shows H&E staining of lung with tumor nodules from each treatment group. FIGS. 5F-1 and 5F-2 show accumulation of Porous silicon/pDox in tumor nodules. The arrows indicate tumor nodules in the lung (FIG. 5F-2). FIG. 5G shows TUNEL assays to detect apoptotic tumor cells in the lung of mice in the negative control groups and those after weekly treatments with Dox, Doxil, pDox, or Porous silicon/pDox.

FIGS. 6A-6F show increased accumulation of Porous silicon/pDox and sustained drug release in tumor tissues. MDA-MB-231 tumor mice were treated (i.v.) with 6 mg/kg pDox or MSV/pDox, and sacrificed 1 hour or 24 hours later (FIG. 6A). Tissue blocks from tumor lung were processed for pathological analysis. Dox accumulated more readily in mice treated with Porous silicon/pDox at both time points than in those treated with pDox. FIG. 6B shows intravital microscopic images of tumor lung 1 hour or 24 hours after treatment with MSV/pDox. Tumor cells were in green and Porous silicon/pDox particles in red. MSV particle accumulation in tumor tissues could be visualized in lung tissue blocks by H&E staining (upper and middle panels) (FIG. 6C). Presence of Dox inside these particles could be visualized under fluorescence microscopy (bottom panel) (FIG. 6C).

FIG. 6D shows the biodistribution of drug. Mice with MDA-MB-231 breast cancer lung metastasis were treated (i.v.) with 6 mg/kg Dox or MSV/pDox. They were sacrificed 1 hour, 1 day, or 7 days later. Dox concentration in major organs was analyzed by HPLC. FIG. 6E shows TUNEL assay of tumor samples collected 1 hour and 24 hours after drug administration. Arrows indicate apoptotic cells. FIG. 6F shows H&E staining of tumor tissues from mice 24 hours after dosing with MSV/pDox. Arrows point to apoptotic bodies.

FIGS. 7A-7G illustrate overcoming intrinsic resistance of porous silicon/pDox by inhibiting tumor initiating cells (TICs). MDA-MB-231 tumor mice were treated biweekly with PBS, Doxil (6 mg/kg), or porous silicon/pDox (6 mg/kg) for 6 weeks (n=5) (FIG. 7A). Mice were sacrificed at the end of the treatment, and lung tissues were collected, minced, and digested. Tumor cells were isolated from the lung, and treated with Dox in vitro (FIG. 7A). Cells isolated from Doxil-treated mice were more resistant to subsequent treatment with Dox than those from PBS-treated mice. FIG. 7B shows Western Blot analysis of epithelial- and mesenchymal-specific biomarkers. Samples in lane 1, 2, and 3 were prepared with tumor cells isolated from control mice, and those in lanes 4, 5, and 6 were from Doxil-treated mice. Single cells were then cultured in low attachment plates for mammosphere formation (FIG. 7C). Fourteen days later, primary mammospheres were digested, and single cells were seeded into low-attachment plates for secondary mammosphere formation. While tumor cells from Doxil-treated mice showed a trend for increase in mammosphere formation, these from porous silicon/pDox-treated mice had lost the ability to form secondary mammospheres. Images of mammospheres from MDA-MB-231 cells engineered with GFP expression are shown (FIG. 7D). FIG. 7E shows dose-dependent inhibition of TICs by porous silicon/pDox. MDA-MB-231 tumor mice were treated biweekly for 6 weeks with 2, 4, 6 mg/kg Porous silicon/pDox (n=5), or once only with 6 mg/kg porous silicon/pDox. Tumor growth was monitored by bioluminescence intensity. At the conclusion of the treatment, mice were sacrificed, and tumor cells were used for mammosphere formation. FIG. 6F shows for FACS analysis and mammosphere assay for TIC activity (FIG. 7F). Left panel depicts the population of $CD44^+/CD24^{-/low}$ cells from primary mammospheres as analyzed by FACS. MDA-MB-231 cells from culture (labeled as "cell culture") served as a control. FIG. 7G shows the secondary mammosphere formation efficiency. *: $p<0.05$, **: $p<0.01$.

FIG. 8A-8E depicts overcoming intrinsic resistance to Porous silicon/pDox treatment by inhibiting TICs. FIG. 8A shows primary mammosphere formation efficiency. No differences were observed for the control mice or the Doxil- or MSV/pDox-treated mice. FIG. 8B shows images of secondary mammospheres by tumor cells isolated from post-treatment MDA-MB-231 tumor mice. FIG. 8C shows a summary of MSFE assay from 4T1 tumor cells isolated from post treatment mice. FIG. 8D shows images of secondary mammospheres by tumor cells from post treatment 4T1 tumor mice. FIG. 8E is an immunohistochemical staining for aldehyde dehydrogenase activity in tumor samples from the lung in post-treatment mice.

FIGS. 11A-11B show degradation of porous silicon particles. The total silicon content analysis in spleen and liver (FIGS. 11A-1 and 11A-2) and images of silicon particles isolated from spleen and liver (FIG. 11B).

DETAILED DESCRIPTION

Figure 1I:
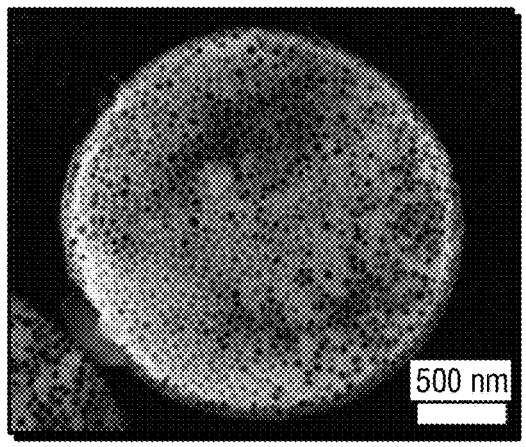

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. Some embodiments of the disclosure may consist of or consist essentially of one or more elements, method steps, and/or methods of the disclosure. It is contemplated that any method or composition described herein can be implemented with respect to any other method or composition described herein. It is to be understood that both the foregoing general description and the following detailed description are exemplary and explanatory only, and are not restrictive of the invention, as claimed.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

"Biodegradable" may be defined as the ability of a substance to be chemically degraded at physiological conditions, in physiological environments, or through enzymatic action. In context of the present disclosure the particle may be biodegradable, i.e., the particle is able to degrade, chemically and/or biologically, within a physiological environment, such as within the body. As used herein, "biodegradable" refers to particles that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible. For the avoidance of misunderstandings, biodegradability does not mean that the biodegradable material must degrade into its respective individual units. It is sufficient that the degradation process leads to soluble molecular species which can be eliminated from an organism by processes such as renal or hepatic excretion. In the present disclosure, the porous particle typically serves as carrier for the polymeric-active agent conjugate, comprising of a polymer linked to an active compound, and additionally, as a release controlling agent. In context of the present disclosure, the particle may also be degradable. For instance, the particle may be one that hydrolyzes spontaneously upon exposure to water, the particle may degrade upon exposure to heat (e.g., at temperatures of about 37 degree centigrade).

"Biocompatible" refers to a material that, when exposed to living cells, will support an appropriate cellular activity of the cells without causing an undesirable effect in the cells, such as a change in a living cycle of the cells, a change in a proliferation rate of the cells, or a cytotoxic effect.

"Microparticle" means a particle having a maximum characteristic size from 1 micron to 1000 microns or from 1 micron to 100 microns. Preferably, the porous particle of this disclosure should have a relatively high porosity to enable loading of the polymeric-active agent conjugate in the pores of the porous particles. Optionally, the porous particles of the present disclosure may be coated with a targeting moiety. Such embodiments may be useful for targeted delivery of the active compound to the desired disease site.

"Nanoparticle" means a particle having a maximum characteristic size of less than 1 micron. Preferably, the polymeric-active agent conjugate of this disclosure forms nanoparticles upon release from the porous silicon particle upon physiological degradation of the porous particle, and upon coming in contact with an aqueous environment.

"Biological Barriers" may be for example, an epithelial or endothelial barrier, such as a blood-brain barrier or intestinal lumen endothelium, that are based on tight junctions, that prevent or limit para-cellular transport of an active agent. Each of the endo/epithelial barrier includes a plurality of sequential sub-barriers, such as tight junction barriers, that owe their molecular discrimination to one or more zonula occluden proteins, and one or more additional biological membranes, such as vascular endothelial basement membrane or a mucosal layer of the intestinal endothelium. Cells of the reticulo-endothelial system may also act as a biological barrier against an active agent encapsulated inside nanoparticles, as such cells sequester/uptake the nanoparticles. The biological barrier may be also represented by a cell membrane or a nuclear membrane in a cell that an active agent has to come through.

"Targeting moiety" is any factor that may facilitate targeting of a specific site by a particle. For example, the targeting moiety may be a chemical targeting moiety, a physical targeting moiety, a geometrical targeting moiety, or a combination thereof. The chemical targeting moiety may be a chemical group or molecule on a surface of the particle; the physical targeting moiety may be a specific physical property of the particle, such as a surface such or hydrophobicity; the geometrical targeting moiety includes a size and a shape of the particle. Further, the chemical targeting moiety may be a dendrimer, an antibody, an aptamer, which may be a thioaptamer, a ligand, an antibody, or a biomolecule that binds a particular receptor on the targeted site.

A physical targeting moiety may be a surface charge. The charge may be introduced during the fabrication of the particle by using a chemical treatment such as a specific wash. For example, immersion of porous silica or oxidized silicon surface into water may lead to an acquisition of a negative charge on the surface, see, e.g., Behrens and Grier, J. Chem. Phys. 115(14), (2001). P. 6716-6761. The surface charge may be also provided by an additional layer or by chemical chains, such as polymer chains, on the surface of the particle. For example, polyethylene glycol chains may be a source of a negative charge on the surface. Polyethylene glycol chains may be coated or covalently coupled to the surface as described in P. K. Jal, S. Patel, B. K. Mishra, Talanta 62 (2004) P 1005-1028; S. W. Metzger and M. Natesan, J. Vac. Sci. Technol. A 17(5), (1999) P 2623-2628; and M. Zhang, T. A. Desai and M. Ferrari, Biomaterials, 19, (1998), p 953.

The term "Porous etched materials" refers to a material in which pores are introduced via a wet etching technique, such as electrochemical etching or electrolysis etching. Examples of porous etched materials include porous semiconductors materials, such as porous silicon, porous germanium, porous GaAs, porous InP, porous SiC, porous $Si_xGe_{1-x}$, porous GaP and porous GaN. Methods of making porous etched particles are disclosed, for example, in US Patent Application Publication No. 2008/0280140, which is incorporated in its entirety, herein by reference.

The expression "zero order or near zero order" as applied to the release kinetics of the active agent delivery composition disclosed herein is intended to include a rate of release of the active agent in a controlled manner over a therapeutically practical time period following administration of the composition, such that a therapeutically effective plasma concentration of the active agent is achieved.

A "Therapeutic Agent" may be any physiologically or pharmacologically active substance that may produce a desired biological effect in a targeted site in a subject. The therapeutic agent may be a chemotherapeutic agent, an immunosuppressive agent, a cytokine, a cytotoxic agent, a nucleolytic compound, a radioactive isotope, a receptor, and a pro-drug activating enzyme, which may be naturally occurring or produced by synthetic or recombinant methods, or any combination thereof. Drugs that are affected by classical multidrug resistance, such as vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) may have particular utility as the therapeutic agent. Cytokines may be also used as the therapeutic agent. Examples of such cytokines are lymphokines, monokines, and traditional polypeptide hormones. A cancer chemotherapy agent may be a preferred therapeutic agent. For a more detailed description of anticancer agents and other therapeutic agents, those skilled in the art are referred to any number of instructive manuals including, but not limited to, the Physician's Desk Reference and to Goodman and Gilman's "Pharmacological Basis of Therapeutics" tenth edition, Eds. Hardman et al., 2001.

As used herein, the terms "treat," "treatment" and "treating" shall be given their ordinary meaning and shall refer to the reduction or amelioration of the progression, severity, and/or duration of a pathological condition or a symptom thereof.

As used herein, the term "Subject" includes animals and humans requiring intervention or manipulation due to a disease state, treatment regimen or experimental design.

The term "Therapeutically practical time period" means a time period necessary for the active agent to be therapeutically effective. The term "therapeutically effective" refers to reduction in severity and/or frequency of symptoms, elimination of symptoms and/or underlying cause, prevention of the occurrence of symptoms and/or their underlying cause, and improvement or remediation of damage.

Tumor metastasis to remote organs is a major cause of cancer mortality[1]. Triple negative breast cancers (TNBC), defined by a lack of minimal expression of the estrogen receptor (ER), progesterone receptor (PR), and Her2/neu, metastasize most frequently to the lungs. Except for a small percentage of patients with a particular genetic background such as mutations in the BRCA1/2 genes, there is currently no effective targeted therapy to treat TNBC. Doxorubicin (Dox) is one of the most potent and often used drugs in adjuvant chemotherapy for metastatic breast cancer[2, 3]. However, Dox tends to cause severe cardiomyopathy in cancer patients due to unfavorable drug accumulation in the heart[4, 5], which imposes a maximum lifetime dosage threshold. Introduction of liposome-encapsulated Dox (trade name "Doxil") with altered biodistribution alleviated cardiac toxicity concerns[6, 7], yet maintained therapeutic efficacy[8, 9].

The rise of resistance to chemotherapeutic drugs including Dox and Doxil is also a major concern. Indeed, therapy resistance is considered the cause of over 90% of failed treatments for metastatic breast cancer[10]. On average, less than 0.01% of untargeted therapeutics reach their desired destination[11, 12]: Unless endowed with a "targeting" ability, based on molecular recognition or biophysical characteristics[13], therapeutic agents cannot accumulate preferentially at the target cancer sites. An additional biodistribution concern is the need for the agents, whether targeted or not, to cross several obstacles on the way to the target sites, including the vascular endothelium, the organs of the reticulo-endothelial system, and the unfavorable mass transport characteristics of tumors[14].

Elevated or repeated dosing is counter-effective and too often leads to adverse biodistribution and therapy resistance. Studies have demonstrated that tumor cells acquire resistance to anthracycline-based chemotherapy after repeated sub-lethal dosing by overexpression of drug efflux proteins, reduction of membrane fluidity, or increased efficiency in DNA repair[15-18]. To further challenge treatment efficacy, recent findings in cancer research have revealed that many tumors are intrinsically resistant to chemotherapy[19]. It has been reported that a small population of tumor-initiating cells (TICs) are intrinsically resistant to conventional treatments, including chemotherapy, hormonal therapy, and radiation therapy[20-22]. These cells carry the $CD44^+/CD24^{-/low}$ surface markers, form mammospheres in culture, and are enriched in breast cancer metastasis[23]. The TICs are considered most responsible for local recurrence and tumor metastasis to distal organs[24, 25]. Mesenchymalization, a characteristic of many TNBC tumors, has also been attributed to therapy resistance and tumor metastasis[26, 27].

Considering these challenges to cancer therapy, there exists a need in the art for a robust and safe drug delivery system with the ability to target and enrich its payload concentration at tumor sites that would enhance the eradication of targeted cells, reduce chances of the target cell acquiring resistance, and overcome drug resistance mechanisms.

Application of nanomedicine to fight drug-resistance has been explored by multiple laboratories. The present disclosure pertains to porous silicon particles loaded with polymeric doxorubicin (porous silicon/pDox or MSV/pDox), a novel therapeutic agent developed based on a combination of nanotechnology and polymer chemistry, as an ideal drug for the treatment of metastatic breast cancers.

In an embodiment, the MSV is comprised of biocompatible, biodegradable nanoporous silicon microparticles (first stage) and nanoparticles comprising the therapeutic moiety (second stage). In some embodiments, the nanoparticle-loaded MSV travels in circulation and settles preferentially on the tumor neovasculature, where the second stage nanoparticles are released over time from the porous silicon first stage particle. In related embodiments, the second stage nanoparticles may be released from the porous silicon first stage particle as the porous silicon naturally and innocuously degrades[28]. In further, embodiments, other methods of release known in the art are also contemplated. In an exemplary embodiment, release of the second stage particle from the first stage particle may occur by passive diffusion. In another exemplary embodiment, release of the second stage particle from the first stage particle may occur in response to a change in physiological environment. In some embodiments, the active agent contained in the second stage particle, may be directly released from the first stage particle. In an exemplary embodiment, release of the active agent may be in response to a change in physiological environment, for example a change in pH.

This technology platform not only allows concentrated delivery of nano-formulated therapeutic agents to tumor tissues but also maintains sustained drug release[29, 31-33]. The nanoporous silicon particles and their degradation byproducts do not cause organ damage or affect the plasma levels of renal and hepatic biomarkers.

The Applicants disclose herein a pH-sensitive polymer-conjugated doxorubicin to be delivered by the porous biodegradable and biocompatible silicon particles or the MSVs (Porous silicon/pDox" or "MSV/pDox"). The term "Porous silicon/pDox" and "MSV/pDox" are used interchangeably throughout the disclosure to describe the pH-sensitive polymer-conjugated doxorubicin contained in porous biodegradable and biocompatible vectors.

This new therapeutic agent offers several major advantages over the anthracycline drugs that are currently available, including: (1) delivery of a large quantity of pDox to tumor tissues; (2) sustained drug release from the porous silicon that maintains therapeutically effective concentration of the active agent at the target site; (3) efficient transport of doxorubicin to the perinuclear region of the cancer cell for effective drug action; and (4) bypassing cellular multidrug resistance mechanisms. Consequently, the composition disclosed herein (Porous silicon/pDOX or MSV/pDox) is successful in treating tumor cells with intrinsic or acquired biological and mass transport-related resistance without the cytotoxicity concerns that often complicate therapy.

Figure 5A:
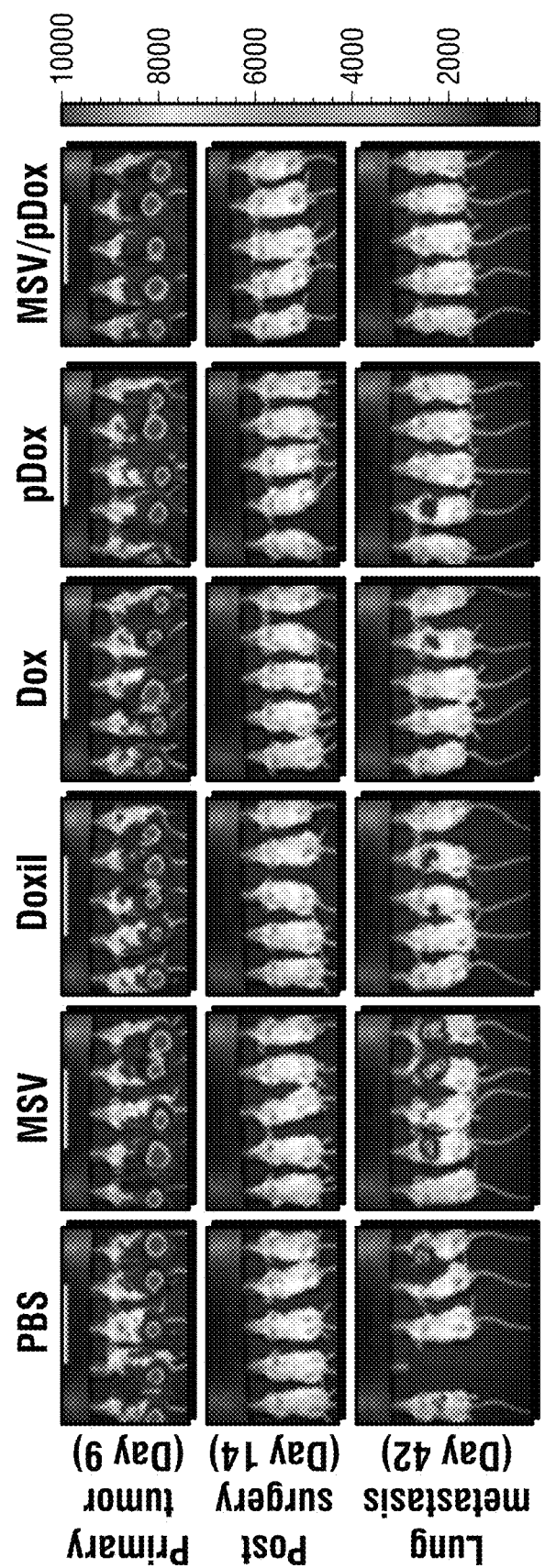
Figure 5D:
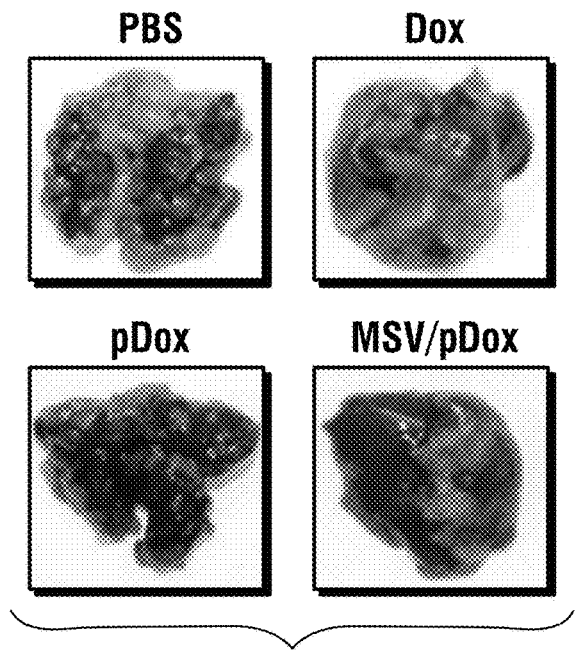
Figure 5E:
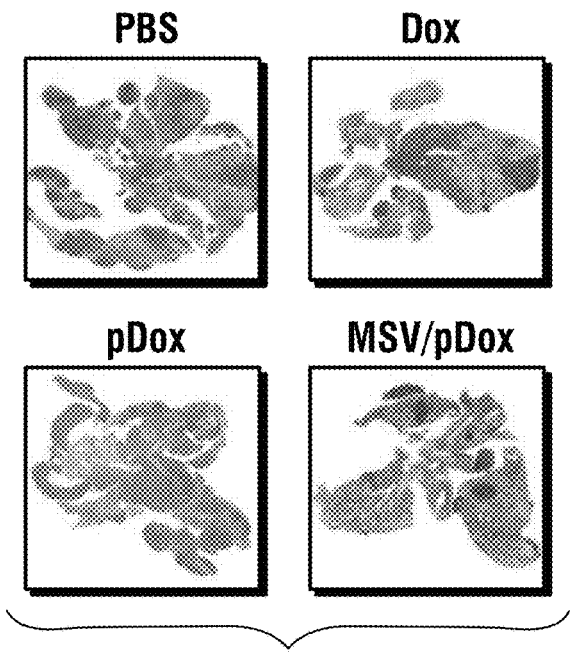
Figures 1, 5F:
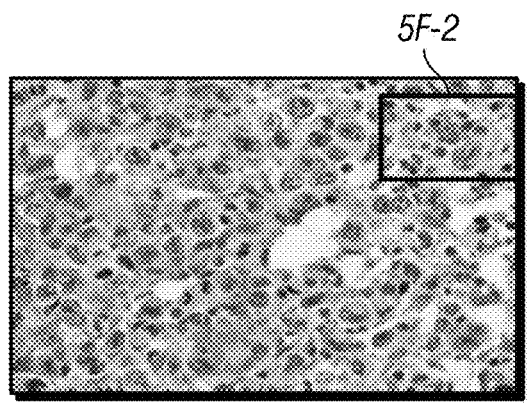
Figures 2, 5F:
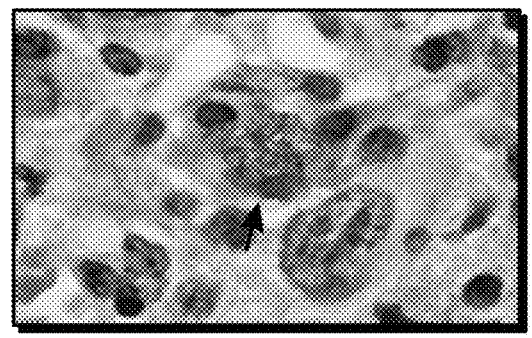
Figure 5G:
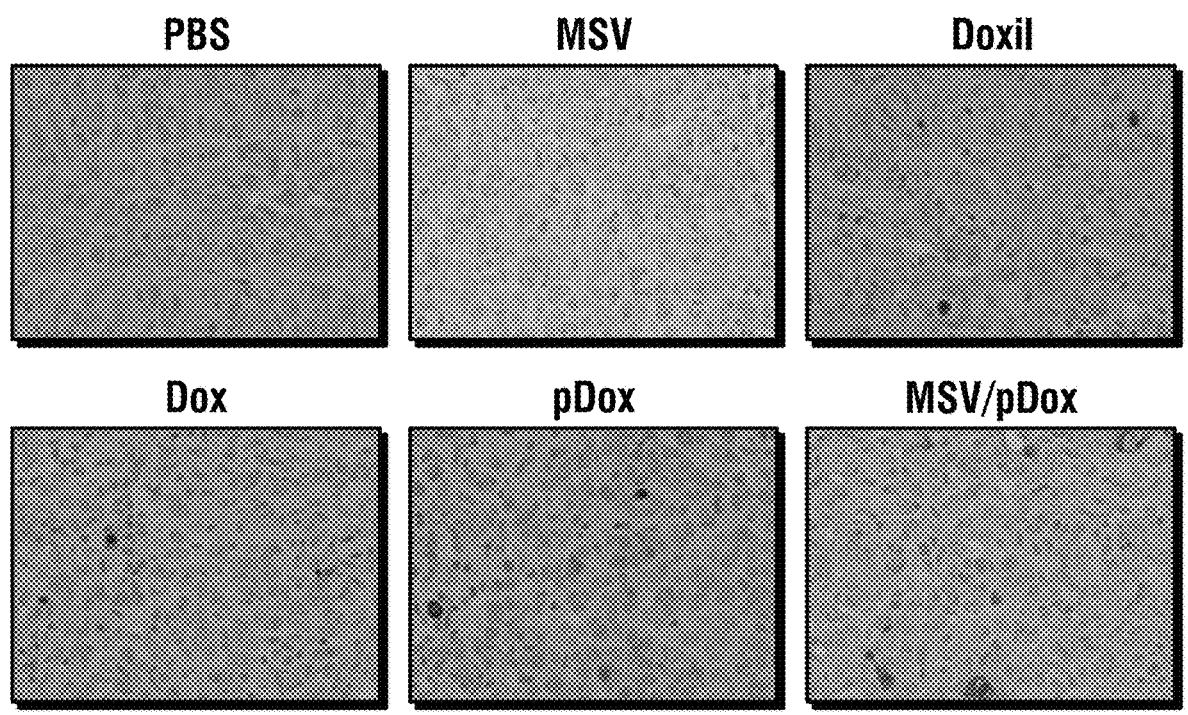

Porous silicon microparticles with the right shape, size, and surface chemical property can be used to efficiently deliver a large amount of therapeutics in nanoparticles to a targeted size[14, 32], and that the silicon particle drug carriers alone have very favorable biocompatibility in vivo[32, 33]. In an embodiment of the present disclosure, the polymer-conjugated doxorubicin was packaged into the nanopores of silicon as single molecules rather than nanoparticles. Although packaged as lipid-soluble single molecule polymeric drugs in porous silicon, polymeric doxorubicin (pDox) exits the silicon nanopores and forms nanoparticles once it comes in contact with the aqueous solution inside the body. Since the pDox nanoparticles have nominal sizes larger than the average pore size of the MSV or the porous silicon, it was concluded that the nanoparticles formed at the opening of the MSV pores, and were released in a sustained fashion for two weeks (FIG. 1). In another embodiment of the present disclosure, the nanoparticles entered tumor cells through vesicular transport, avoiding contact with cell membrane efflux proteins that are largely responsible for cellular resistance to therapy (FIG. 2). Further, the hydrazone bond and its ability to be cleaved under highly acidic conditions to release Dox from the pDox polymer, maintains drug specificity and reduces cytotoxicity in circulation. In another embodiment, the amide-pDox generated by directly conjugating Dox to poly(L-glutamic acid) was found to be ineffective in killing cancer cells (FIGS. 2E-2H).

Many factors can contribute to therapy resistance including tumor heterogeneity[42], tumor-stroma interaction[27, 43], and cancer stem cells[20, 41, 44]. Tumor cells isolated from Doxil-treated mice exhibited characteristics of epithelial-to-mesenchymal cell transition, and showed increased resistance to Dox. To understand the impact of Porous silicon/pDox or MSV/pDox on therapy resistance, a subset of tumor cells (i.e., $CD44^+/CD24^{-/low}$ cells), were extracted to examine their proliferation potential post-therapy, because (1) enrichment of $CD44^+/CD24^{-/low}$ cells has been detected in chemotherapy-treated tumor tissues[41]; and (2) these cells have been shown to be very resilient to chemotherapy drugs[44]. One possible mechanism for the latter phenomenon reason could be that clinical therapeutic dosages are sufficient to damage bulk tumor cells, but are suboptimal against the seemingly more tenacious $CD44^+/CD24^{-/low}$ subpopulation. Administering higher dosages typically poses additional challenges such as cytotoxicity or aberrant biodistribution (e.g., to the heart in the case of doxorubicin). It is necessary to strike a very delicate balance where eradication of the tumor cells does not inadvertently trigger the innate potential for resistance to therapy.

In an embodiment, there are disclosed two concurrent approaches to enhance the elimination of CD44$^+$/CD24$^{-/low}$ cells: (i) elevated, local drug concentration in the tumor environment; and (ii) the extended duration of treatment, which is achieved by sustained release from the MSV vectors. Treatment of tumor-bearing mice with either an unsustained or suboptimal dose may even promote tumor growth, as evidenced by the increased percentage of CD44$^+$/CD24$^{-/low}$ cells in the post-treatment tumor tissues compared to those samples taken from mice treated with PBS (FIG. 7). In some embodiments of the present disclosure the Porous silicon/pDox was found to be very effective in killing Tumor Initiating Cells (TICs).

Enrichment of TICs has been detected in post-chemotherapy tumor tissues. These cells are generally resilient to chemotherapy drugs. It is possible that the clinical therapeutic dosage is effective for killing the bulky tumor cells, but is suboptimal for the TICs. Since drug-related toxicity is a big concern for most chemotherapy drugs due to unfavorable biodistribution, such as heart accumulation in the case of doxorubicin, there is only a narrow therapeutic window for most of the drugs, which makes it almost impossible to raise therapeutic dosage in order to eradicate the TICs. Rather than killing the tumor initiating cells, treatment of cancer patients with such a dosage would most likely trigger acquired resistant in these cells, making the cells even more resistant to therapy. Applicants found that two conditions must be met in order to effectively eliminate TICs: (i) high local drug concentration; and (ii) duration of treatment. It has also been shown in other cancer types that apoptosis of cancer cells can be triggered by a right combination of drug concentration and treatment time[45]. Thus, the compositions and methods disclosed herein offer an unprecedented solution to killing both the bulky tumor cells and the lethal seeds for effective treatment of cancers and prevention of tumor recurrence and metastasis.

With regard to the MDA-MB-231 tumor mice, tumor metastasis to other major organs, such as brain and bone, was observed. During the first 9 weeks into treatment, about 10% of total mice developed metastasis in remote organs, such as bone and the brain. This observation stresses the importance of targeting multiple organs to effectively treat metastatic breast cancer. The Porous silicon/pDox or MSV/pDox particles disclosed herein were effective in bringing large payloads of therapeutics to tumor tissues in the lung. Targeted enrichment of Porous silicon/pDox, for example in the bone may be achieved by conjugating an affinity moiety to selectively bind to the cell surface protein E-selectin, which expresses at a high level in the bone marrow and inflammatory tissues. Application of delivery vectors for multiple tissues/organs may therefore be accomplished using specific targeting moieties.

In summary, Applicants have designed Porous silicon/pDox or MSV/pDox as a new composition with high efficacy, and low toxicity, to treat breast cancer with metastases to the lungs. In some embodiments, MSV/pDox provides for the following advantages: (1) improved drug delivery to the tumor microenvironment, (2) sustained release of pDox from the nanoporous silicon, (3) vesicular transport of pDox to avoid drug efflux by endogenous membrane pumps, and (4) pH-dependent hydrolysis of Dox from the pDox polymer.

As set forth in more detail below, the methods and compositions of the present disclosure have numerous variations. More specific and non-limiting embodiments of the present disclosure will now be described in more detail.

Accordingly, in some embodiments of the present disclosure, there is provided a composition for the sustained-release delivery of an active agent to a target cell of an individual, comprising: at least one porous particle; at least one polymer; and at least one active agent. In an embodiment, the at least one porous particle comprises a plurality of microscale reservoirs. In a related embodiment the at least one active agent is covalently linked to the at least one polymer to form a polymer-active agent conjugate. In another embodiment, the polymer-active agent conjugate is contained in the plurality of microscale reservoirs of the at least one porous particle. In all embodiments of the present disclosure, the active agent active agent is released with zero-order or near zero-order release kinetics following administration of the composition.

The porous particle may be a micro- or a nano-particle. In all these embodiments the porous particle is biocompatible and degradable. Further, the plurality of microscale reservoirs of the porous particle may range in size from about 0.3 μm to about 4 μm. The size of the microscale reservoirs of the porous or nanoporous particle can be controlled to achieve a desired load of the active agent. The porous particles may also be configured into a shape selected from the group consisting of discoidal, spheroid, non-spheroid, oblate spheroid, and combinations thereof. Preferably, the porous particle is a porous oxide material.

Examples of porous oxide materials include porous silicon oxide, silica, porous aluminum oxide, porous titanium oxide, porous iron oxide, and combinations thereof. Fabrication of nanoporous oxide particles is detailed, for example, in Paik J. A. et. al., J. Mater. Res., Vol. 17, August 2002. The nanoporous particle with controllable pore size can be also nanoporous silicon. For details of fabrication of nanoporous silicon particles, see Cohen M. H. et. al., Biomedical Microdevices 5:3, 253-259, 2003; US Patent Application Publication No. 2003/0114366; U.S. Pat. Nos. 6,107,102 and 6,355,270; US Patent Application Publication No. 2008/0280140; PCT Publication No. WO 2008/021908; Foraker, A. B. et al. Pharma. Res. 20 (1), 110-116 (2003); and Salonen, J. et al. Jour. Contr. Rel. 108, 362-374 (2005). Further to this embodiment, the porous particle is a porous etched material. Examples of porous etched materials include porous silicon, porous germanium, porous GaAs, porous InP, porous SiC, porous $Si_xGe_{1-x}$, porous GaP, porous GaN, and combinations thereof.

An active agent's ability to reach an intended target at a desired concentration is usually affected by a multiplicity of biological barriers. The biological barrier may be, for example, an epithelial or endothelial barrier, such as the blood-brain barrier, that is based on tight junctions that prevent or limit para-cellular transport of an active agent. Cells of the reticulo-endothelial system may also act as a biological barrier against an active agent. The biological barrier may also be represented by a cell membrane or a nuclear membrane of a target cell.

In some embodiments, the porous particle is able to overcome at least one biological barrier. The biological barrier is selected from the group consisting of a hemo-rheology barrier, a reticulo-endothelial barrier, a blood brain barrier, a tumor associated osmotic interstitial pressure barrier, an ionic and molecular pump barrier, a cell membrane barrier, an enzymatic degradation barrier, a nuclear membrane barrier, and combinations thereof.

In a related embodiment, the porous particle may have at least one targeting moiety on its surface specifically directed against a target cell. In some embodiments, the at least one targeting moiety is selected from the group consisting of ligands, antibodies, antibody fragments, peptides, aptamers, small molecules, and combinations thereof. For example, ligands can be chemically linked to appropriate reactive groups on the surface of the particle. Protein ligands can be linked to amino- and thiol-reactive groups under conditions effective to form thioether or amide bonds respectively. Methods of attaching antibody or other polymer binding agents to an inorganic or polymeric support are detailed, for example, in Taylor, R., Ed., Protein Immobilization Fundamentals and Applications, pp 109110 (1991).

The polymeric carrier of the present disclosure is preferably biodegradable and biocompatible. In some embodiments, the polymer may be selected from the group consisting of poly-L-glutamic acid, poly(lactic acid), poly(glycolic acid), poly(D-lactic-co-glycolic acid), poly(L-lactic-co-glycolic acid), poly(D,L-lactic-co-glycolic acid), poly(caprolactone), poly(valerolactone), poly(hydroxybutyrate), poly(hydrovalerate), polydioxnanone, derivatives thereof, and combinations thereof.

Any active agent, a small molecule drug or a biomolecular drug, may be delivered using the composition of the present disclosure. In some embodiments, the at least one active agent is a biologically active compound selected from the group consisting of peptides, proteins, therapeutic agents, diagnostic agents, non-biological materials, and combinations thereof. The therapeutic agent may be any physiologically or pharmacologically active substance that can produce a desired biological effect. The therapeutic agent may be a chemotherapeutic agent, an immunosuppressive agent, a cytokine, a cytotoxic agent, a nucleolytic compound, and a pro-drug enzyme, which may be naturally occurring or produced by synthetic or recombinant methods or combination thereof.

Drugs that are affected by classical multi-drug resistance, such as vinca alkaloids (e.g., vinblastine, vincristine), the anthracyclines (e.g., doxorubicin and daunorubicin), RNA transcription inhibitors (e.g., actinomycin-D), and microtubule stabilizing drugs (e.g., paclitaxel) can have particular utility as the therapeutic agent. In some embodiments, the therapeutic agent may be a hydrophobic drug or a hydrophilic drug. Cytokines may be also used as the therapeutic agent. Examples of such cytokines are lymphokines, monokines, and traditional polypeptide hormones. A cancer chemotherapy agent may be a preferred therapeutic agent. For a more detailed description of anticancer agents and other therapeutic agents, those skilled in the art are referred to any number of instructive manuals including, but not limited to, the Physician's Desk Reference and to Goodman and Gilman's "Pharmacological Basis of Therapeutics" tenth edition, Eds. Hardman et al., 2001.

In some embodiments, the therapeutic agent may be selected from the group consisting of genes, nucleic acids, shRNAs, siRNAs, DNA fragments, RNA fragments, plasmids, and combinations thereof. In an embodiment, the therapeutic agent is doxorubicin. In some embodiments, the therapeutic agent is taxol.

The polymer may be conjugated with any number of active agent molecules. In particular, it is to be understood that the conjugate may include a single drug molecule or a plurality of drug molecules. In some embodiments, the one or more drug molecules may be attached to the polymer via a covalent linkage. In some embodiments, the covalent linkage of the active agent with the polymer is via a cleavable bond. In some embodiments, the cleavable bond is selected from the group consisting of hydrazone bonds, ester bonds, amide bonds, anhydride bonds, carbonate bonds, imine bonds, thioester bonds, urea bonds, urethane bonds, disulfide bonds, carbamate bonds, and combinations thereof. In some embodiments, the cleavable bond is cleavable in response to an environmental condition within the target cell. In some embodiments, the cleavable bond is pH sensitive. In more specific embodiments, the polymer-active agent conjugate is polymeric doxorubicin, and the polymer is poly-L-glutamic acid. In some embodiments, the doxorubicin may be covalently linked to the poly-L-glutamic acid via a hydrazone bond.

In some embodiments, the target cell in a subject is a therapy-resistant cancer cell. In various embodiments, the cancer may be at least one of breast cancer, lung cancer, prostate cancer, ovarian cancer, brain cancer, liver cancer, cervical cancer, bone cancer, esophageal cancer, bladder cancer, uterine cancer, testicular cancer, leukemia, lymphoma, stomach cancer, pancreatic cancer, or combinations thereof. In more specific embodiments, the individual has breast cancer, and the breast cancer is Triple Negative breast cancer.

Further embodiments of the present disclosure pertain to a method of treating a tumor using the composition described above. Such a method comprises a step of administering to an individual a composition comprising at least one porous particle; at least one active agent; and at least one polymer. In an embodiment, the porous particle comprises a plurality of microscale reservoirs. In some embodiments, the at least one active agent is covalently linked to the at least one polymer to form a polymer-active agent conjugate. In a related embodiment, the polymer-active agent conjugate is contained in the plurality of microscale reservoirs of the at least one porous particle. Such a method further comprises the release of the second stage particle at the target site. In an exemplary embodiment, the polymer-active conjugate may passively diffuse out of the porous particle at the target site. In another exemplary embodiment, the polymer-active agent conjugate may be released from the porous particle upon the physiologic degradation of the porous particle at the target site. In additional embodiments, the method may further comprise the released polymer-active agent conjugates forming nanoparticles upon coming in contact with an aqueous environment. Furthermore, the method may also comprise the nanoparticles entering the tumor cell via a vesicular transport system. In all embodiments of the present disclosure, the method comprises the active agent being released with zero-order or near zero-order release kinetics following administration of the composition.

In further embodiments of the present disclosure, there is provided a method of eliminating tumor stem cells using the composition described above. Such a method comprises the step of administering to an individual a composition comprising at least one porous particle; at least one active agent; and at least one polymer. In an embodiment, the porous particle comprises a plurality of microscale reservoirs. Further to this embodiment, the at least one active agent is covalently linked to the at least one polymer to form a polymer-active agent conjugate. In a related embodiment, the polymer-active agent conjugate is contained in the plurality of microscale reservoirs of the at least one porous particle. Such a method further comprises the release of the second stage particle at the target site. In an exemplary embodiment, the method may comprise the polymer-active conjugate passively diffusing out of the porous particle at the target site. In a related embodiment, the method further comprises the polymer-active agent conjugate being released from the porous particle upon the physiological degradation of the porous particle at the target site. In an additional embodiment, the method comprises the released polymer-active agent forming nanoparticles upon coming in contact with an aqueous environment. Furthermore, the method comprises the nanoparticles entering the tumor cell via the vesicular transport system. In all embodiments the method comprises the active agent being released with zero-order or near zero-order release kinetics following administration of the composition.

In still yet another embodiment of the present disclosure there is provided a method of circumventing multi-drug resistance in a tumor cell using the composition described above. Such a method comprises the step of administering to an individual a composition comprising at least one porous particle; at least one active agent; and at least one polymer. In an embodiment, the porous particle comprises a plurality of microscale reservoirs. In some embodiments, the at least one active agent is covalently linked to the at least one polymer to form a polymer-active agent conjugate. In a related embodiment, the polymer-active agent conjugate is contained in the plurality of microscale reservoirs of the at least one porous particle. Such a method further comprises the release of the second stage particle at the target site. In an exemplary embodiment, the method may comprise the polymer-active conjugate passively diffusing out of the porous particle at the target site. In some embodiments, the method further comprises the polymer-active agent conjugate being released from the porous particle upon the physiological degradation of the porous particle at the target site. Additionally, the method comprises the released polymer-active agent forming nanoparticles upon coming in contact with an aqueous environment. Furthermore, the method comprises the nanoparticles entering the tumor cell via the vesicular transport system. In all embodiments of the present disclosure, the method comprises the active agent being released with zero-order or near zero-order release kinetics following administration of the composition.

The composition of the disclosure may be designed, formulated and processed so as to be suitable for a variety of therapeutic and diagnostic uses and modes of administration. The composition of the disclosure may be administered to a subject, such as a human, via any suitable administration method in order to treat, prevent, and/or monitor a physiological condition, such as a disease. Embodiments of the composition may be particularly useful for oncological applications, i.e. for treatment and/or monitoring cancer or a condition, such as tumor associated with cancer. Preferably, however, it is adapted for parenteral administration. As used herein, parenteral administration includes any invasive route of administration, such as intravenous, subdermal, intradermal, subcutaneous, intramuscular, locoregional, intratumoral, intraperitoneal, interstitial, and intralesional. Preferred routes of administration of the compositions of the present disclosure may include, without limitation, intravenous, subcutaneous, and intraperitoneal. The compositions of the present disclosure and their suspension for injection can be adapted for parenteral administration, which means that they can be formulated and processed to meet the requirements of parenteral dosage forms. Such requirements are, for example, outlined in the major pharmacopoeias.

EXAMPLES

The following examples are provided to more fully illustrate some of the embodiments of the present disclosure. It should be appreciated by those of skill in the art that the techniques disclosed in the examples which follow represent techniques discovered by the inventors to function well in the practice of the disclosure, and thus can be considered to constitute exemplary modes for its practice. However, those of skill in the art should, in light of the present disclosure, appreciate that many changes can be made in the specific embodiments that are disclosed and still obtain a like or similar result without departing from the spirit and scope of the disclosure.

Example 1

Synthesis of Polymeric Doxorubicin

Hydrazide groups were conjugated to the glutamic acid side chains of poly (L-glutamic acid) via mixing acid anhydride reaction. Briefly, N-morphylmorline (Sigma-aldrich) was added to poly (L-glutamic acid) (Sigma-aldrich) in anhydrous dimethylformamide (DMF), followed by dropwise addition of isobutyl chloroformate at 4° C. under Argon gas. After stirring for 15 min, carbazic acid tert-butyl ester (Sigma-aldrich) in DMF was added. The resulting solution was allowed to react for 30 min at 4° C. and 2 h at room temperature. To synthesize the final product, 100 mg poly (L-glutamic acid hydrizide)-co-poly (L-glutamic acid) was dissolved in 200 mL anhydrous methanol, and 100 μL of trifluoro acetic acid was added. Dox hydrochloride was then added, and the mixture was stirred at room temperature for 48 hours under Argon gas. The polymer Dox was concentrated, dialyzed in methanol, and purified with Sephadex-LH20 (Amersham Pharmacia Biotech Co.). Absence of free Dox was confirmed gel permeation chromatography.

Example 2

Fabrication of Porous Silicon/pDox

Discoidal porous silicon particles were fabricated as described previously (Shen, H. et al. 2012 and in FIGS. 11A-11D). The particles were then modified with 2% (v/v) 3-aminopropyltriethoxysilane (APTES) in isopropanol for 48 hours at 55° C. to conjugate primary amine on surface. The APTES-modified 2.6 μm×700 nm porous silicon particles were loaded with concentrated pDox in methanol and dried in vacuum. This loading procedure was repeated twice to achieve maximum loading.

Example 3

Intra-Cellular Trafficking of pDox

MDA-MB-231 cells were seeded at 1000 cells/chamber on culture slides (BD Falcon) in DMEM containing 10% FBS. Dox or pDox was added 24 hours later. Cells were harvested at different time points. To stain late endosome/lysosomes, cells were incubated with 75 nM lysotracker Green (Invitrogen) in DMEM for 45 min, rinsed with PBS, and fixed with 2.5% formaldehyde for 10 min at room temperature. The slides were mounted by using with Pro-Long® Gold antifade reagent with DAPI (Invitrogen). Fluorescent images were captured using a confocal microscope (Nikon A1 Confocal Imaging system)

Example 4

Mammosphere Formation, Flow Cytometry, and Immunohistochemical Staining

Mammosphere formation efficiencies were measured as described previously, but with some modifications[41].

Briefly, lung tissues with MDA-MB-231 tumor metastases were dissected and homogenized. The samples were then digested in DMEM/F12 with 450 U/ml type III collagenase (Worthington, N.J. USA) at 37° C. for 2 hours. Samples were then filtered and rinsed with sterilized water for 20 seconds to lyse red blood cells. The cells were then resuspended in mammary epithelial growth medium (MEGM; Lonza, Md., USA) supplemented with 2% B27, 20 ng/ml basic fibroblast growth factor (bFGF), 10 ng/ml epithermal growth factor (EGF) (Life Technologies, NY USA), and 4 ug/ml heparin (Stemcell Technologies, BC Canada). Cells were seeded into 24-well ultra-low attachment plates (Corning, Mass., USA) with a seeding density of 20,000 cells/well, and incubated for two weeks to allow for mammosphere formation. Primary mammospheres were counted with the Gel count colony counting system (Oxford Optronix, Oxford UK), digested into single cells with 0.05% trypsin, and seeded into 24-well ultra-low attachment plates with a seeding density of 2,000 cells/well. After two weeks of incubation, the number of mammospheres was counted, and mammosphere formation efficiency was calculated by comparing the number of mammospheres to the number of cells originally seeded.

For analysis by flow cytometry, $5 \times 10^5$ isolated single cells were resuspended in Hank's Balance Salt Solution (HBSS) containing 2% FBS, and incubated with monoclonal antibodies (APC-conjugated anti-CD44 and PE-conjugated anti-CD24) at room temperature for 15 minutes. The cells were then washed and resuspended in HBSS containing 2% FBS and 3 µM Sytox Blue (Life Technologies, NY, USA), and analyzed on a BD LSRII flow cytometer (BD, NJ, USA).

To analyze tumor cells with high levels of aldehyde dehydrogenase in metastatic 4T1 tumor, the BALB/c mice with 4T1 lung metastasis were treated with PBS, Doxil (6 mg/kg, weekly), and Porous silicon/pDox (6 mg/kg, weekly) for 3 weeks. Mice were sacrificed one day after the last treatment, and lung tissues were collected, processed, and stained with a rabbit anti-ALDH1A1 antibody (1:600 dilution) from Abcam.

Example 5

Animal Studies

The animal studies were performed in accordance with the guidelines of the Animal Welfare Act and the Guide for the Care and Use of Laboratory Animals, following protocols approved by the Institutional Animal Care and Use Committee (IACUC). MDA-MB-231 human breast cancer cells were engineered with overexpressed luciferase and the green fluorescent protein. To trigger lung metastasis in the MDA-MB-231 model, each nude mouse was inoculated with $3 \times 10^5$ tumor cells in 100 µl PBS by tail vein injection. Tumor growth in the lung was visualized by bioluminescence with the Xenogen IVIS200 system. Tumor-bearing mice were treated with each drug formulation (i.e., free drugs or MSV-loaded drugs) injected biweekly by tail vein injection, or weekly in the case of free Dox.

To generate the mouse 4T1 lung metastasis model, BALB/c mice were inoculated with 4T1 cells ($5 \times 10^4$ cells/mouse) into the mammary gland fat pad. In the pilot study, primary tumors were surgically removed once they reached 400 mm³ in size. The mice received treatment with free drugs or MSV-loaded drugs by tail vein injection on the day of surgery, and a second treatment 10 days later. All mice were sacrificed 17 days post-surgery. In the follow-up study, 4T1 cells that were engineered to express luciferase and GFP, and were inoculated into the mammary gland fat pads of female BALB/c mice. The primary tumors were surgically removed once they reached 250-300 mm³. Mice were treated with 6 mg/kg of the therapeutic agents weekly for 4 weeks, and subsequently maintained to assess survival benefit from treatments.

Intravital microscopic imaging was performed as previously described[36]. Mice were inoculated i.v. with MDA-MB231 cells through the tail vein. Lung metastasis was confirmed two weeks later by measuring bioluminescence. One hour and 24 hours after i.v. administration of MSV/pDox, the tumor-bearing mice were sacrificed, and the chest cavity was immediately opened to expose the lungs to imaging. Three mice were imaged per time point.

Example 6

Analysis of Tissue Distribution of Dox and pDox

Quantitation of doxorubicin was performed using Daunorubicin (Dau, Sigma) as an internal standard[49]. Briefly, tissues were homogenized in PBS (100 mg tissue/330 µL PBS), and then mixed with 10 µL Dau (50 µg/mL). A 4-fold volume of the extraction solution containing chloroform and methanol (3/1, v/v) was subsequently added. The mixture was vortexed for 1 minute, and centrifuged at 13,000 rpm for 10 minutes to separate the aqueous and organic phases. The organic phase was collected, and the solvent was evaporated at 25° C. under a flow of nitrogen. The extract was dissolved in 100 µL methanol, and a 10 µL aliquot was used for HPLC analysis.

Example 7

Preparation and Characterization of Porous Silicon/Polymeric Doxorubicin

Figure 1J:
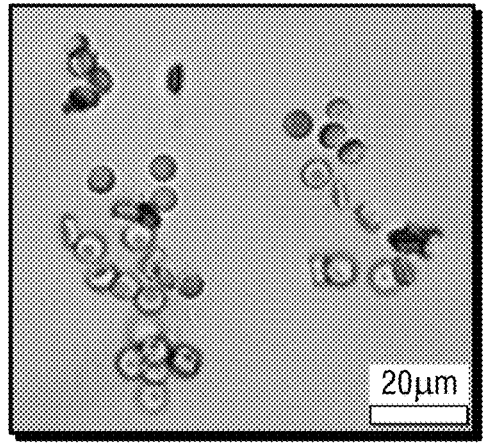
Figure 1K:
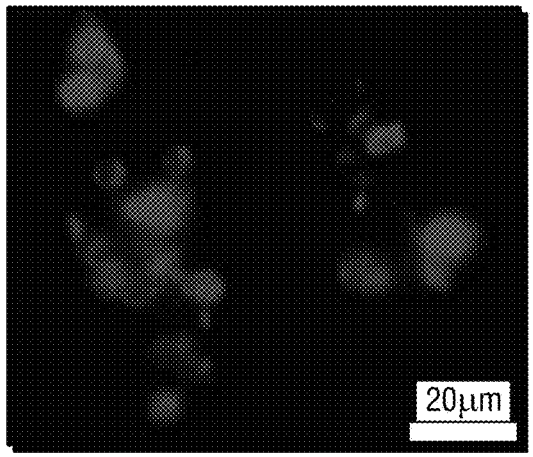
Figure 1L:
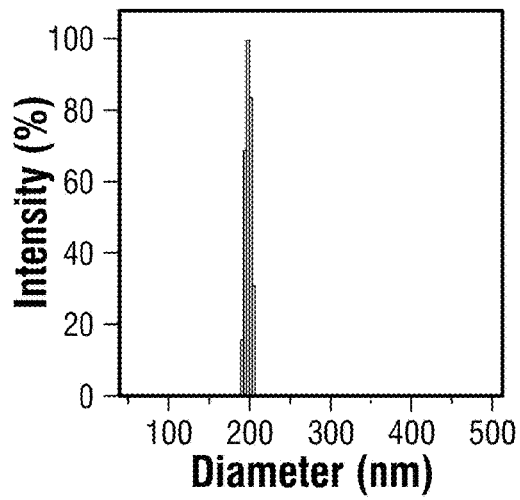

Applicants conjugated doxorubicin to the glutamic acid side chains of poly(L-glutamic acid) via hydrazone linkers (FIG. 1A). The resulting polymeric doxorubicin contained 30% doxorubicin (w/w). Based on the molecular weights of glutamic acid and doxorubicin, it was calculated that one doxorubicin was covalently conjugated to every tenth glutamic acid side chain in the polymer. pDox was hydrophobic, and had a high solubility in methanol (>10 mg/ml). Maximal loading of pDox into nanopores of the porous silicon was achieved by 2 cycles of loading of pDox in methanol solution followed by vacuum dry. 2.6 µm discoidal porous silicon/pDox particles were selected for this study, as previous studies have shown that, comparing to the submicrometer size particles, the big particles preferentially enriched in the lung and in tumor vasculature (Decuzzi, Godin et al. 2010; van de Ven, Kim et al. 2011). SEM image showed clear structure of the silicon particle; many of the nanopores were filled with polymers, indicating pDox was successfully loaded (FIG. 1I). High intensity fluorescence from porous silicon/pDox could be visualized under a confocal microscope (FIGS. 1J, 1K). Based on its chemical structure, it was anticipated that pDox would form nanoparticles once it would be released from porous silicon in the neutral body fluid. Under acidic conditions, the hydrazone linker would be cleaved, and free doxorubicin would be released from the polymer (FIG. 1B-1 and FIG. 1B-2). In vitro test showed constant release of pDox from porous silicon for up to two weeks in 10% fetal bovine solution a neutral pH. Release of pDox from porous silicon particle was quicker at pH5.2, and sustained release of doxorubicin was maintained for up to 10 days (FIG. 1C). It was possible that cleavage of doxorubicin from the polymer could have accelerated the initial release process in the acidic solution. The released pDox nanoparticles had an average diameter of 127 nm in phosphate buffer saline (PBS) and 200 nm in fetal bovine serum (FIG. 1D and FIG. 1L), a size that was wider than most nanopores in the porous silicon carrier. Based on the size difference between the nanopores in MSV (45-80 nm in diameter) and pDox nanoparticles, the final structure of the nanoparticles most likely formed at the opening of the nanopores. Consequently, only one particle per nanopore would be allowed to form at a time, resulting in a sustained release of pDox as demonstrated by the linear release curves from the in vitro tests (FIG. 1C). Gel permeation chromatography analysis confirmed that pDox was the predominant form at pH 7.4, but that they had been converted to free Dox at pH 5.2 (FIG. 1E). Cell-based studies revealed that both free pDox and Porous silicon/pDox were effective in killing MDA-MB-231, MDA-MB-468, and SUM159 human breast cancer cells, and that conjugation of Dox to the polymer did not compromise the drug's activity (FIGS. 1F, 1G, and 1H). Thus, Applicants have established a delivery system for sustained release of doxorubicin.

Example 8

Figure 2A:
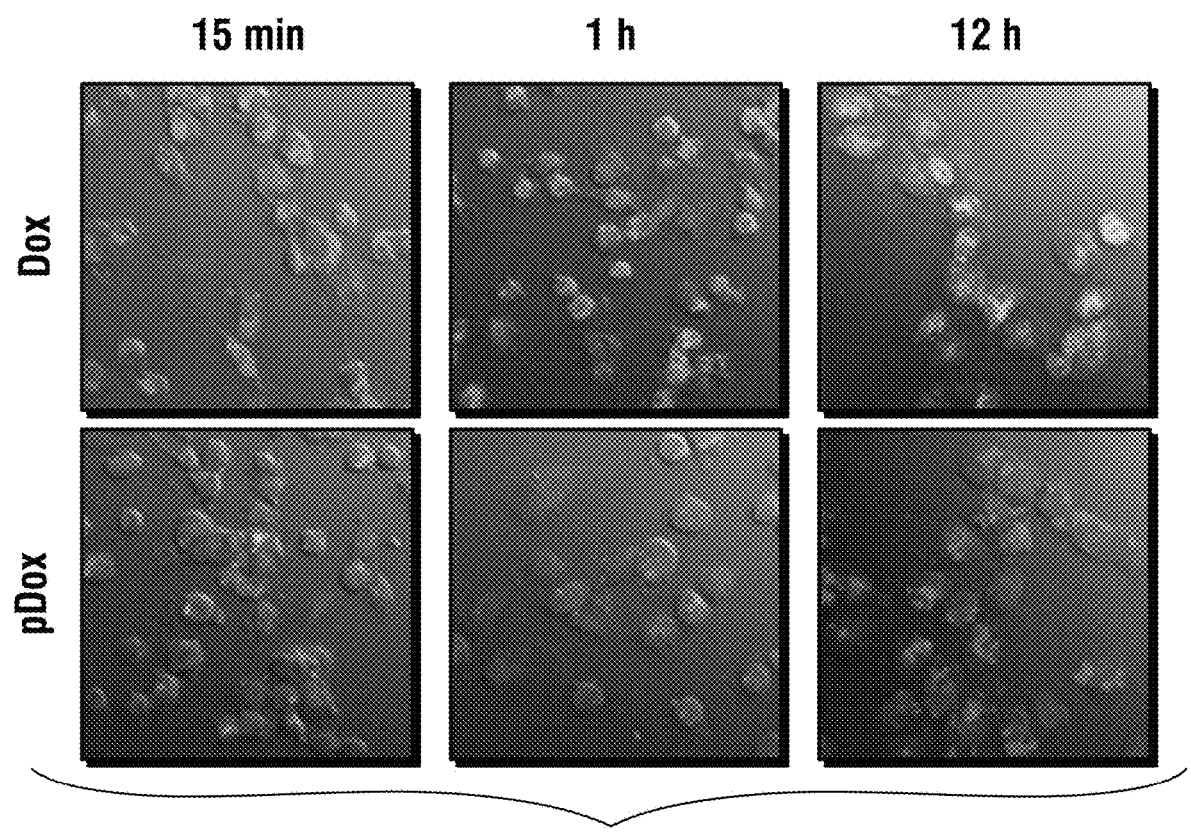
FIGS. 2A-2H show vesicular transport of pDox in tumor cells and effective killing of tumor cells carrying an overexpressed multidrug resistance gene mediated by pDox.
Figure 2B:
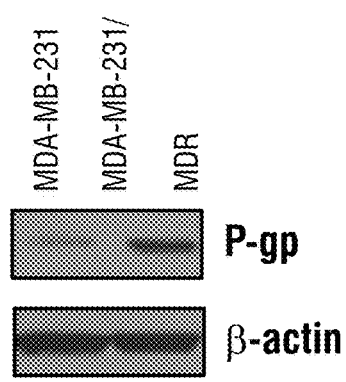
Figure 2C:
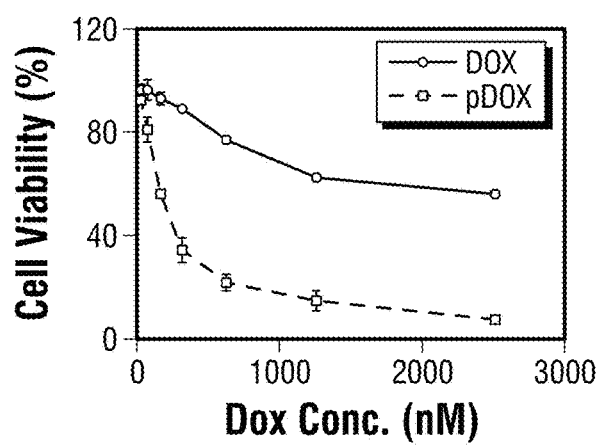
Figure 2D:
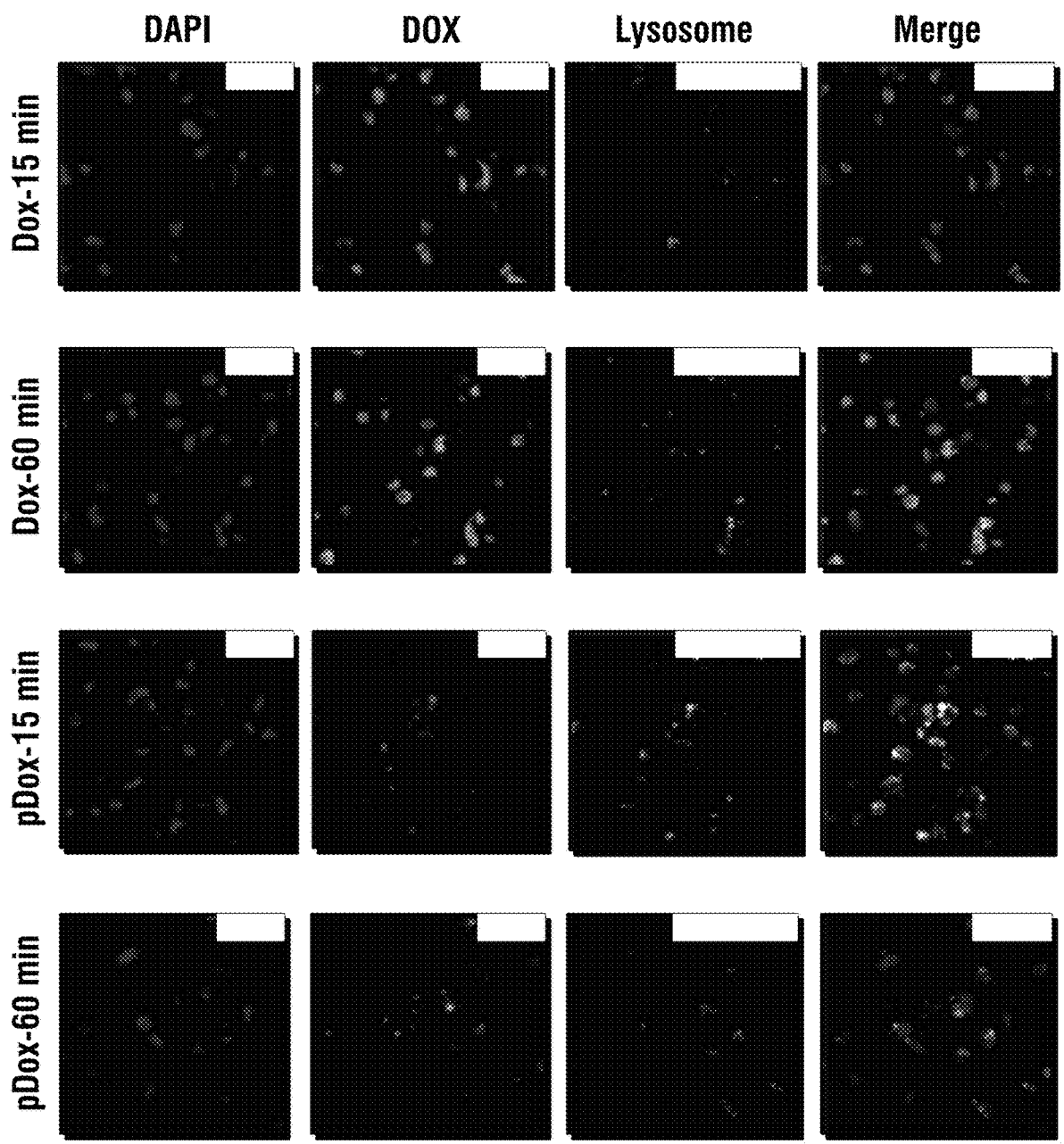

Vesicular Transport and pH-Dependent Release of pDox is Important for Overcoming Multidrug Resistance and for the Cell-Killing Activity of pDox Applicants conducted studies to compare cellular uptake and subcellular trafficking of free Dox and pDox nanoparticles in MDA-MB-231 cells. Free Dox entered the tumor cells through passive diffusion and accumulated in the nucleus 15 minutes after addition of the drug (FIG. 2A). However, no nuclear accumulation was detected in the pDox-treated cells at the same time (FIG. 2A and FIG. 2D). The red fluorescence from pDox could be co-localized with the green LysoTracker-positive subcellular organelles beginning at 15 minutes, and reached a high level one hour after pDox treatment (FIG. 2A and FIG. 2D), indicating pDox entered tumor cells via vesicular transport. In the acidic environment of late endosomes/lysosomes, pDox disassembled into Dox and poly-glutamic acid (FIG. 1B), and the released Dox likely entered the nucleus directly from the perinuclear compartments. After prolonged incubation for 12 hours, less co-localization between pDox and LysoTracker could be detected (FIG. 2A), suggesting the majority of disassembled Dox molecules had exited the late endosomes/lysosomes. It was also possible; however, that pDox accumulation in the late endosomes/lysosomes had damaged these subcellular organelles, since LysoTracker-positive signals were also detected to a lesser extent (FIG. 2A). Nuclear localization of disassembled Dox could be spotted 12 hours after pDox treatment, although most Dox signals could still be found outside of the nucleus (FIG. 2A). Thus, delay of nuclear entry by disassembled Dox likely account for slightly less cytotoxicity from treatment with pDox and MSV/pDox, compared to free Dox (FIGS. 1F, 1G, and 1H).

Figure 2E:
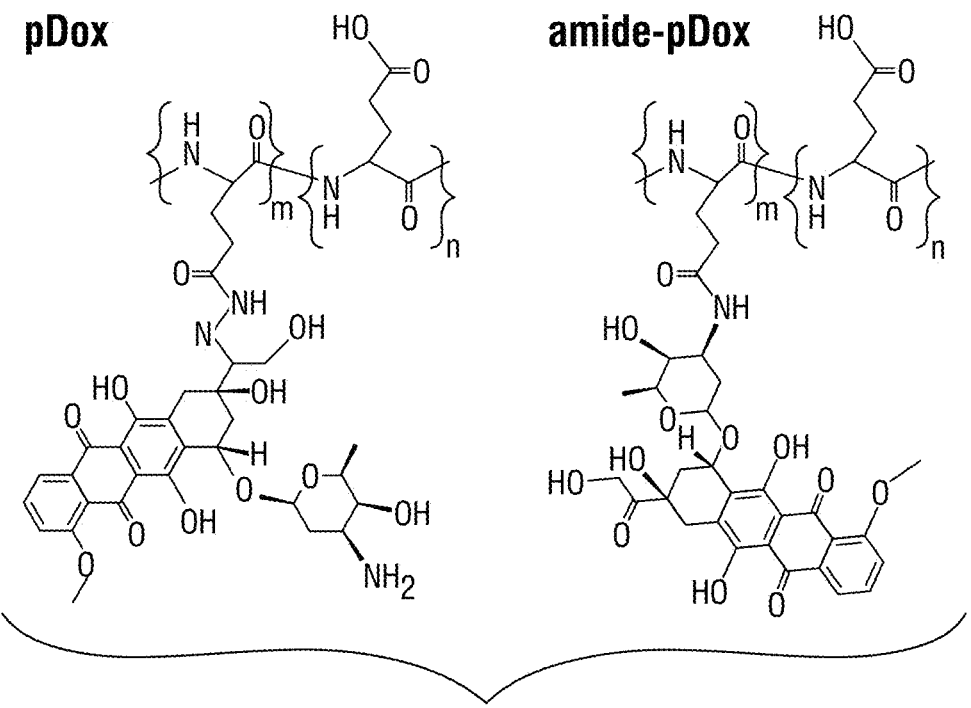
Figure 2F:
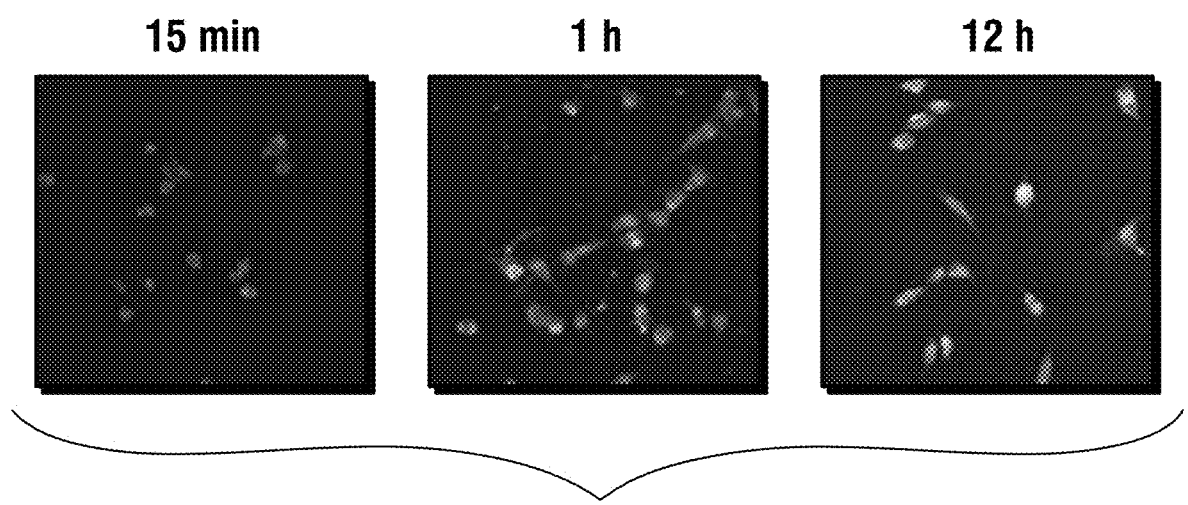
Figure 2G:
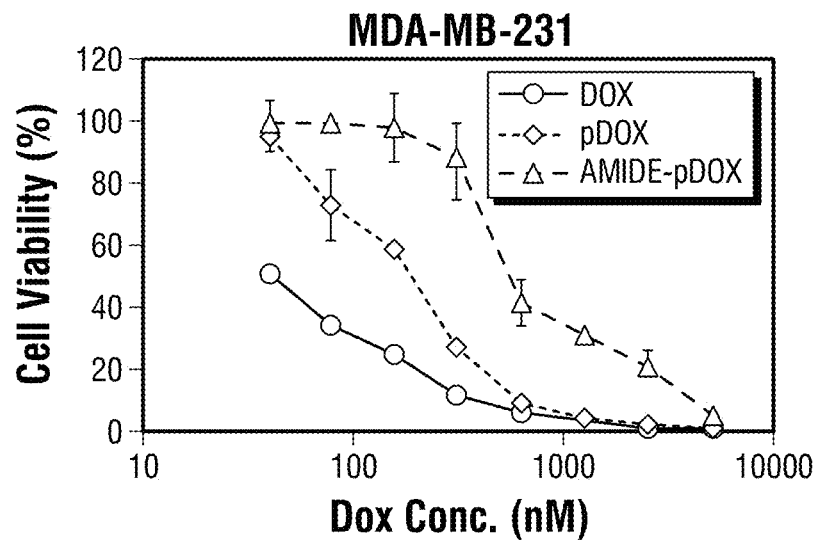
Figure 2H:
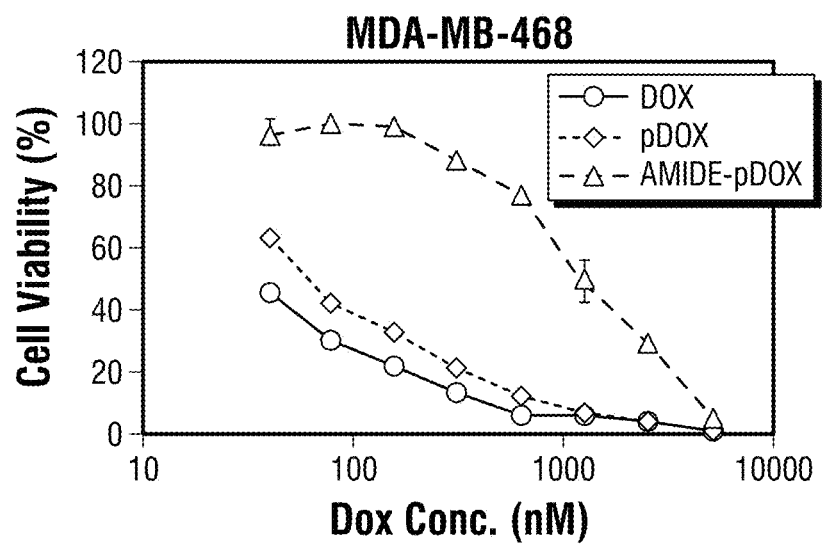

To evaluate whether pH-dependent Dox release from pDox was critical for cell killing activity, Applicants synthesized amide-pDox, which shares a similar chemical structure as pDox, but lacks a hydrazone linker between poly(L-glutamic acid) and doxorubicin (FIG. 2E). Similar to pDox, amide-pDox entered tumor cells via vesicular transport (FIG. 2F). However, amide-pDox was only 10-25% as effective as pDox in killing MDA-MB231 and MDA-MB-468 cells (FIG. 2G and FIG. 2H).

Many breast cancer patients are resistant to chemotherapy due to drug efflux. About 25-50% of previously untreated breast cancers express the MDR1 gene encoding p-glycoprotein, one of the drug efflux pump proteins[17]. Overexpression of MDR1 has also been attributed to acquired resistance to anthracyclines and cross-resistance to other chemotherapy drugs in the clinic[15]. Since pDox is transported through the vesicular route and is disassembled at the perinuclear region, circumventing passive diffusion through the cytoplasmic membrane where the efflux pump proteins is located, Porous silicon/pDox might offer a significant benefit on killing of cancer cells that are normally resistant to chemotherapy. To test this hypothesis, Applicants introduced the MDR1 gene into MDA-MB-231 cells (MDA-MB-231/MDR). Overexpression of P-gp, confirmed by Western blot analysis (FIG. 2B), rendered MDA-MB-231/MDR cells resistant to treatment with free Dox, but not to pDox (FIG. 2C).

Example 9

Improved Therapeutic Efficacy on Mouse Model of Breast Cancer Lung Metastasis

Figure 3A:
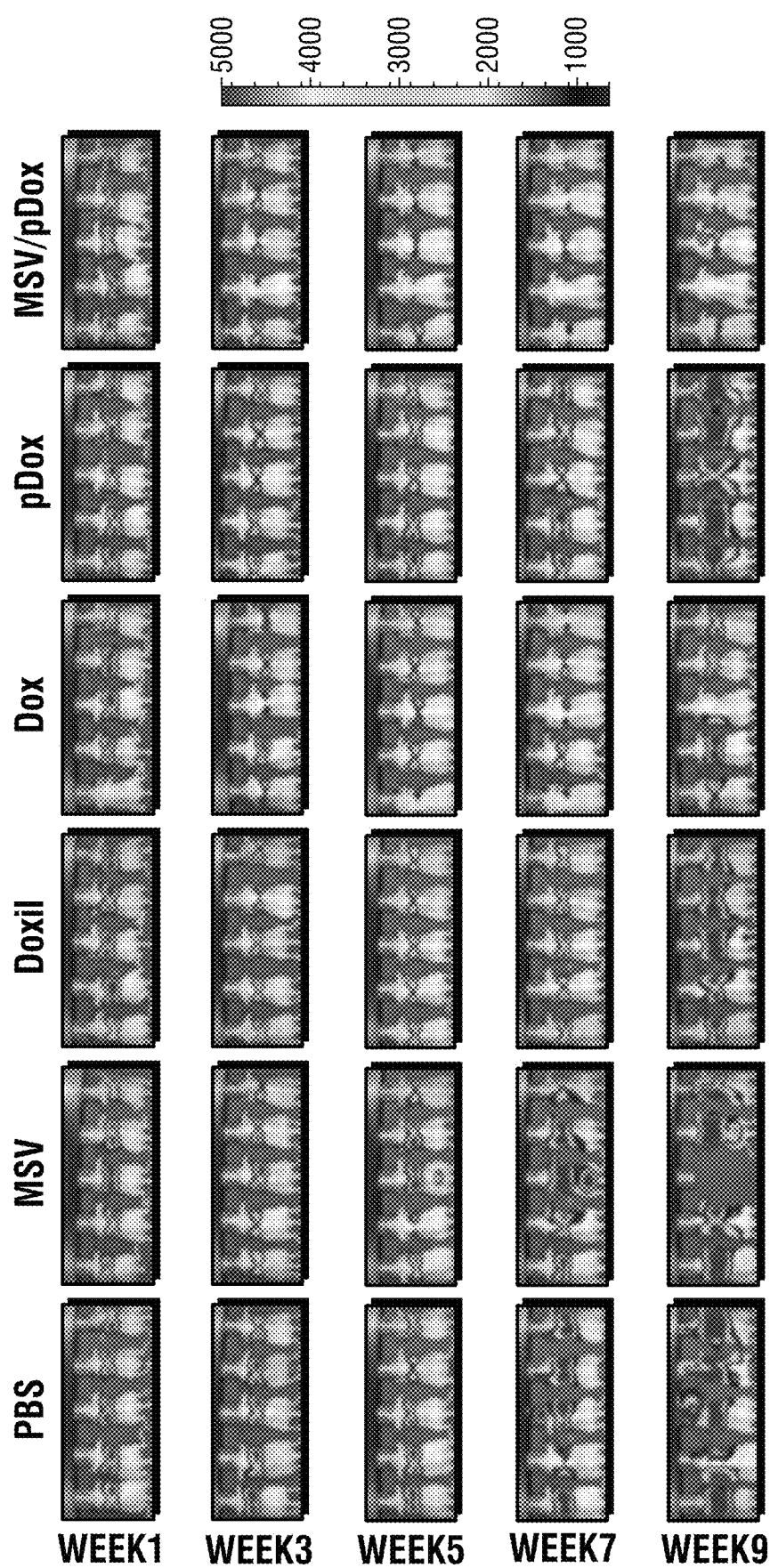
FIGS. 3A-3D show improved therapeutic efficacy by the porous silicon/pDox composition over Dox and Doxil in mouse models of breast cancer lung metastasis established by tail vein inoculation of MDA-MB-231 cells engineered with luciferase expression into nude mice. Tumor mice were treated weekly with 3 mg/kg free Dox, or biweekly with 6 mg/kg Doxil, pDox, or porous silicon/pDox for 6 weeks (n=10 mice/treatment group). Tumor growth was monitored by bioluminescent intensity based on luciferase activity. Images of representative five mice per group are shown (FIG. 3A). Long-term inhibition of tumor growth in the lung was observed in the Porous silicon/pDox treatment group.
Figure 3B:
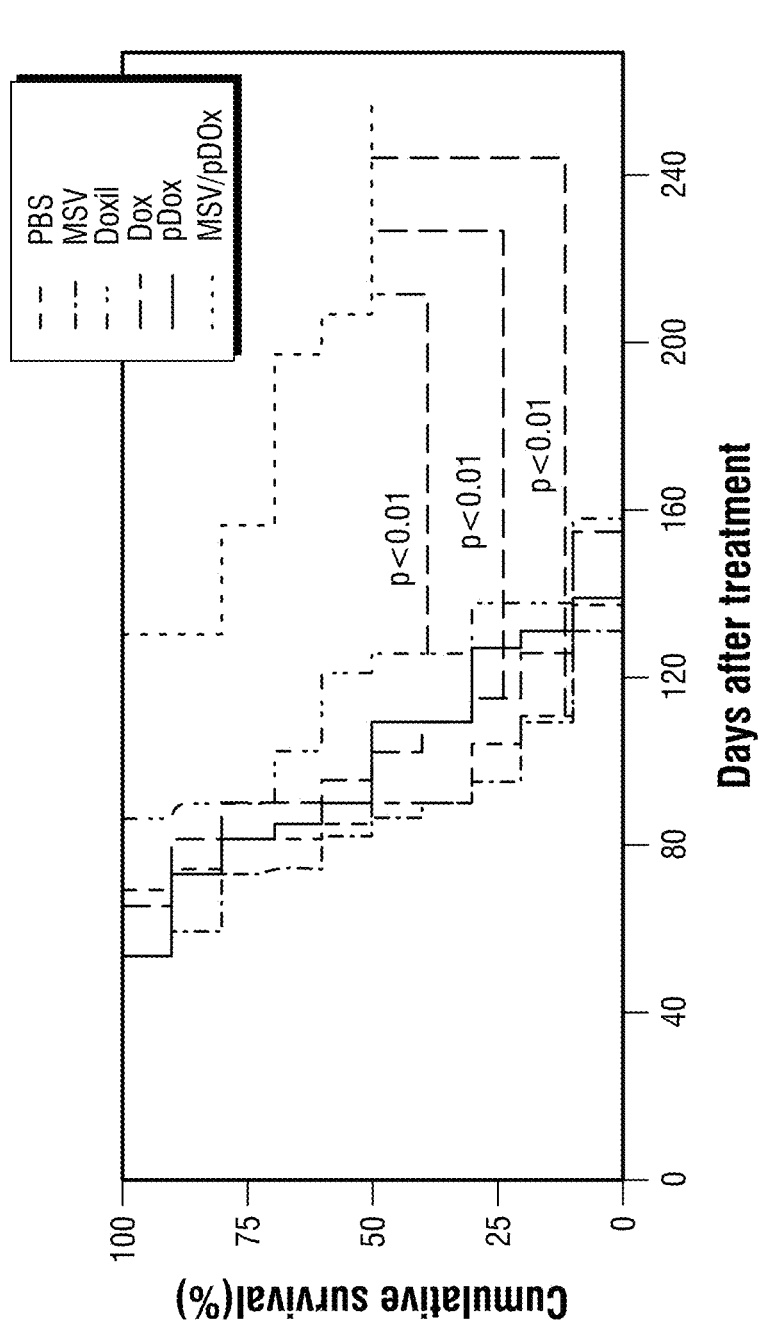
Figure 3C:
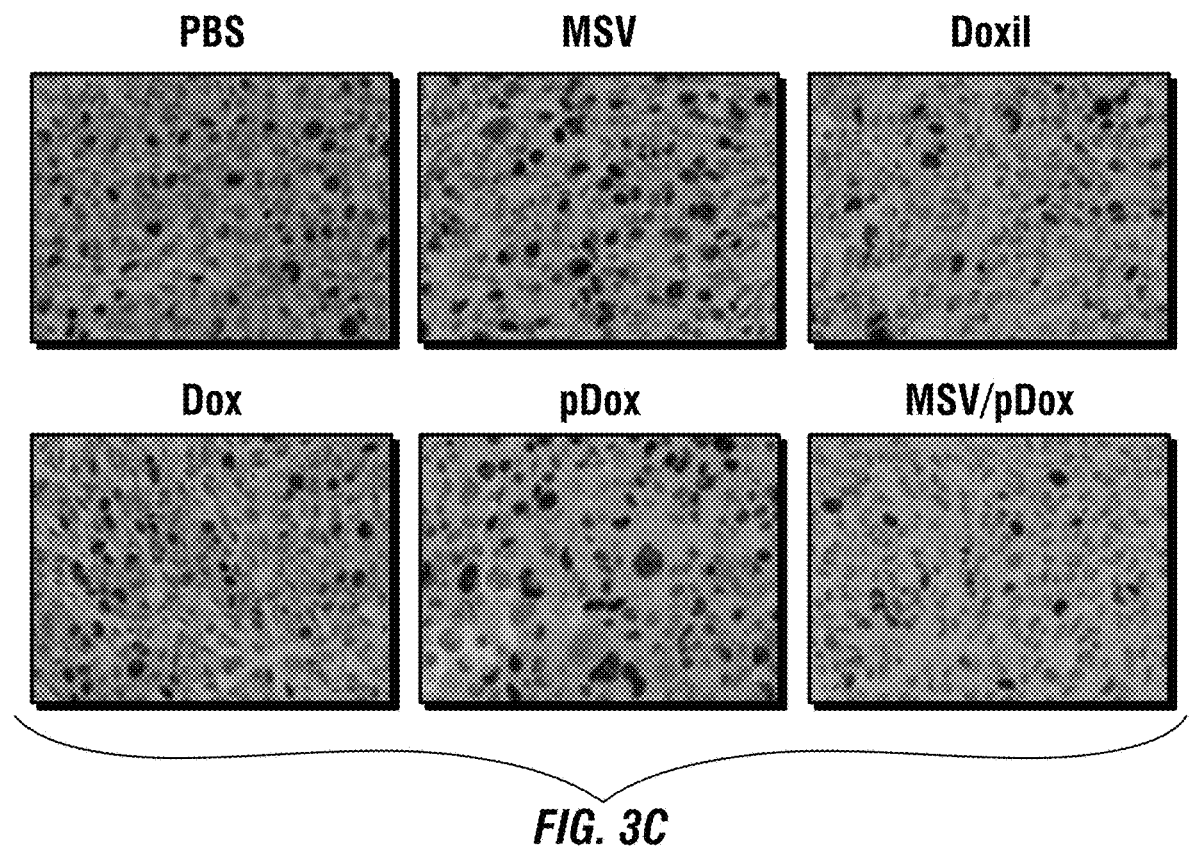
Figure 3D:
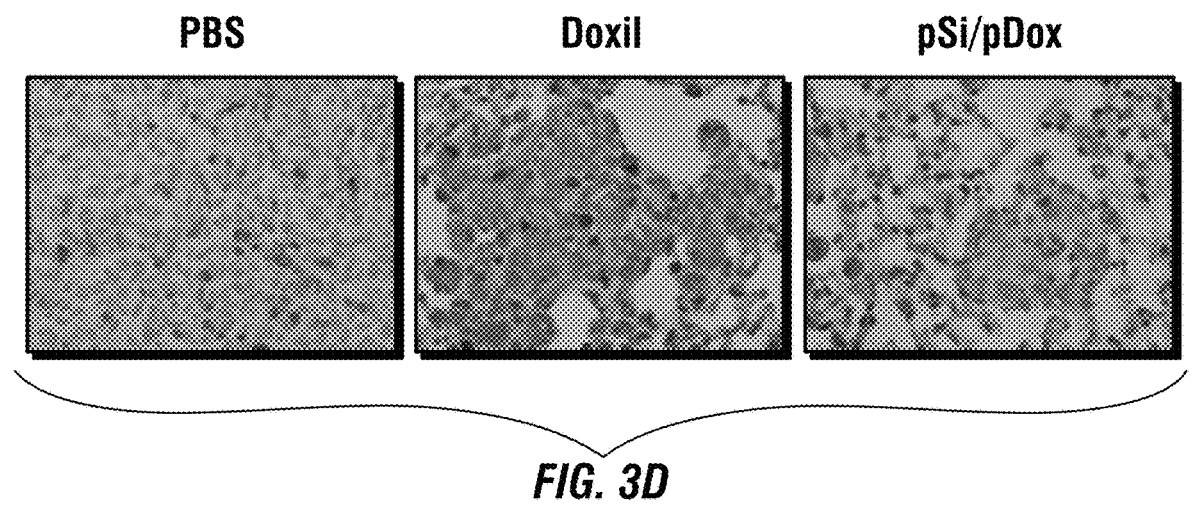
Figure 4A:
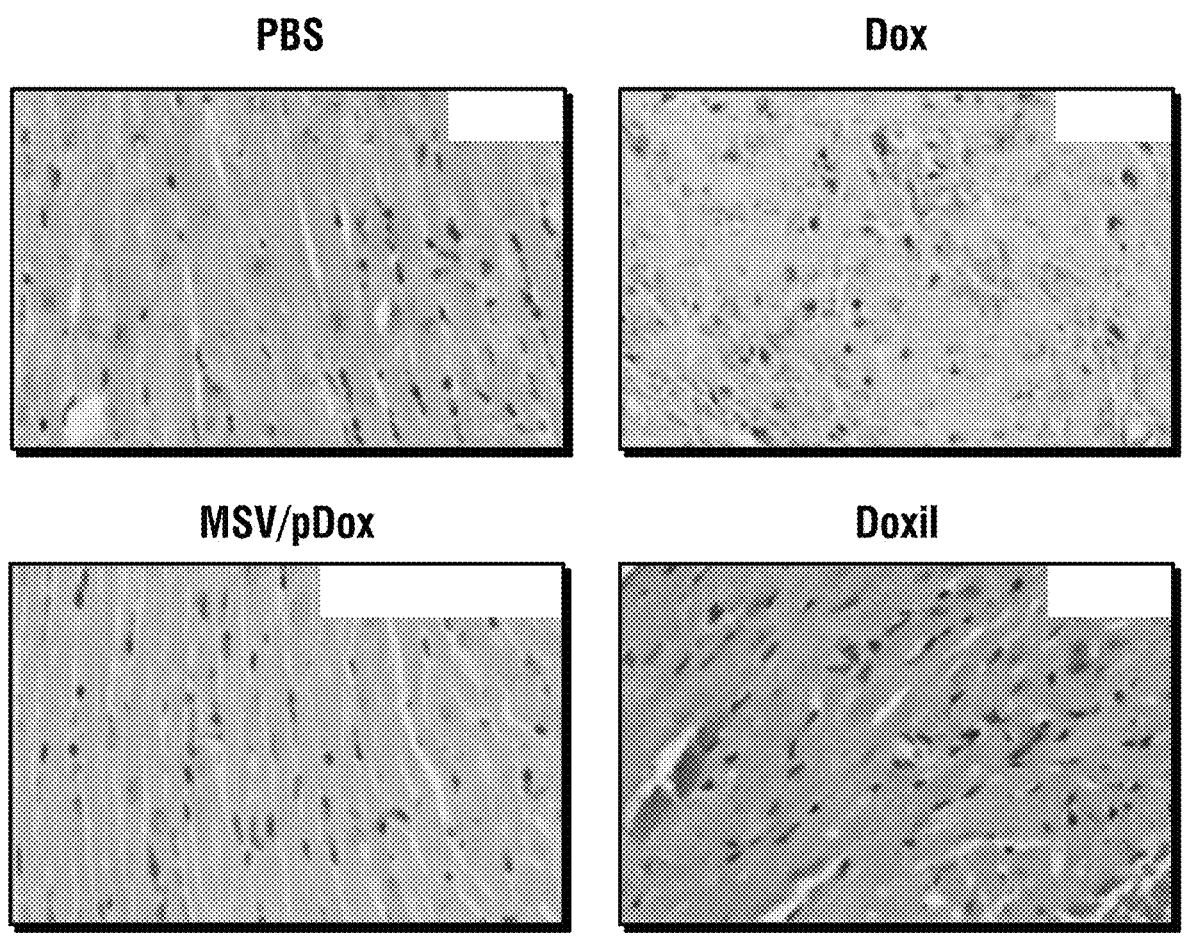
FIGS. 4A-4C show H&E staining of heart tissues in mice treated with 6 mg/kg free Dox, Doxil, or porous silicon/pDox for 6 weeks. Severe myocardial fiber damage was observed in mice treated with free Dox (FIG. 4A) and erythrocyte infiltration was apparent in the Doxil treated mice.
Figure 4B:
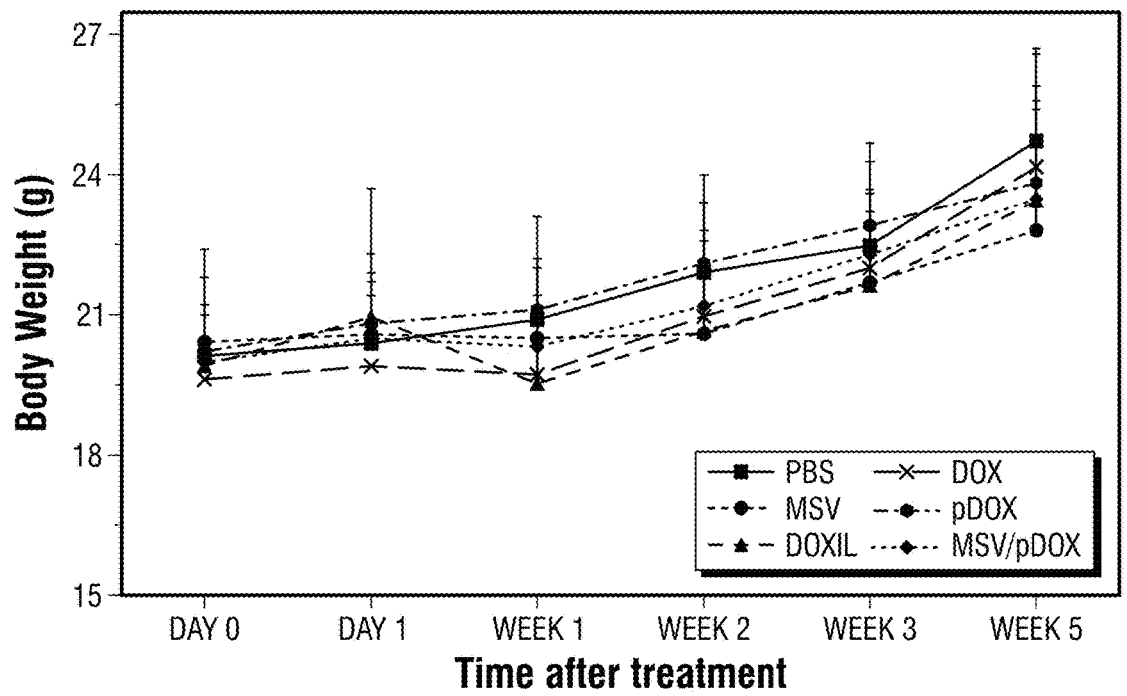

Applicants selected the murine model of MDA-MB-231 human breast cancer lung metastasis, widely used to study mechanism of pathology and for drug development[37-39], to evaluate therapeutic efficacy of porous silicon/pDox. Tumor growth in the lung was monitored by tracking bioluminescence for MDA-MB-231 cells that were engineered to exhibit luciferase activity and green fluorescent protein (GFP) (FIG. 3). Applicants treated the tumor-bearing mice with free pDox, porous silicon/pDox, and the clinically available drugs doxorubicin and Doxil, beginning one week after tumor inoculation and lasting for 6 weeks. Drugs were dosed biweekly at 6 mg/kg to mice in all treatment groups (10 mice per group) except free Dox. In a preliminary study, Dox treatment at 6 mg/kg biweekly caused deformation of myocardial fibers in the post-treatment mice, indicating severe cardiac toxicity (FIG. 4A). In subsequent animal studies, Applicants therefore administered Dox at 3 mg/kg weekly. The animals exhibited an initial drop in body weight but recovered shortly (FIG. 4B). Doxil treatment caused infiltration of erythrocytes into myocardial fibers in some animals and an initial drop in body weight (FIGS. 4A and 4B). No such effects were observed in animals treated with porous silicon/pDox, suggesting a more ideal safety profile than those of Dox or Doxil treatment. Animals treated only with PBS or empty MSV (control groups) started succumbing in week 9 and were lost completely by week 20, with a median survival time of about 12 weeks (FIGS. 3A and 3B). Treatment with Dox or pDox extended median survival by an additional 2 weeks (FIG. 3B). Although tumor growth (i.e., spread of bioluminescent signal) was slower in Dox-treated, but not pDox-treated, animals, no survival benefit was observed as a result (FIG. 3A). Mice in the Dox group most likely died from a combination of tumor growth and drug-related cardiac damage (FIG. 4A). In contrast to these two groups, animals treated with Doxil received superior therapeutic benefit, showing a median survival of 123 days (FIG. 3B). During the 6-week treatment period with Doxil, a stall in tumor growth tumor that resumed as soon as treatment discontinued was observed (FIG. 3A). The most striking survival advantage was observed when mice were treated with porous silicon/pDox (FIG. 3B). Eighty percent of the mice in this group remained viable even after 24 weeks, when all animals in the other treatment groups had succumbed to cancer, demonstrating its superior therapeutic efficacy.

TABLE 1

Median survival time of mice after treatment

| | Groups | | | | | |
|---|---|---|---|---|---|---|
| | PBS | MSV | Doxil | Dox | pDox | MSV/pDox |
| Median survival (Days) | 87 | 84 | 123.5 | 98.5 | 99.5 | 213 |

Figure 4C:
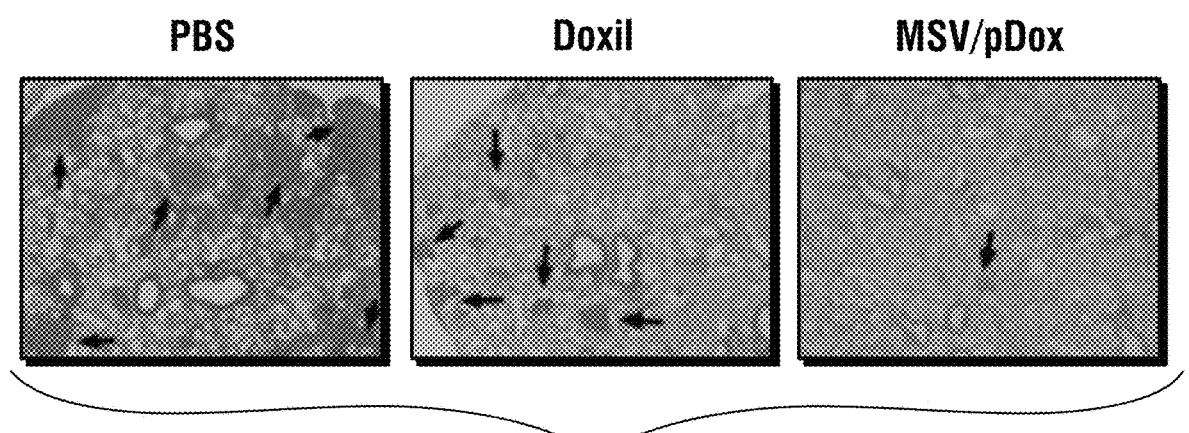

Hematoxylin and eosin (H&E) staining of the lung tissues from mice sacrificed at week 6 revealed smaller tumor nodules in those treated with Doxil or Porous silicon/pDox compared to PBS control (FIG. 4C). The difference was reflected by Ki-67 staining for proliferating tumor cells in post-treatment lung tissues (FIG. 3C). While there were many Ki-67-positive cells in the PBS and empty porous silicon treated control groups, there were much less stain-positive cells in Doxil-treated and even less in porous silicon/pDox-treated mice. Without being bound by theory, a possible explanation for these results is that a greater drug amount was delivered to the tumor tissues with porous silicon/pDox than with free pDox or Doxil.

Example 10

Acquired Resistance in Doxil-Treated Mice

To explore the underlying mechanism for the huge improvement on therapeutic efficacy of pDox over Doxorubicin, MDA-MB-231 cancer cells expressing the MDR1 gene (FIGS. 2B and 2C), were treated with pDOX and Doxorubicin to compare growth inhibition mediated by each. The cells were sensitive to pDox, but resistant to treatment with free Dox (FIG. 2C). MDR1 overexpression has been attributed to acquired resistance to anthracyclines and cross-resistance to other chemotherapy drugs in the clinic (Fojo and Menefee 2007). Patients with overexpressed P-gp, the protein product of MDR1, have few options left for the choice of chemotherapy drugs. P-gp overexpression might have contributed significantly to therapy resistance during Doxil treatment and a sudden burst of post-treatment tumor growth (FIG. 3A).

Example 11

Inhibition of Lung Metastasis in Murine Syngeneic Mammary Gland Tumor Mice

The murine 4T1 mammary gland tumor cells do not express ER, PR and HER2. Thus the 4T1 syngeneic tumor mice represent a second Triple Negative Breast Cancer (TNBC) tumor model in this study. When inoculated into the mammary gland fat pad of BALB/c mice, 4T1 tumor cells formed rapidly growing primary tumors. If left untreated, all of the mice would eventually develop lung metastasis from primary tumors. In a pilot study, surgical removal of primary tumors (about 400 mm$^3$ in size) was performed, and then PBS, Dox, pDox, or Porous silicon/pDox was administered once immediately after surgery and again 10 days post-surgery. Since mice treated with PBS exhibited signs of illness by week 5, mice in all treatment groups were sacrificed by week 6 and examined for lung tumor nodules. On average, mice treated with either PBS, Dox, or pDox developed multiple, large tumor nodules in the lung (FIG. 5D). Similar to the observation with the MDA-MB-231 tumor mouse model, the group treated with Porous silicon/pDox presented with much less tumor metastasis.

TABLE 2

Median survival time of mice after tumor inoculation

| | Groups | | | | | |
|---|---|---|---|---|---|---|
| | PBS | MSV | Doxil | Dox | pDox | MSV/pDox |
| Median survival(Days) | 51 | 54.5 | 70 | 62 | 57.5 | 98 |

However, the 4T1 tumors appeared more resistant to therapy (i.e., Porous silicon/pDox treatment), since the presence of small tumor nodules in the lungs after two rounds of Porous silicon/pDox administration was observed. These tumor nodules were noticeably smaller in size and number compared to those treated with PBS, Dox, or and pDox (FIG. 5E). Remarkably, Porous silicon/pDox particles could still be detected in tumor tissues 6 days post treatment (FIGS. 5F-1 and 5F-2), demonstrating drug enrichment and sustained release of pDox from MSV in tumor tissues. To evaluate drug dosing requirements and sustainability after administration, Applicants applied a different drug regimen to BALB/c mice bearing 4T1 tumors. Applicants performed complete surgical removal of the primary tumors once they reached 250-300 mm3, and confirmed that the extraction was thorough by the lack of bioluminescence from the luciferase- and GFP-bearing mammary gland fat pads (FIG. 5A). Dox, Doxil, pDox, or Porous silicon/pDox was then administered weekly for 4 weeks following surgery to assess lung metastasis and survival benefit due to treatments. A significant variation in latency of tumor development was observed (i.e., bioluminescence in the chest area) (FIG. 5A). Mice treated with PBS or MSV alone began to die of lung metastasis in week 6 (FIG. 5A), and all of them had succumbed to tumor over-growth by week 9 (FIG. 5A). pDox offered limited survival benefit. Treatment with free Dox and Doxil extended median survival by 13 and 19 days over the PBS control respectively (FIG. 5B). Most strikingly, little to no traces of bioluminescence in animals treated with Porous silicon/pDox4 weeks post-surgery were observed (FIG. 5A, bottom panel), and about 40% of the animals survived over 160 days, i.e., long after the treatments were stopped (FIG. 5B), which is very comparable to that seen with the MDA-MB-231 model (FIG. 4). Histological analysis of tumor biopsies from mice in the different treatment groups revealed that Doxil and Porous silicon/pDox most significantly reduced cell proliferation (FIG. 5C). Mice treated with Porous silicon/pDox had the most extensive apoptosis/necrosis in tumor tissues revealed by TUNEL assay (Supplementary FIG. 5D). Thus, Applicants have demonstrated the superior therapeutic benefit of Porous silicon/pDox in two major murine TNBC tumor models.

Example 12

Porous Silicon/pDox Enriches Predominantly in Lung Tumors

To understand the mechanism of enhanced inhibition of breast cancer lung metastasis by MSV/pDox, free pDox and Porous silicon/pDox particle accumulation in tumor nodules was compared and concentration of disassembled Dox in major organs was measured. Particle accumulation in tumor nodules of MDA-MB-231 lung metastasis was monitored by tracking bioluminescence at 1 hour and 24 hours after dosing (i.v.). At both time points, particles accumulated much more readily in the lung tumor tissues of mice treated with Porous silicon/pDox (FIG. 6A). MSV particles had reached the edge of tumor nodules 1 hour after dosing, and clusters of particles inside the tumor tissues could be detected at the 24 hour time point (FIG. 6C), an observation that we corroborated using intravital microscopy (FIG. 6B). Tissue sectioning showed more pronounced tumor cell apoptosis (TUNEL assay, FIGS. 6E and H&E staining, FIG. 6F) in mice that were treated with Porous silicon/pDox24 hours post-dosing compared to those treated with free pDox or Doxil.

Figure 6D:
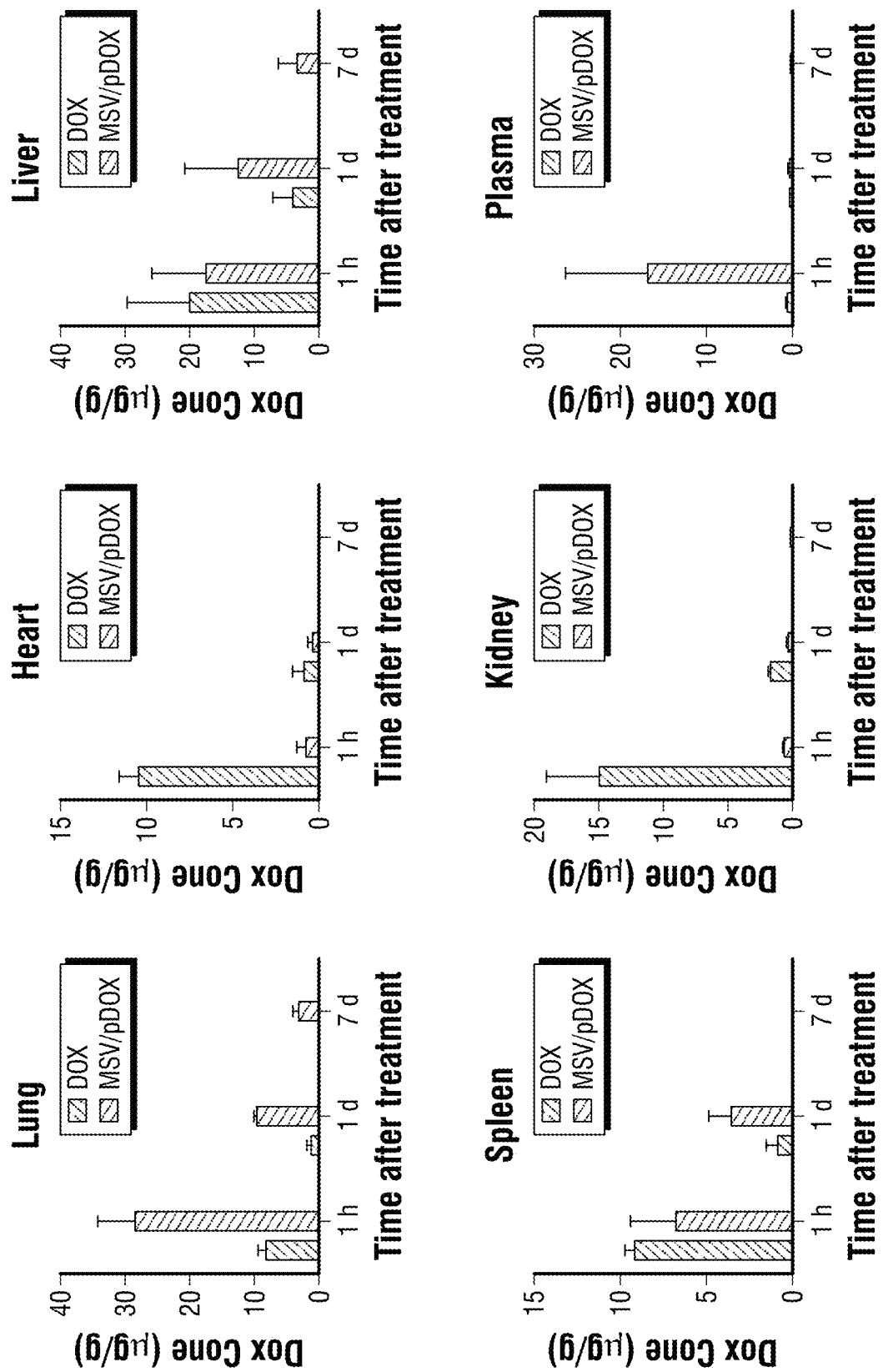
Figure 6E:
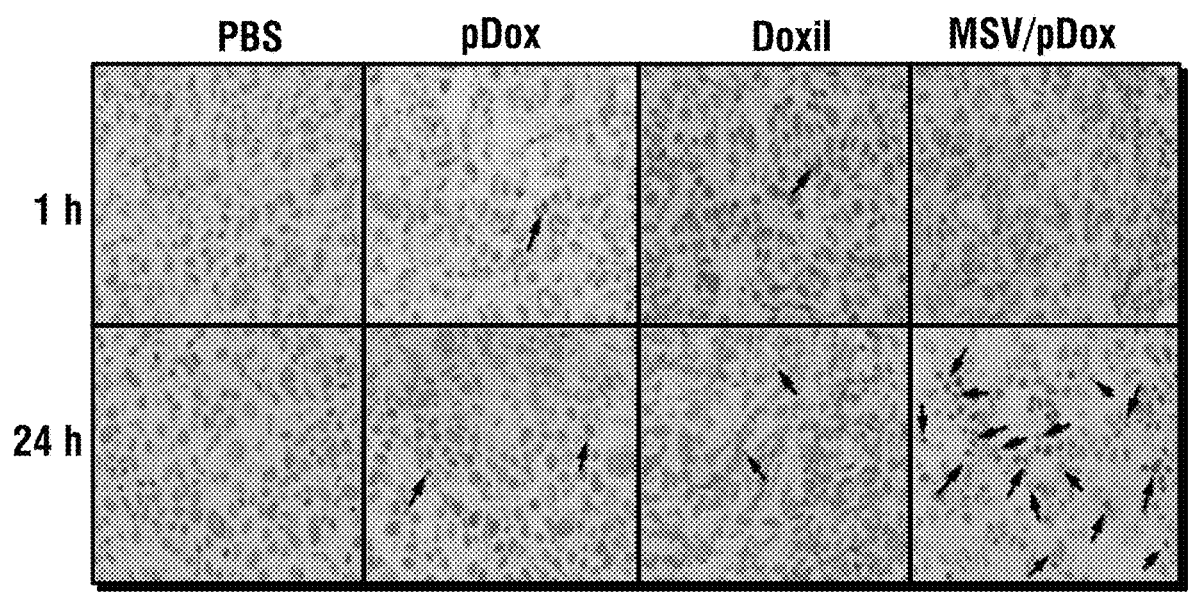
Figure 6F:
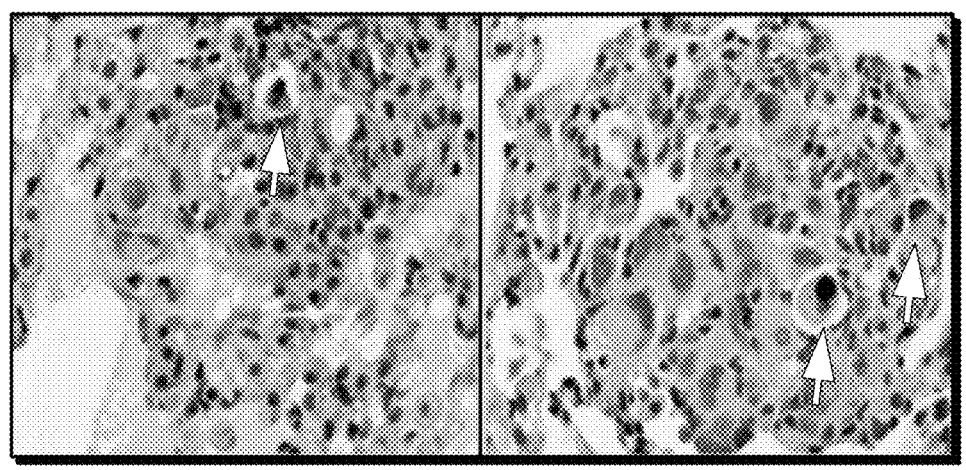

Next, the biodistribution of free Dox or Dox that had disassembled from Porous silicon/pDox (i.v. administration) at 1 hour, 1 day, and 7 days post-dosing in tumor-bearing mice was examined (FIG. 6D). Overall, high drug concentration of free Dox in the heart (over 10 μg/g organ) one hour after dosing was detected. In contrast, disassembled Dox (from Porous silicon/pDox) did not enrich in the heart (below 1 μg/g organ), correlating with the lack of cardiac structural damage in Porous silicon/pDox-treated mice (FIG. 4A). No significant difference in drug accumulation in the liver and spleen one hour post-dosing between these two groups was detected. However, significant concentrations of drug could be detected in the liver and spleen 1 day post-dosing and even 7 days post dosing (in the liver). The most consistent and prominent contrast in drug accumulation could be seen in the lung profile. Applicants found 3 times the amount of Dox released from Porous silicon/pDox than free Dox in the lung 1 hour after dosing, and high levels of disassembled Dox in the Porous silicon/pDox-treated mice maintained in the lung even up to 7 days post-dosing. These data indicate that Porous silicon/pDox accumulated favorably in the lung and that sustained release of drug from the MSV could ensure high local drug concentration for an extended time period. On the other hand, plasma clearance of both Dox and Porous silicon/pDox was very rapid (FIG. 6D, last panel). A high level of plasma Dox from the Porous silicon/pDox-treated mice 1 hour post-dosing was detected as compared to a trace amount 1 day post-dosing. Plasma Dox was already barely detectable 1 hour post-dosing in the free Dox-treated mice (FIG. 6D). These results suggest that favorable tissue accumulation and sustained release of the active drug must likely contributed to enhanced therapeutic efficacy of Porous silicon/pDox in both the MDA-MB-231 and 4T1 tumor model studies (FIGS. 4 and 5).

Example 13

Overcoming Intrinsic Resistance by Inhibiting TICs

One drawback of using Dox is the potential for cells to acquire resistance to therapy. To help design strategies that circumvent this challenge, MDA-MB-231 cells were isolated from lung tumor nodules of mice given different treatment options for in vitro analysis. Due to technical considerations, cells from mice treated with PBS control or Doxil were isolated, since tumor nodules were smaller and scarcer in mice treated with Porous silicon/pDox (FIG. 4C). The isolated tumor cells from Doxil-treated mice exhibited more resistance to in vitro treatment with Dox than those tumor cells obtained from PBS-treated mice (FIG. 7A). Additionally, those cells from the former treatment group presented reduced expression of E-cadherin, a biomarker for epithelial cells (FIG. 7B). Conversely, expression of the mesenchymal cell biomarker N-cadherin was up-regulated in 2 of the 3 tumor samples (FIG. 7B). These results indicate a shift from epithelial to mesenchymal cell characteristics in the post-treatment tumor cells that may contribute to therapy resistance.

Another way to study the in-culture transition of cells taken from tumor biopsies, we examined the ability of $CD44^+/CD24^{-/low}$ subpopulation of tumor cells to form mammospheres, measured by what is known as the mammosphere formation efficiency (MSFE). Although other progenitor cells in the tissues are also involved in forming primary mammospheres, only the $CD44^+/CD24^{-/low}$ cells with self-renewal potential can form secondary mammospheres from primary mammosphere-derived single cells[40]. Results from these experiments first showed no significant difference in primary mammosphere formation among the treatment groups (i.e., PBS, Doxil, or Porous silicon/pDox) (FIG. 8A). However, after seeding cells from the primary mammospheres to examine secondary mammosphere formation, a higher secondary MSFE was observed in cells taken from tumors originally treated with Doxil, compared to those given only PBS (FIG. 7C). This result correlated with our previous finding that $CD44^+/CD24^{-/low}$ cells were enriched in cancer patients post-chemotherapy[41]. Unexpectedly, Applicants saw an even more dramatic reduction in secondary MSFE in cells taken from Porous silicon/pDox-treated tumors (FIG. 7C). Indeed, when the mammospheres were visualized via green fluorescence from GFP, the mammospheres formed by cells derived from Porous silicon/pDox-treated tumors presented in smaller size and number (FIG. 7D).

Figure 7E:
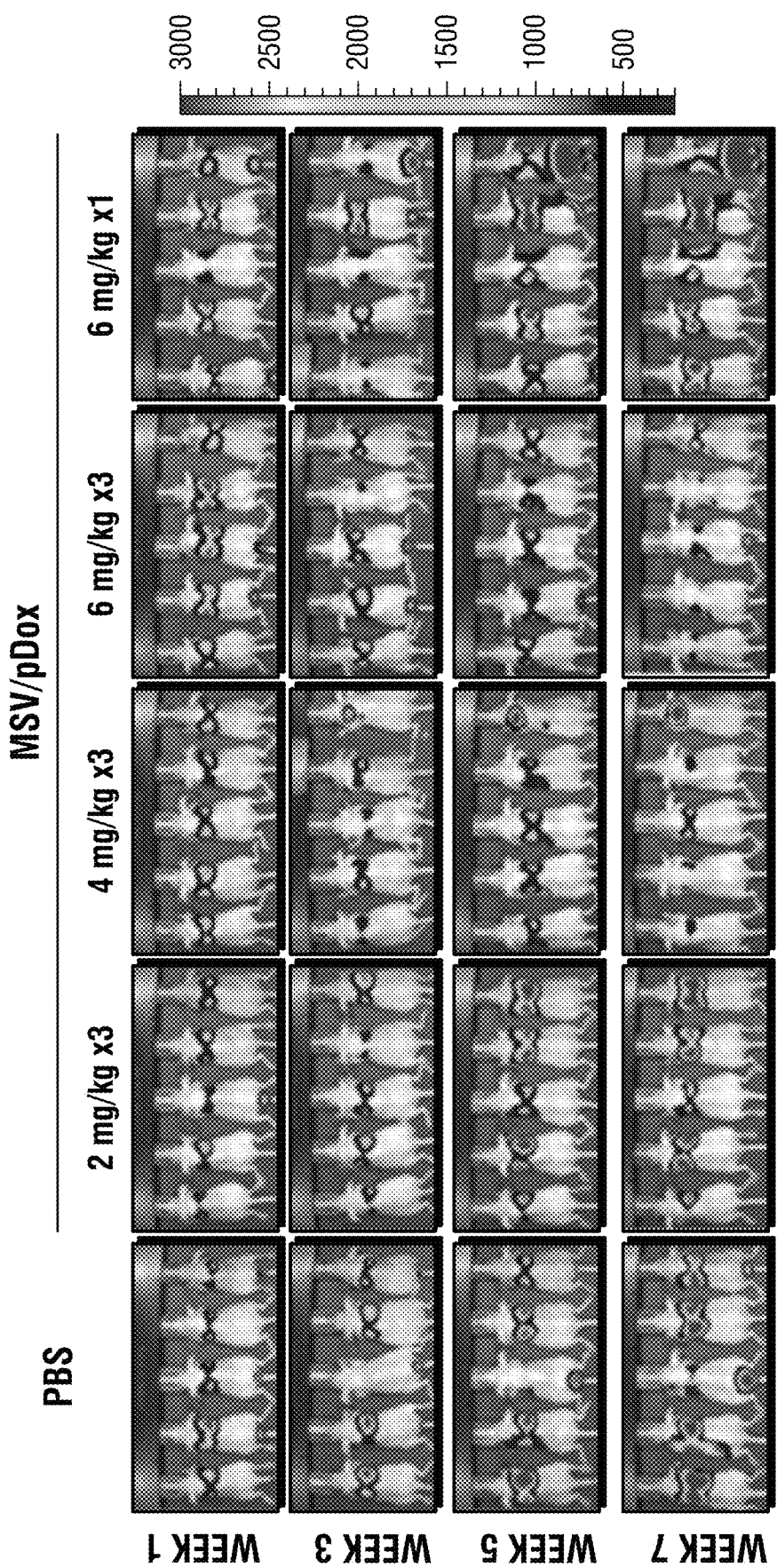
Figure 7F:
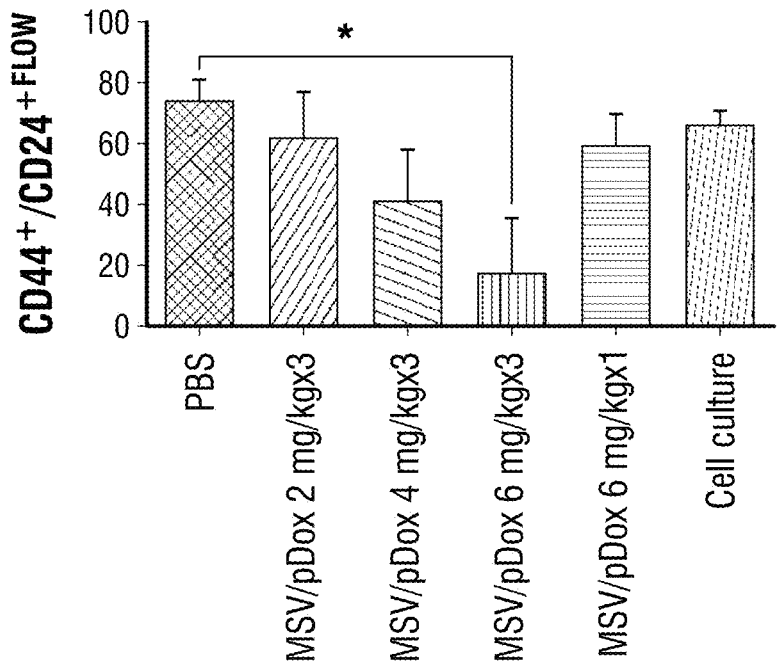
Figure 7G:
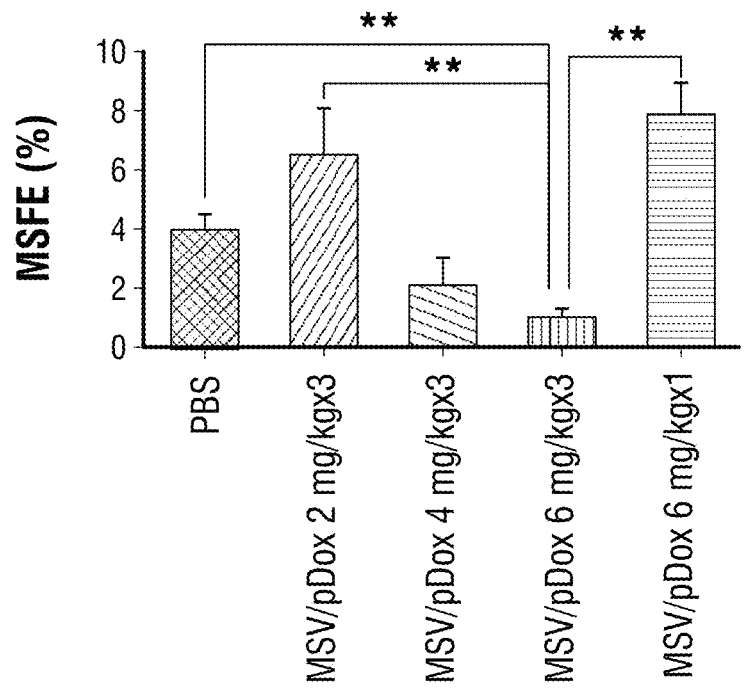
Figure 9A:
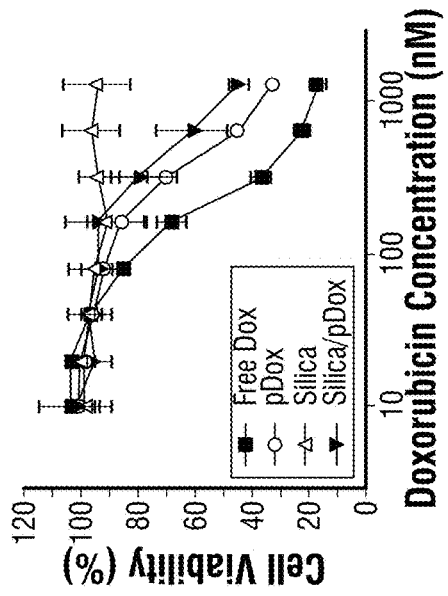
FIGS. 9A-9D show MTT assay for cytotoxicity from free Dox, pDox, and porous silica/pDox on MDA-MB-231 (FIGS. 9A and 9B) and Hs578t cells (FIGS. 9C and 9D) following 48 and 72 hours of treatment.
Figure 9C:
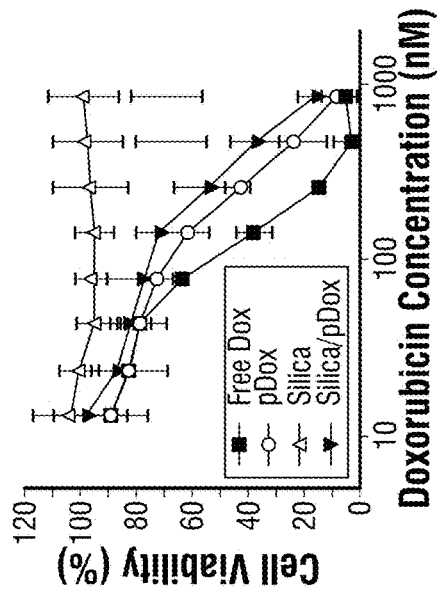
Figure 9B:
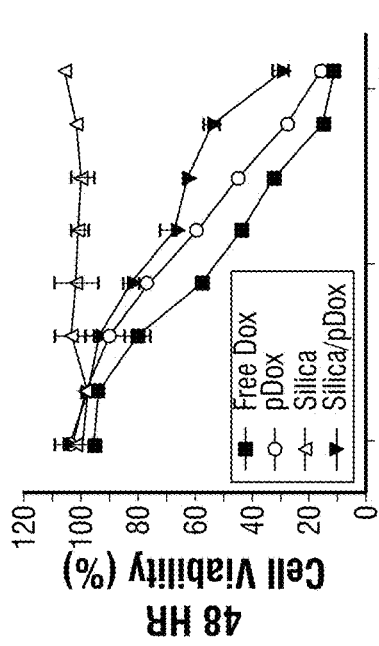
Figure 9D:
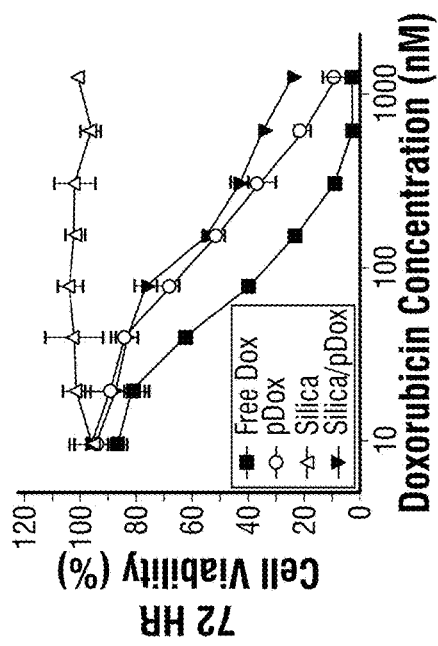
Figure 10A:
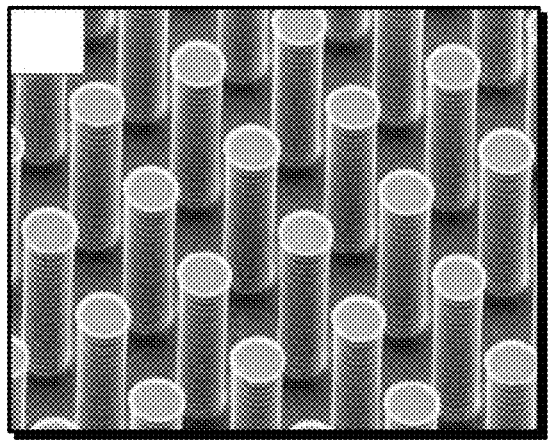
FIGS. 10A-10D show multilayer production of discoidal porous silicon particles. SEM image of silicon pillars formed by lithography and deep silicon etch (FIG. 10A). Multilayer particle stack produced by programmed electrochemical etch of silicon pillars (FIG. 10B). Released particle stacks (FIG. 10C). Monodisperse porous silicon particles after ultrasound treatment of the particle stacks (FIG. 10D).
Figure 10B:
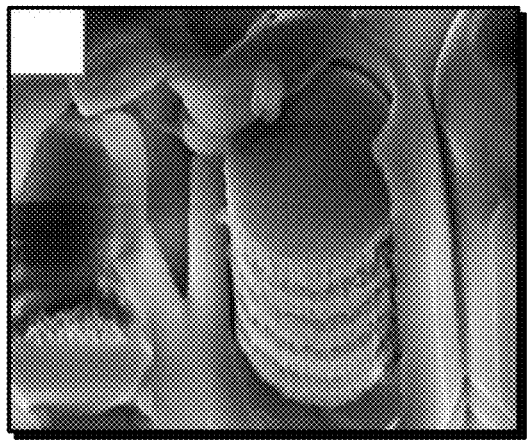
Figure 10C:
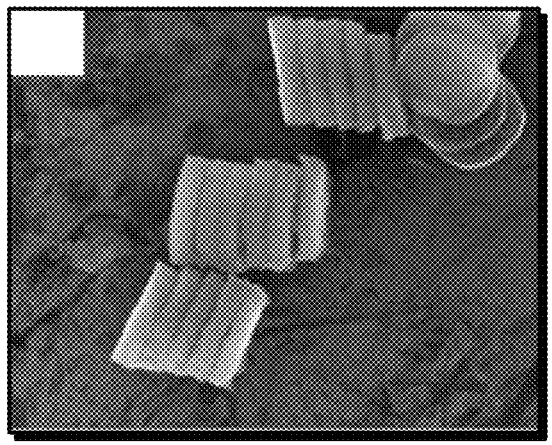
Figure 10D:
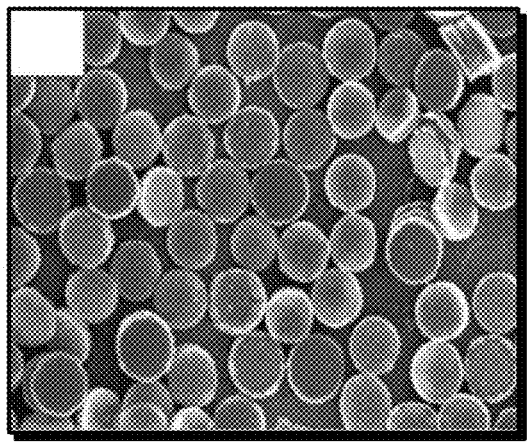

To further explore the response of $CD44^+/CD24^{-/low}$ cells to Porous silicon/pDox, tumor-bearing mice were treated for 6 weeks with varying amounts of Porous silicon/pDox. During this time, lung tumor spread was monitored by tracking in vivo bioluminescence and observed a dose-dependent improvement in therapeutic efficacy (FIG. 7E) that was best achieved with 3 treatments of 6 mg/kg Porous silicon/pDox. Even a high dosage, 6 mg/kg treatment administered only once was insufficient to inhibit tumor growth (FIG. 7E). Once treatment concluded, lung tumor tissue extractions were conducted for mammosphere formation analysis. The percentage of $CD44^+/CD24^{-/low}$ cells from the primary mammospheres by flow cytometry was also determined. On average, cultured MDA-MB-231 cells or those extracted from tumors were enriched with $CD44^+/CD24^{-/low}$ cells. This cell population remained high in the PBS control and 2 mg/kg-treatment groups, but dropped 30% when Porous silicon/pDox dosing doubled to 4 mg/kg, and an additional 20% to the lowest level at 6 mg/kg-dosing (FIG. 7F). As expected, one treatment with 6 mg/kg Porous silicon/pDox did not cause a significant reduction in the percentage of $CD44^+/CD24^{-/low}$ cells or the number of secondary mammospheres (FIG. 7G). Tumor cells from the 6-week treatment groups exhibited a dose-dependent reduction of MSFE that correlated with changes in $CD44^+/CD24^{-/low}$ cell enrichment. Applicants could only find a few secondary mammospheres formed by cells extracted from the 6 mg/kg repeated treatment group (Supplementary FIG. 8B). It is intriguing that the percentages of $CD44^+/CD24^{-/low}$ cells were higher in samples cultured from the 2 mg/kg-Porous silicon/pDox repeated treatment and 6 mg/kg-Porous silicon/pDox single treatment groups than from the PBS control group.

To support the finding from the MDA-MB-231 tumor mice study, we analyzed tumor-initiating cells in the post-treatment 4T1 tumor mice. As with the MDA-MB-231 study, tumor cells were collected from the lung, and MSFE with the secondary mammospheres was evaluated. A significant drop both in total number and the size of the individual mammospheres was found in cells taken from Porous silicon/pDox-treated tumors (FIGS. 8C, 8D). Applicants also examined the expression of ALDH1, a tumor-initiating cell marker that predicts poor clinical outcome in breast cancer[40], in these tumor samples. The dramatic decrease of ALDH1-positive cells in Porous silicon/pDox-treated tumor correlated well with the reduction of MSFE (Supplementary FIG. 8E).

Collectively, these results indicate that both local Dox concentration and treatment duration were important determinants for effective elimination of $CD44^+/CD24^{-/low}$ cells in breast cancer lung metastasis.

Example 14

Killing of Human Breast Cancer Cells by Porous Silica/pDox

Human breast cancer cells, MDA-MB-231 and Hs578t, were seeded in 96-well plates at a density of 3,000 cells per well. Cells were treated with free Dox, pDox, porous silica, and porous silicon/pDox. Cell viability was measures by MTT assay 48 hours and 72 hours later. Comparable cytotoxicity was observed between pDox and porous silicon/pDox (FIGS. 9A-9D).

Example 15

Degradation of Porous Silicon Particles

Figures 1, 11A:
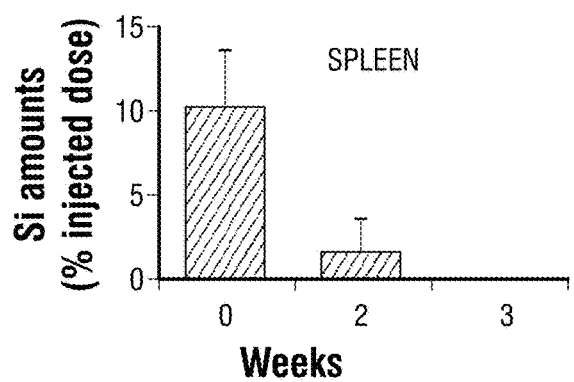
Figures 2, 11A:
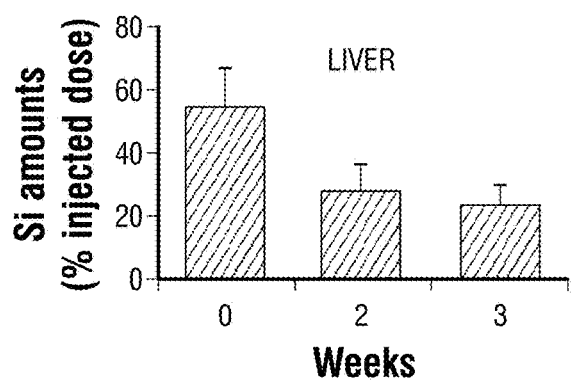
Figure 11B:
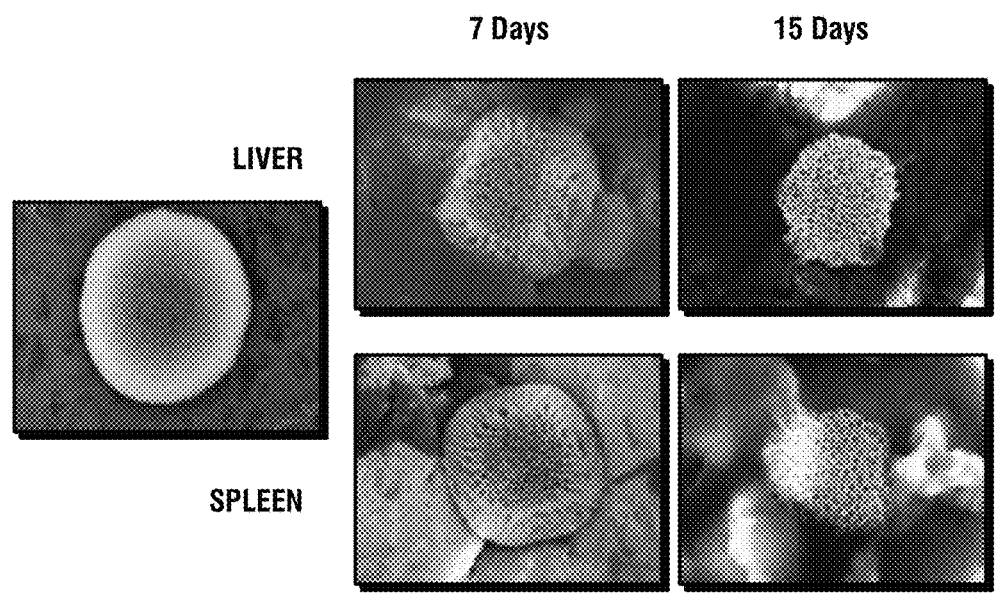

Mice were administered porous silicon particles by tail vein injection (n=9 mice/group) and total silicon content analysis in spleen and liver performed. Mice were euthanized after indicated time period (0, 2 weeks, and 3 weeks) post-administration and liver and spleen processed for silicon content analysis using Varian ICP optical emission spectrometer. Silicon content was expressed as percentage of injected dose (FIGS. 11A-1 and 11A-2). For SEM analysis, porous silicon particles were isolated from liver and spleen tissue homogenates, and further cleaned by sonication. SEM images show a time-dependent degradation on days 7 and 15 post-administration (FIG. 11B).

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

REFERENCES

1. Steeg, P. S. & Theodorescu, D. Metastasis: a therapeutic target for cancer. *Nat Clin Pract Oncol* 5, 206-219 (2008).
2. Hayes, D. F. et al. HER2 and response to paclitaxel in node-positive breast cancer. *N Engl J Med* 357, 1496-1506 (2007).
3. (EBCTCG), E.B.C.T.C.G. Effects of chemotherapy and hormonal therapy for early breast cancer on recurrence and 15-year survival: an overview of the randomised trials. *Lancet* 365, 1687-1717 (2005).
4. Von Hoff, D. D. et al. Risk factors for doxorubicin-induced congestive heart failure. *Ann Intern Med* 91, 710-717 (1979).
5. Zhang, S. et al. Identification of the molecular basis of doxorubicin-induced cardiotoxicity. *Nat Med* 18, 1639-1642 (2012).
6. Gabizon, A., Shmeeda, H. & Barenholz, Y. Pharmacokinetics of pegylated liposomal Doxorubicin: review of animal and human studies. *Clin Pharmacokinet* 42, 419-436 (2003).
7. O'Brien, M. E. et al. Reduced cardiotoxicity and comparable efficacy in a phase III trial of pegylated liposomal doxorubicin HCl (CAELYX/Doxil) versus conventional doxorubicin for first-line treatment of metastatic breast cancer. *Ann Oncol* 15, 440-449 (2004).
8. Harris, L. et al. Liposome-encapsulated doxorubicin compared with conventional doxorubicin in a randomized multicenter trial as first-line therapy of metastatic breast carcinoma. *Cancer* 94, 25-36 (2002).
9. Batist, G. et al. Reduced cardiotoxicity and preserved antitumor efficacy of liposome-encapsulated doxorubicin and cyclophosphamide compared with conventional doxorubicin and cyclophosphamide in a randomized, multicenter trial of metastatic breast cancer. *J Clin Oncol* 19, 1444-1454 (2001).
10. Longley, D. B. & Johnston, P. G. Molecular mechanisms of drug resistance. *J Pathol* 205, 275-292 (2005).
11. Epenetos, A. A., Snook, D., Durbin, H., Johnson, P. M. & Taylor-Papadimitriou, J. Limitations of radiolabeled monoclonal antibodies for localization of human neoplasms. *Cancer Res* 46, 3183-3191 (1986).
12. Jain, R. K. Transport of molecules, particles, and cells in solid tumors. *Annu Rep Biomed Eng* 1, 241-263 (1999).
13. Maeda, H. The enhanced permeability and retention (EPR) effect in tumor vasculature: the key role of tumor-selective macromolecular drug targeting. *Adv Enzyme Regul* 41, 189-207 (2001).
14. Ferrari, M. Cancer nanotechnology: opportunities and challenges. *Nat Rev Cancer* 5, 161-171 (2005).
15. Fojo, T. & Menefee, M. Mechanisms of multidrug resistance: the potential role of microtubule-stabilizing agents. *Ann Oncol* 18 Suppl 5, v3-8 (2007).
16. Atalay, C., Deliloglu Gurhan, I., Irkkan, C. & Gunduz, U. Multidrug resistance in locally advanced breast cancer. *Tumour Biol* 27, 309-318 (2006).
17. Trock, B. J., Leonessa, F. & Clarke, R. Multidrug resistance in breast cancer: a meta-analysis of MDR1/gp170 expression and its possible functional significance. *J Natl Cancer Inst* 89, 917-931 (1997).
18. Pivot, X., Asmar, L., Buzdar, A. U., Valero, V. & Hortobagyi, G. A unified definition of clinical anthracycline resistance breast cancer. *Br J Cancer* 82, 529-534 (2000).
19. Wong, S. T. & Goodin, S. Overcoming drug resistance in patients with metastatic breast cancer. *Pharmacotherapy* 29, 954-965 (2009).
20. Al-Hajj, M., Wicha, M. S., Benito-Hernandez, A., Morrison, S. J. & Clarke, M. F. Prospective identification of tumorigenic breast cancer cells. *Proc. Natl Acad Sci USA* 100, 3983-3988 (2003).

21. Yu, F. et al. let-7 regulates self renewal and tumorigenicity of breast cancer cells. *Cell* 131, 1109-1123 (2007).
22. Ponti, D. et al. Isolation and in vitro propagation of tumorigenic breast cancer cells with stem/progenitor cell properties. *Cancer Res* 65, 5506-5511 (2005).
23. Tiezzi, D. G. et al. CD44(+)/CD24 (−) cells and lymph node metastasis in stage I and II invasive ductal carcinoma of the breast. *Med Oncol* (2011).
24. Giatromanolaki, A., Spyridis, E., Fiska, A. & Koukourakis, M. I. The CD44+/CD24− phenotype relates to 'triple-negative' state and unfavorable prognosis in breast cancer patients. *Med Oncol* (2010).
25. Stratford, A. L., Reipas, K., Maxwell, C. & Dunn, S. E. Targeting tumour-initiating cells to improve the cure rates for triple-negative breast cancer. *Expert Rep Mol Med* 12, e22 (2010).
26. Marchini, C. et al. Mesenchymal/stromal gene expression signature relates to basal-like breast cancers, identifies bone metastasis and predicts resistance to therapies. *PLoS One* 5, e14131 (2010).
27. Karnoub, A. E. et al. Mesenchymal stem cells within tumour stroma promote breast cancer metastasis. *Nature* 449, 557-563 (2007).
28. Ferrari, M. Frontiers in cancer nanomedicine: directing mass transport through biological barriers. *Trends Biotechnol* 28, 181-188 (2010).
29. Tasciotti, E. et al. Mesoporous silicon particles as a multistage delivery system for imaging and therapeutic applications. *Nat Nanotechnol* 3, 151-157 (2008).
30. Shen, H. et al. Enhancing chemotherapy response with sustained EphA2 silencing using multistage vector delivery. *Clin Cancer Res* (accepted) (2013).
31. Ferrari, M. Vectoring siRNA therapeutics into the clinic. *Nat Rep Clin Oncol* 7, 485-486 (2010).
32. Tanaka, T. et al. Sustained small interfering RNA delivery by mesoporous silicon particles. *Cancer Res* 70, 3687-3696 (2010).
33. Xu, R. et al. Multistage Vectored siRNA Targeting Ataxia-Telangiectasia Mutated for Breast Cancer Therapy. *Small* (in press) (2013).
34. Tanaka, T. et al. In vivo evaluation of safety of nanoporous silicon carriers following single and multiple dose intravenous administrations in mice. *Int J Pharm* 402, 190-197 (2010).
35. Decuzzi, P. et al. Size and shape effects in the biodistribution of intravascularly injected particles. *J Control Release* 141, 320-327 (2010).
36. van de Ven, A. L. et al. Rapid tumoritropic accumulation of systemically injected plateloid particles and their biodistribution. *J Control Release* (2011).
37. Hurst, D. R. et al. Breast cancer metastasis suppressor 1 up-regulates miR-146, which suppresses breast cancer metastasis. *Cancer Res* 69, 1279-1283 (2009).
38. Lu, X. & Kang, Y. Efficient acquisition of dual metastasis organotropism to bone and lung through stable spontaneous fusion between MDA-MB-231 variants. *Prot. Natl Acad Sci USA* 106, 9385-9390 (2009).
39. Minn, A. J. et al. Genes that mediate breast cancer metastasis to lung. *Nature* 436, 518-524 (2005).
40. Ginestier, C. et al. ALDH1 is a marker of normal and malignant human mammary stem cells and a predictor of poor clinical outcome. *Cell Stem Cell* 1, 555-567 (2007).
41. Li, X. et al. Intrinsic resistance of tumorigenic breast cancer cells to chemotherapy. *J Natl Cancer Inst* 100, 672-679 (2008).
42. Marusyk, A., Almendro, V. & Polyak, K. Intra-tumour heterogeneity: a looking glass for cancer? *Nat Rep Cancer* 12, 323-334 (2012).
43. Farmer, P. et al. A stroma-related gene signature predicts resistance to neoadjuvant chemotherapy in breast cancer. *Nat Meed* 15, 68-74 (2009).
44. Al-Haj j, M. Cancer stem cells and oncology therapeutics. *Curr Opin Oncol* 19, 61-64 (2007).
45. Shah, N. P. et al. Transient potent BCR-ABL inhibition is sufficient to commit chronic myeloid leukemia cells irreversibly to apoptosis. *Cancer Cell* 14, 485-493 (2008).
46. Mann, A. P. et al. E-selectin-targeted porous silicon particle for nanoparticle delivery to the bone marrow. *Adv dater* 23, H278-282 (2011).
47. Decuzzi, P. & Ferrari, M. Design maps for nanoparticles targeting the diseased microvasculature. *Biomaterials* 29, 377-384 (2008).
48. Shen, H. et al. Cooperative, nanoparticle-enabled thermal therapy of breast cancer. *Adv Healthcare Mater* 1, 84-89 (2012).
49. Alhareth, K., Vauthier, C., Gueutin, C., Ponchel, G. & Moussa, F. HPLC quantification of doxorubicin in plasma and tissues of rats treated with doxorubicin loaded poly (alkylcyanoacrylate) nanoparticles. *J Chromatogr B Analyte Technol Biomed Life Sci* 887-888, 128-132 (2012).
50. Ananta, J. S., B. Godin, et al. (2010). "Geometrical confinement of gadolinium-based contrast agents in nanoporous particles enhances T1 contrast." *Nat Nanotechnol* 5(11): 815-821.
51. Anderson, W. F., B. E. Chen, et al. (2006). "Effects of estrogen receptor expression and histopathology on annual hazard rates of death from breast cancer." *Breast Cancer Res Treat* 100(1): 121-126.
52. Bauer, K. R., M. Brown, et al. (2007). "Descriptive analysis of estrogen receptor (ER)-negative, progesterone receptor (PR)-negative, and HER2-negative invasive breast cancer, the so-called triple-negative phenotype: a population-based study from the California cancer Registry." *Cancer* 109(9): 1721-1728.
53. Burstein, H. J., A. D. Elias, et al. (2008). "Phase II study of sunitinib malate, an oral multitargeted tyrosine kinase inhibitor, in patients with metastatic breast cancer previously treated with an anthracycline and a taxane." *J Clin Oncol* 26(11): 1810-1816.
54. Kummar, S., A. Chen, et al. (2011). "Phase I study of PARP inhibitor ABT-888 in combination with topotecan in adults with refractory solid tumors and lymphomas." *Cancer Res* 71(17): 5626-5634.
55. Kummar, S., R. Kinders, et al. (2009). "Phase 0 clinical trial of the poly (ADP-ribose) polymerase inhibitor ABT-888 in patients with advanced malignancies." *J Clin Oncol* 27(16): 2705-2711.
56. Liedtke, C., C. Mazouni, et al. (2008). "Response to neoadjuvant therapy and long-term survival in patients with triple-negative breast cancer." *J Clin Oncol* 26(8): 1275-1281.
57. Lin, N. U., E. Claus, et al. (2008). "Sites of distant recurrence and clinical outcomes in patients with metastatic triple-negative breast cancer: high incidence of central nervous system metastases." *Cancer* 113(10): 2638-2645.
58. Minotti, G., P. Menna, et al. (2004). "Anthracyclines: molecular advances and pharmacologic developments in antitumor activity and cardiotoxicity." *Pharmacol Rev* 56(2): 185-229.

59. Murakami, M., H. Cabral, et al. (2011). "Improving drug potency and efficacy by nanocarrier-mediated subcellular targeting." *Sci Transl Med* 3(64): 64ra62.
60. Navarro, G., R. R. Sawant, et al. (2012). "P-glycoprotein silencing with siRNA delivered by DOPE-modified PEI overcomes doxorubicin resistance in breast cancer cells." *Nanomedicine (Lond)* 7(1): 65-78.
61. Peto, R., J. Boreham, et al. (2000). "UK and USA breast cancer deaths down 25% in year 2000 at ages 20-69 years." *Lancet* 355(9217): 1822.
62. Susa, M., A. K. Iyer, et al. (2009). "Doxorubicin loaded Polymeric Nanoparticulate Delivery System to overcome drug resistance in osteosarcoma." *BMC Cancer* 9: 399.
63. Tutt, A., M. Robson, et al. (2010). "Oral poly(ADP-ribose) polymerase inhibitor olaparib in patients with BRCA1 or BRCA2 mutations and advanced breast cancer: a proof-of-concept trial." *Lancet* 376(9737): 235-244.
64. Twelves, C., J. M. Trigo, et al. (2008). "Erlotinib in combination with capecitabine and docetaxel in patients with metastatic breast cancer: a dose-escalation study." *Eur J Cancer* 44(3): 419-426.
65. Van den Hurk, C. J., R. Eckel, et al. (2011). "Unfavourable pattern of metastases in MO breast cancer patients during 1978-2008: a population-based analysis of the Munich Cancer Registry." *Breast Cancer Res Treat.*
66. Von Hoff, D. D., M. W. Layard, et al. (1979). "Risk factors for doxorubicin-induced congestive heart failure." *Ann Intern Med* 91(5): 710-717.
67. Yu, F., H. Yao, et al. (2007). "let-7 regulates self renewal and tumorigenicity of breast cancer cells." *Cell* 131(6): 1109-1123.
68. "Multistage Delivery of Active Agents", U.S. patent application Ser. No. 11/836,004, filed Aug. 8, 2007, Publication No. US 2008/0311182.

What is claimed is:

1. A composition for the delivery and sustained release of an active agent to a target cell of a subject in need thereof, comprising:
    at least one porous particle, wherein the porous particle is a silicon-based particle, wherein the porous particle comprises a plurality of microscale reservoirs, wherein the plurality of microscale reservoirs comprise an open cavity that is open to a surface of the porous particle;
    at least one polymer comprising poly-L-glutamic acid; and
    at least one active agent comprising doxorubicin,
        wherein the at least one active agent is covalently linked via a cleavable bond to the at least one polymer to form a polymer-active agent conjugate, wherein the cleavable bond is cleavable in response to an environmental condition within the target cell, and wherein the cleavable bond comprises a hydrazone bond,
        wherein the polymer-active agent conjugate is dispersibly contained in the plurality of microscale reservoirs of the at least one porous particle as single molecules,
        wherein the porous particle undergoes physiological degradation to release the polymer-active agent conjugate,
        wherein the released polymer-active agent conjugate is capable of self-assembling into nanoparticles upon contacting an aqueous environment, and
        wherein the active agent is released with zero-order or near zero-order release kinetics following administration of the composition.

2. The composition of claim 1, wherein the porous particle is a micro or a nano particle.
3. The composition of claim 1, wherein the porous particle is biocompatible and degradable.
4. The composition of claim 1, wherein the plurality of microscale reservoirs of the at least one porous particle have a size ranging from about 0.3 µm to about 4 µm.
5. The composition of claim 1, wherein the porous particle is configured into a shape selected from the group consisting of discoidal, spheroid, non-spheroid, oblate spheroid, and combinations thereof.
6. The composition of claim 1, wherein the porous particle is a porous oxide material or a porous etched material.
7. The composition of claim 6, wherein the porous oxide material is porous silicon oxide.
8. The composition of claim 6, wherein the porous etched material is porous silicon.
9. The composition of claim 1, wherein the porous particle is able to overcome at least one biological barrier.
10. The composition of claim 9, wherein the biological barrier is selected from the group consisting of a hemorheology barrier, a reticulo-endothelial barrier, a blood brain barrier, a tumor associated osmotic interstitial pressure barrier, an ionic and molecular pump barrier, a cell membrane barrier, an enzymatic degradation barrier, a nuclear membrane barrier, and combinations thereof.
11. The composition of claim 1, wherein the porous particle further comprises at least one targeting moiety on its surface, and wherein the targeting moiety is specifically directed against the target cell.
12. The composition of claim 11, wherein the at least one targeting moiety is selected from the group consisting of antibodies, antibody fragments, peptides, aptamers, small molecules, and combinations thereof.
13. The composition of claim 1, where the polymer-active agent conjugate enters the target cell through the vesicular transport system.
14. The composition of claim 1, wherein the target cell is a therapy-resistant cancer cell.
15. The composition of claim 1, wherein the subject has cancer, and wherein the cancer is selected from the group consisting of breast cancer, lung cancer, prostate cancer, ovarian cancer, brain cancer, liver cancer, cervical cancer, bone cancer, esophageal cancer, bladder cancer, uterine cancer, testicular cancer, leukemia, lymphoma, stomach cancer, pancreatic cancer, and combinations thereof.
16. The composition of claim 1, wherein the subject has breast cancer, and wherein the breast cancer is Triple Negative breast cancer.
17. A method of treating a tumor, comprising a step of administering to a subject in need thereof a composition of claim 1, wherein the polymer-active agent conjugate is released at a target tumor cell from the porous particle, and wherein the polymer-active agent conjugate enters the target tumor cell via a vesicular transport system.
18. The method of claim 17, wherein the porous particle is a micro or a nano particle.
19. The method of claim 17, wherein the porous particle is biocompatible and biodegradable.
20. The method of claim 17, wherein the plurality of microscale reservoirs of the at least one porous particle have a size ranging from about 0.3 µm to about 4 µm.
21. The method of claim 17, wherein the porous particle is configured into a shape selected from the group consisting of discoidal, spheroid, non-spheroid, oblate spheroid, and combinations thereof.

22. The method of claim 17, wherein the porous particle is a porous silicon oxide material or a porous etched material.

23. The method of claim 22, wherein the porous particle is porous silicon oxide.

24. The method of claim 22, wherein the porous etched material is porous silicon.

25. The method of claim 17, wherein the porous particle is able to overcome at least one biological barrier.

26. The method of claim 25, wherein the biological barrier is selected from the group consisting of a hemo-rheology barrier, a reticulo-endothelial barrier, a blood brain barrier, a tumor associated osmotic interstitial pressure barrier, an ionic and molecular pump barrier, a cell membrane barrier, an enzymatic degradation barrier, a nuclear membrane barrier, and combinations thereof.

27. The method of claim 17, wherein the porous particle further comprises at least one targeting moiety on its surface, wherein the targeting moiety is specifically directed against the target tumor cell.

28. The method of claim 27, wherein the at least one targeting moiety is selected from the group consisting of antibodies, antibody fragments, peptides, aptamers, small molecules, and combinations thereof.

29. The method of claim 17, wherein the target tumor cell of the subject is a therapy-resistant cancer cell.

30. The method of claim 17, wherein the subject has cancer, and wherein the cancer is selected from the group consisting of breast cancer, lung cancer, prostate cancer, ovarian cancer, brain cancer, liver cancer, cervical cancer, bone cancer, esophageal cancer, bladder cancer, uterine cancer, testicular cancer, leukemia, lymphoma, stomach cancer, pancreatic cancer, and combinations thereof.

31. The method of claim 1, wherein the subject has breast cancer, and wherein the breast cancer is Triple Negative breast cancer.

32. A method of eliminating tumor stem cells, comprising the step of administering to a subject in need thereof a composition of claim 1, wherein the polymer-active agent conjugate is released at a target tumor stem cell from the porous particle, and wherein the polymer-active agent conjugate enters the tumor stem cell via a vesicular transport system.

33. The method of claim 32, wherein the porous particle is a micro or a nano particle.

34. The method of claim 32, wherein the porous particle is biocompatible and biodegradable.

35. The method of claim 32, wherein the plurality of microscale reservoirs of the at least one porous particle have a pore size ranging from about 0.3 µm to about 4 µm.

36. The method of claim 32, wherein the porous particle is configured into a shape selected from the group consisting of discoidal, spheroid, non-spheroid, oblate spheroid, and combinations thereof.

37. The method of claim 32, wherein the porous particle is a porous silicon oxide material or a porous etched material.

38. The method of claim 37, wherein the porous particle is porous silicon oxide.

39. The method of claim 37, wherein the porous etched material is porous silicon.

40. The method of claim 32, wherein the porous particle is able to overcome at least one biological barrier.

41. The method of claim 40, wherein the biological barrier is selected from the group consisting of a hemo-rheology barrier, a reticulo-endothelial barrier, a blood brain barrier, a tumor associated osmotic interstitial pressure barrier, an ionic and molecular pump barrier, a cell membrane barrier, an enzymatic degradation barrier, a nuclear membrane barrier, and combinations thereof.

42. The method of claim 32, wherein the porous particle further comprises a targeting moiety on its surface, wherein the targeting moiety is specifically directed against the target cell.

43. The method of claim 42, wherein the targeting moiety is selected from the group consisting of antibodies, antibody fragments, peptides, aptamers, small molecules, and combinations thereof.

44. The method of claim 32, wherein the tumor stem cell of the subject is a therapy-resistant cancer cell.

45. The method of claim 44, wherein the subject has cancer, and wherein the cancer is selected from the group consisting of breast cancer, lung cancer, prostate cancer, ovarian cancer, brain cancer, liver cancer, cervical cancer, bone cancer, esophageal cancer, bladder cancer, uterine cancer, testicular cancer, leukemia, lymphoma, stomach cancer, pancreatic cancer, and combinations thereof.

46. The method of claim 45, wherein the subject has breast cancer, and wherein the breast cancer is Triple Negative breast cancer.

47. A method of circumventing multi-drug resistance in a tumor cell, comprising the step of administering to a subject in need thereof a composition of claim 1, wherein the polymer-active agent conjugate is released at the tumor cell from the porous particle, and wherein the polymer-active agent conjugate enters the tumor cell via the vesicular transport system.

48. The method of claim 47, wherein the porous particle is a micro or a nano particle.

49. The method of claim 47, wherein the porous particle is biocompatible and biodegradable.

50. The method of claim 47, wherein the plurality of microscale reservoirs of the at least one porous particle have a pore size ranging from about 0.3 µm to about 4 µm.

51. The method of claim 47, wherein the porous particle is configured into a shape selected from the group consisting of discoidal, spheroid, non-spheroid, oblate spheroid, and combinations thereof.

52. The method of claim 47, wherein the porous particle is a porous silicon oxide material or a porous etched material.

53. The method of claim 52, wherein the porous particle is porous silicon oxide.

54. The method of claim 52, wherein the porous etched material is porous silicon.

55. The method of claim 47, wherein the porous particle is able to overcome at least one biological barrier.

56. The method of claim 55, wherein the biological barrier is selected from the group consisting of a hemo-rheology barrier, a reticulo-endothelial barrier, a blood brain barrier, a tumor associated osmotic interstitial pressure barrier, an ionic and molecular pump barrier, a cell membrane barrier, an enzymatic degradation barrier, a nuclear membrane barrier, and combinations thereof.

57. The method of claim 47, wherein the porous particle further comprises a targeting moiety on its surface, wherein the targeting moiety is specifically directed against the target cell.

58. The method of claim 57, wherein the targeting moiety is selected from the group consisting of antibodies, antibody fragments, peptides, aptamers, small molecules, and combinations thereof.

59. The method of claim 47, wherein the subject has breast cancer, and wherein the breast cancer is Triple Negative breast cancer.

60. The composition of claim 1, wherein the nanoparticles have a diameter of less than 1 μm.

61. The composition of claim 1, wherein the nanoparticles have a diameter of less than about 200 nm.

62. The composition of claim 1, wherein the nanoparticles have diameters ranging from about 100 nm to about 200 nm.

63. The composition of claim 1, wherein the cleavable bond is cleavable in acidic environments of late endosomes or lysosomes within the target cell.

* * * * *